United States Patent
Sharma et al.

(10) Patent No.: US 12,285,460 B2
(45) Date of Patent: *Apr. 29, 2025

(54) PHARMACEUTICAL COMPOSITIONS

(71) Applicant: RHYTHM PHARMACEUTICALS, INC., Boston, MA (US)

(72) Inventors: Shubh Sharma, Cranbury, NJ (US); Leonardus H. T. Van Der Ploeg, Newton, MA (US); Bart T. Henderson, Belmont, MA (US)

(73) Assignee: RHYTHM PHARMACEUTICALS, INC., Boston, MA (US)

(*) Notice: Subject to any disclaimer, the term of this patent is extended or adjusted under 35 U.S.C. 154(b) by 125 days.

This patent is subject to a terminal disclaimer.

(21) Appl. No.: 17/401,929

(22) Filed: Aug. 13, 2021

(65) Prior Publication Data

US 2022/0160818 A1 May 26, 2022

Related U.S. Application Data

(63) Continuation of application No. 14/775,911, filed as application No. PCT/US2014/029421 on Mar. 14, 2014, now Pat. No. 11,129,869.

(60) Provisional application No. 61/792,440, filed on Mar. 15, 2013.

(51) Int. Cl.
| | | |
|---|---|---|
| *A61K 38/12* | (2006.01) |
| *A61K 9/08* | (2006.01) |
| *A61K 9/10* | (2006.01) |
| *A61K 9/14* | (2006.01) |
| *A61K 38/08* | (2019.01) |
| *A61K 45/06* | (2006.01) |
| *A61K 47/10* | (2017.01) |
| *A61K 47/12* | (2006.01) |
| *A61K 47/24* | (2006.01) |
| *A61K 47/38* | (2006.01) |
| *A61K 47/54* | (2017.01) |

(52) U.S. Cl.
CPC .......... *A61K 38/12* (2013.01); *A61K 9/08* (2013.01); *A61K 9/10* (2013.01); *A61K 9/146* (2013.01); *A61K 38/08* (2013.01); *A61K 45/06* (2013.01); *A61K 47/10* (2013.01); *A61K 47/12* (2013.01); *A61K 47/24* (2013.01); *A61K 47/38* (2013.01); *A61K 47/541* (2017.08); *A61K 47/542* (2017.08); *A61K 47/544* (2017.08)

(58) Field of Classification Search
None
See application file for complete search history.

(56) References Cited

U.S. PATENT DOCUMENTS

| | | |
|---|---|---|
| 5,731,408 A | 3/1998 | Hadley et al. |
| 5,849,704 A | 12/1998 | Sørensen et al. |
| 7,655,468 B2 * | 2/2010 | Huang .............. A61K 47/543 536/23.1 |
| 8,039,435 B2 | 10/2011 | Dong et al. |
| 8,349,797 B2 | 1/2013 | Dong et al. |
| 8,563,000 B2 | 10/2013 | Dong et al. |
| 9,155,777 B2 | 10/2015 | Alem et al. |
| 11,129,869 B2 * | 9/2021 | Sharma .............. A61K 47/544 |
| 2005/0267147 A1 | 12/2005 | Poitout et al. |
| 2006/0173036 A1 | 8/2006 | Poitout et al. |
| 2006/0281784 A1 | 12/2006 | Poitout et al. |
| 2009/0209531 A1 | 8/2009 | Poitout et al. |
| 2010/0173834 A1 | 7/2010 | Dong |
| 2012/0135923 A1 | 5/2012 | Halem et al. |
| 2012/0225816 A1 | 9/2012 | Dong et al. |
| 2012/0226018 A1 | 9/2012 | Dong |
| 2014/0127303 A1 | 5/2014 | Richard et al. |
| 2015/0157719 A1 | 6/2015 | Baronnet et al. |

FOREIGN PATENT DOCUMENTS

| | | |
|---|---|---|
| CN | 101257916 A | 9/2008 |
| CN | 101439182 A | 5/2009 |
| JP | 2005-504715 A | 2/2005 |
| JP | 2007-517023 A | 6/2007 |
| WO | 94/26251 A1 | 11/1994 |
| WO | 98/25642 A2 | 6/1998 |

(Continued)

OTHER PUBLICATIONS

Al-Obeidi et al., "Potent and Prolonged Acting Cyclic Lactam Analogues of a-Melanotropin: Design Based on Molecular Dynamics" J. Med. Chem (1989) vol. 32 pp. 2555-2561.

Bednarek et al., "Analogs of MTII, Lactam Derivatives of a-Melanotropin, Modified at the N-Terminus, and Their Selectivity at Human Melanocortin Receptors 3, 4 and 5" Biochem. and Biophys. Research Communications (1999) vol. 261 pp. 209-213.

(Continued)

*Primary Examiner* — Thea D'Ambrosio
(74) *Attorney, Agent, or Firm* — Lando & Anastasi, LLP

(57) ABSTRACT

The present invention relates to an ionic complex comprising a cationic polypeptide and an anionic excipient selected from: a PEG-carboxylic acid; a fatty acid having 10 or more carbon atoms; an anionic phospholipid; and a combination thereof. The invention also relates to a pharmaceutical composition comprising the ionic complex of the invention and a pharmaceutically acceptable carrier. The cationic polypeptide of the ionic complex has pharmacological activity and the complex can provide a more desirable pharmacokinetic profile for the cationic polypeptide of the complex as compared to the cationic polypeptide alone following administration. As such, the invention also relates to the use of the ionic complex and pharmaceutical composition comprising same to treat a subject suffering from a disease or disorder that is responsive to the cationic polypeptide of the ionic complex.

11 Claims, 3 Drawing Sheets

Specification includes a Sequence Listing.

(56) References Cited

FOREIGN PATENT DOCUMENTS

| WO | 03006620 A2 | 1/2003 |
| --- | --- | --- |
| WO | 2004045633 A2 | 6/2004 |
| WO | 2005/000339 A2 | 1/2005 |
| WO | 2005014617 A2 | 2/2005 |
| WO | 2007/008704 A2 | 1/2007 |
| WO | 2007022254 A2 | 2/2007 |
| WO | 2008/147556 A2 | 12/2008 |
| WO | 2009/151383 A1 | 12/2009 |
| WO | 2009158415 A1 | 12/2009 |
| WO | 2010/144344 A2 | 12/2010 |
| WO | 2010144038 A1 | 12/2010 |
| WO | 2011060355 A1 | 5/2011 |
| WO | 2012172433 A2 | 12/2012 |
| WO | 2013/032028 A1 | 3/2013 |
| WO | 2013033838 A1 | 3/2013 |
| WO | 2013/182653 A1 | 12/2013 |
| WO | 2014/144260 A1 | 9/2014 |
| WO | 2014/144842 A2 | 9/2014 |

OTHER PUBLICATIONS

Bednarek et al., "Structure-function studies on the cyclic peptide MT-II, lactam derivative of a-melanotropin" Peptides (1999) vol. 20 pp. 401-409.

Grieco et al., "Further structure-activity studies of lactam derivatives of MT-II and SHU-9119: Their activity and selectivity at human melanocortin receptors 3, 4 and 5" Peptides (2007) vol. 28 pp. 1191-1196.

Grieco et al., "Structure-Activity Studies of the Melanocortin Peptides: Discovery of Potent and Selective Affinity Antagonists for the hMC3 and hMC4 Receptors" J. Med. Chem. (2002) vol. 45 pp. 5287-5294.

International Preliminary Report on Patentability and Written Opinion for PCT/US2014/029421 mailed Sep. 15, 2015.

International Search Report from PCT/US2014/029421 mailed Feb. 23, 2015.

Macedo et al., "Estimation of average depth of penetration of melanotropins in dimyristoylphosphatidylglycerol vesicles" Biophysical Chemistry (1999) vol. 59 pp. 193-202.

Vogt & Bechinger, "The Interactions of Histidine-containing Amphipathic Helical Peptide Antibiotics with Lipid Bilayers" The Journal of Biological Chemistry (1999) vol. 274 No 41 pp. 29115-29121.

Farooqi et al. "Dominant and recessive inheritance of morbid obesity associated with melanocortin 4 receptor deficiency", The Journal of Clinical Investigation (2000) vol. 106, No. 2, pp. 271-279.

Vaisse et al. "Melanocortin-4 receptor mutations are a frequent and heterogeneous cause of morbid obesity", The Journal of Clinical Investigation (2000) vol. 106, No. 2, pp. 253-262.

Xiang et al. "Pharmacological characterization of 30 human melanocortin-4 receptor polymorphisms with the endogenous proopiomelanocortin-derived agonists, synthetic agonists, and the endogenous agouti-related protein antagonist." Biochemistry (2010), No. 49(22), pp. 4583-4600.

Farooqi et al. "Clinical and Molecular Genetic Spectrum of Congenital Deficiency of the Leptin Receptor" The New England Journal of Medicine (2007) vol. 356, No. 3, pp. 237-247.

Lee "The Role of Leptin-Melanocortin System and Human Weight Regulation: Lessons from Experiments of Nature" Annals Academy of Medicine, Jan. 2009, vol. 38 No. 1, pp. 34-44.

Krude et al. "Severe early-onset obesity, adrenal insufficiency and red hair pigmentation caused by POMC mutations in humans" Nature Genetics, 1998 vol. 19, pp. 155-157.

Lee et al, "A POMC variant implicates ?-melanocyte-stimulating hormone in the control of human energy balance" Cell Metabolism (2006) vol. 3, Issue 2, pp. 135-140.

Brennan et al., "Drug Insight: the role of leptin in human physiology and pathophysiology-emerging clinical applications" Nature Reviews Endocrinology (2006) vol. 2, pp. 318-327.

European Search Report for European Application No. 14 724 574.0 dated Nov. 18, 2016.

Kievit et al. "Chronic Treatment With a Melanocortin-4 Receptor Agonist Causes Weight Loss, Reduces Insulin Resistence, and Improves Cardiovascular Function in Diet-Induced Obese Rhesus Macaques" Diabetes (2013) vol. 62, pp. 490-497.

Blume et al. "Liposomes for the sustained drug release in vivo" Biochimica et Biophysica Acta (1990) vol. 1029, No. 1, pp 91-97.

Mufamadi et al., "A Review on Composite Liposomal Technologies for Specialized Drug Delivery" J. Drug Delivery (2011) vol. 2011, Article ID: 939851, pp. 1-19.

Katdare, et al., Chap. 17. "Excipients for Protein Drugs," Excipient Development for Pharmaceutical, Biotechnology, and Drug Delivery Systems, Taylor & Francis Group LLC, pp. 291-332 (2006).

Sigma Aldrich, "Polyethylene glycol," Product Information available online at https://www.sigmaaldrich.com/content!dam/sigmaaldrich/docs/Sigma/Product_I nformation_Sheet/1 /p3390pis.pdf, 2 pages (2003).

European Examination Report for Application No. 14724574.0 dated Jul. 16, 2018.

Lotz, "PEGylation for Improving the Properties of Peptide-Based APIs," available at https://www.biocompare.com/Bench-Tips/ 344638-PEGylation-for-Improving-the-Properties-of-Peptide-Based-APIs/, 13 pages (2017) (Year: 2017).

Peptu et al., "Release of liposome-encapsulated calcein from liposome entrapping gelatin-carboxymethylcellulose films: A presentation of differnt possibilities" Journal of Nanoscience and Nanotechnology, 2008, vol. 8, pp. 2249-2258.

"Precipitating", Merriam-Webster Dictionary, available online at https://www.merriam-webster.com/dictionary/precipitate, 17 pages (accessed on Jun. 10, 2018) (Year: 2018).

M.E. Aulton, "Pharmaceutics: The Science of Dosage Form Design", Churchill Livingstone, Second Edition 2002, Chapter 20, 289-305.

Wikipedia: "Setmelanotide", (accessed 2021).

* cited by examiner

PHARMACEUTICAL COMPOSITIONS

RELATED APPLICATION

This application is a continuation of U.S. application Ser. No. 14/775,911, filed Sep. 14, 2015, which is a U.S. National Phase Application under 35 U.S.C. § 371 of International Application No. PCT/US2014/029421, filed Mar. 14, 2014, which claims the benefit of U.S. Provisional Application No. 61/792,440, filed Mar. 15, 2013, the contents of which are incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Oct. 7, 2014, is named R2054-7001WO_SL.txt and is 48,749 bytes in size.

BACKGROUND OF THE INVENTION

It is often desirable to enhance the pharmacokinetic characteristics of an active agent (e.g., to extend the duration of drug action or to minimize any undesirable effects). Drugs, in particular peptidic drug, are typically readily soluble in the body and can be absorbed rapidly resulting in a sudden burst of available drug as opposed to a more gradual release. Compositions that can provide for a more gradual or extended release of drug can result in reduced fluctuations in concentration of the drug following administration, increased drug loading per administration, increased stability and efficacy both in vivo and in vitro, reduced toxicity and increased patient compliance due to less frequent administrations. As such, a need exists for pharmaceutical compositions containing an active agent that provide for an extended release of the active agent.

SUMMARY OF THE INVENTION

The present invention relates to an ionic complex comprising a cationic polypeptide and an anionic excipient selected from: a PEG-carboxylic acid; a fatty acid having 10 or more carbon atoms; an anionic phospholipid; and a combination thereof in different molar ratios. The invention also relates to a pharmaceutical composition comprising the ionic complex of the invention and a pharmaceutically acceptable carrier. The cationic polypeptide of the ionic complex has pharmacological activity and the complex can provide a more desirable pharmacokinetic profile for instance as a sustained release formulation, for the cationic polypeptide of the complex as compared to the cationic polypeptide alone, following administration.

The invention also relates to the use of the ionic complex and pharmaceutical composition comprising same to treat a subject suffering from a disease or disorder that is responsive to the pharmacological activity possessed by the cationic polypeptide of the ionic complex. In one embodiment, the disorder to be treated is responsive to the modulation of the melanocortin-4 receptor (MC4R) in a subject in need of treatment. The method comprises administering to the subject an effective amount of an ionic complex comprising as the cationic polypeptide an MC4R modulator such as those described in Formula I herein. In a particular embodiment, the disorder responsive to modulation of the MC4R includes type 1 diabetes, type 2 diabetes, obesity, insulin resistance, metabolic syndrome, male erectile dysfunction, female sexual disorder, non-alcoholic fatty liver disease, non-alcoholic steatohepatitis, disorders of substance abuse, including alcoholism feeding disorders, cachexia, inflammation and anxiety.

In certain embodiments, the compounds and compositions of the present invention possess higher selectivity and potency for the MC4R and melanocortin-3 receptor (MC3R) when compared to melanocortin-1 receptor (MC1R). The compounds and compositions of the present invention can reduce or eliminate such undesirable side effects as increase in blood pressure effects, increase in heart rate, undesired effects on sexual arousal, and increase in skin pigmentation.

The ionic complex and pharmaceutical compositions of the present invention comprising same can enhance the pharmacokinectic characteristics of the cationic polypeptide of the complex. For example, the duration of pharmacological action of the cationic polypeptide can be extended while significantly narrowing the maximal to minimal drug exposure ratios in its pharmacokinetic profile. The therapeutic dose of the cationic peptide therefore can be maintained within a beneficial exposure range in the body, thereby alleviating the possibility of undesirable side effects that could result due to a high exposure of the cationic polypeptide drug alone. Compositions that can provide for a more gradual or extended release of active can result in reduced fluctuations in concentration of the active following administration, increased active loading per administration, increased stability and efficacy both in vivo and in vitro, reduced toxicity and increased patient compliance due to less frequent administrations. The ionic complex compositions of this invention are suitable for effective therapeutic administration over a diverse set of dosing ranges including at least once daily, once weekly, once every 2 weeks, once every four weeks, once every 2 months, once every 3 months, once every 4 months, once every 5 months or once every 6 months.

DETAILED DESCRIPTION OF THE INVENTION

Figure 1:
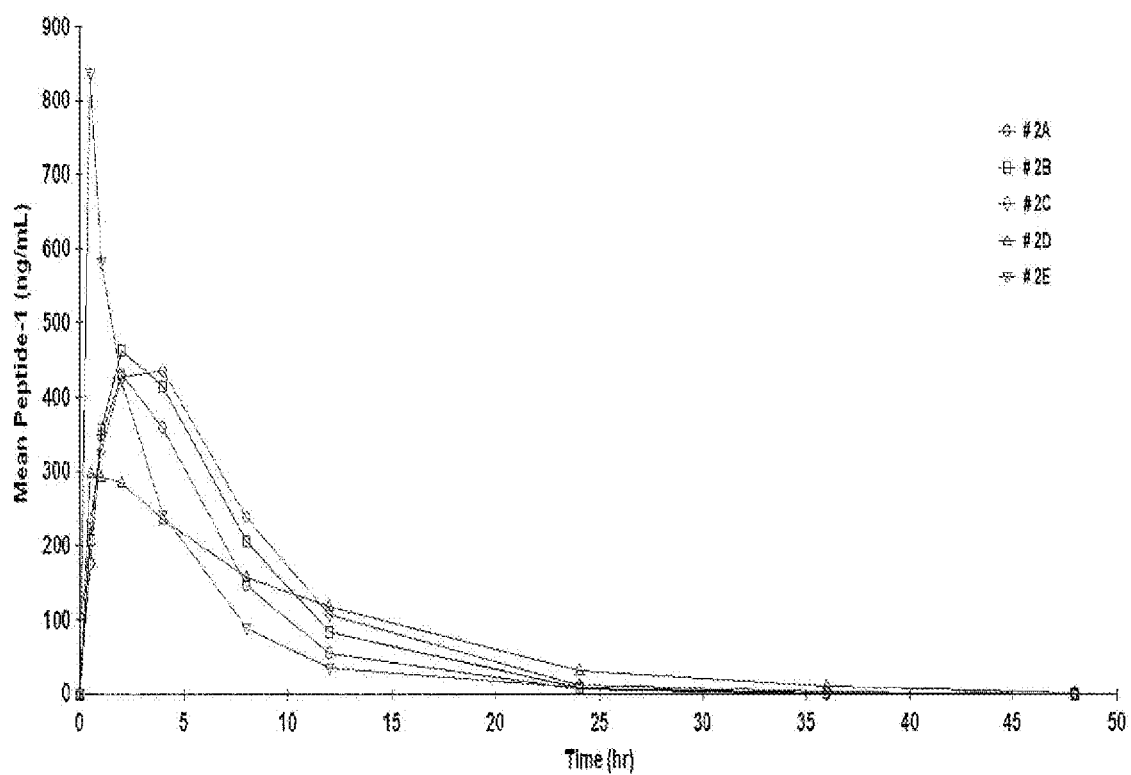
FIG. 1 is a graph showing the pharmacokinetic profile of each of the identified pharmaceutical compositions following administration to cynomolgous monkeys.

A description of example embodiments of the invention follows.

Glossary

The nomenclature used to define the peptides is that typically used in the art wherein the amino group at the N-terminus appears to the left and the carboxyl group at the C-terminus appears to the right.

As used herein, the term "amino acid" includes both a naturally occurring amino acid and a non-natural amino acid. Unless otherwise indicated, all amino acids and their residues found in the compounds described herein can be either in D or L configuration.

Unless defined otherwise, all technical and scientific terms used herein have the same meaning as commonly understood by one of ordinary skill in the art to which this invention belongs. All publications, patent applications, patents and other references mentioned herein are incorporated by reference in their entirety.

| Symbol | Meaning |
|---|---|
| Abu | α-aminobutyric acid |
| Ac | acyl group |
| Aib | α-aminoisobutyric acid |
| Ala or A | alanine |
| Arg or R | arginine |
| Asn or N | asparagine |
| Asp or D | aspartic acid |
| Atc | 2-aminotetralin-2-carboxylic acid |
| Cha | β-cyclohexylalanine |
| sChp | 1-amino-4-phenylcyclohexane-1-carboxylic acid |
| Cys or C | cysteine |
| hCys | homocysteine |
| Dbu | 2,4-diaminobutyric acid |
| Dpr | 2,3-diaminopropionic acid |
| Gln or Q | glutamine |
| Glu or E | glutamic acid |
| Gly or G | glycine |
| His or H | histidine |
| Hyp | hydroxyproline |
| Ile or I | isoleucine |
| Leu or L | leucine |
| Lys or K | lysine |
| Met or M | methionine |
| 1-Nal | (1-naphthyl)-alanine |
| 2-Nal | (2-naphthyl)-alanine |
| Nle | norleucine |
| Orn | ornithine |
| Pen | penicillamine |
| Phe or F | phenylalanine |
| Pro or P | proline |
| QAla | quinolinylalanine or 2-amino-3-(quinolin-3-yl)propanoic acid |
| Sar | sarcosine (N-methylglycine) |
| Ser or S | Serine |
| Tle | tert-leucine (tert-butyl glycine) |
| TzAla | 3-(1,2,4-triazol-1-yl)-L-Ala |
| Thr or T | threonine |
| Trp or W | tryptopham |
| Tyr or Y | tyrosine |
| Val or V | valine |
| BHA | benzhydrylamine |
| Boc | tert-butyloxycarbonyl |
| But | tertiary butyl |
| DIPEA | N,N-diisopropylethylamine |
| DTT | dithiothreitol |
| Fmoc | fluorenylmethyloxycarbonyl |
| HBTU | 2-(1H-benzotriazole-1-yl)-1,1,3,3-tetramethyluronium hexafluorophosphate |
| MCR4 | melanocortin-4 receptor |
| Mtt | 4-methyltrityl |
| NMP | N-methylpyrrolidone |
| OBut | tertiary butoxy |
| OPip | 2-phenylisopropyl |
| Pbf | 2,2,4,6,7-pentamethyldihydrobenzofuran-5-sulfonyl |
| Trt | trityl |
| TIS | triisopropylsilane |
| TFA | trifluoroacetic acid |

Unless otherwise indicated, all abbreviations (e.g. Ala) of amino acids in this disclosure refer to amino acid residues, i.e. stand for the structure of —NH—C(R)(R')—CO—, wherein R and R' each is, independently, hydrogen or the side chain of an amino acid (e.g., R=CH$_3$ and R'=H for Ala, or R and R' may be joined to form a ring system).

The designation "Ac" or "NH$_2$" at a terminus of a polypeptide indicates that the corresponding terminus is acylated or amidated, respectively.

The phrase "a covalent bond between amino acid side chains" means that the side chains of two amino acid residues in question each includes a functional group capable of forming a covalent bond with one another. Examples of such bonds include disulfide bridges formed by Cys, hCys, or Pen side chains, and amid bonds formed by an amino group of one amino acid side chain and a carboxy group of another amino acid side chain, such as, e.g. Asp, Glu, Lys, Orn, Dbu, or Dpr. When a covalent bond between amino acid side chains is formed, the polypeptide may become cyclized. Such a cyclic polypeptide may be indicated either by a structural formula or by using the shorthand notation "c( )" or "cyclco( )" For example, "-c(Cys-Cys)-" or "-cyclo(Cys-Cys)-" denotes the structure:

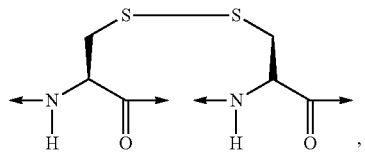

while "-c(Asp-Lys)-" or "-cyclo(Asp-Lys)-" denotes the structure:

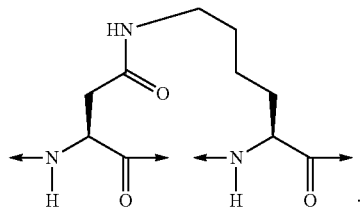

Ionic Complex:

The invention relates to an ionic complex comprising a cationic polypeptide and an anionic excipient selected from: a PEG-carboxylic acid; a fatty acid having 10 or more carbon atoms; a phospholipid; and a combination thereof. The molar ratio of the cationic polypeptide to the anionic excipient in the ionic complex ranges from, for instance, about 1:1 to about 1:10 wherein the molar ratio is based on a charge of the cationic polypeptide to charge of the anionic excipient. The molar ratio is frequently selected from about 1:1, about 1:2, about 1:3, about 1:4, about 1:5, about 1:6, about 1:7, about 1:8, about 1:9, or about 1:10.

Anionic Excipients

Anionic Phospholipid:

As used herein, an "anionic phospholipid is a phospholipid wherein one or more oxygen atoms of the phosphate group(s) has been deprotonated resulting in an organophosphate oxoanion and a negatively charged lipid. The naturally occurring anionic phospholipids typically comprise a $C_{16}$ or larger fatty acid chain. The anionic phospholipid can bear one or more negative charges (e.g., 1, 2, 3, 4, 5, 6 or more). In some embodiments the anionic phospholipid is selected from: a phosphatidic acid (PA), a phosphatidylglycerol (PG), a phosphatidylinositol (PI), or a phosphatidylserine (PS). Suitable anionic lipids include: L-α-phosphatidic acid, 1-oleoyl lysophophatidic acid, L-α-phosphatidylglycerol, 1,2-di-O-tetradecyl-sn-glycero-3-phospho-(1'-rac-glycerol), 1,2-dimyristoyl-sn-glycero-3-phospho-(1'-rac-glycerol) (DMPG), 1,2-dimyristoyl-sn-glycero-3-phospho-L-serine (DMPS), 1,2-dipalmitoyl-sn-glycero-3-phosphatidic acid (DPPA), 1,2-distearoyl-sn-glycero-3-phosphatidic acid (DSPA), 1,2-disteroyl-sn-glycero-3-phosphoethanolamine (DSPE), mPEG-2,000-DSPE, mPEG-5,000-DSPE, 1,2-dipalmitoyl-sn-glycero-3-phosphoethanolamine (DPPE), mPEG-2,000-DPPE, mPEG-5,000-DPPE, 1-(1,2-dihexadecanoylphosphatidyl)inositol-4,5-bisphosphate, trisodium salt, and 1-(1,2-dihexadecanoylphosphatidyl)inositol-3, 4,5-triphosphate, tetrasodium salt, 1-palmitoyl-2-oleoylphosphatidylglycerol (POPG), 1-palmitoyl-2-arachidonoyl-sn-glycero-3-phosphoglycerol (PAPG), DSPG (Distearoyl Phosphatidyglycerol), DPPG (Dipalmitoyl Phosphatidyglycerol), DEPG (Dielaidoyl Phosphatidyglycerol), DOPG (Dioleoyl Phosphatidyglycerol), DEPA (Dielaidoy Phosphatidic Acid), DOPA (Dioleoyl Phosphatidic Acid), DSPS (Distearoyl Phosphatidylserine), DPPS (Dipalmitoyl Phosphatidylserine), DEPS (Dielaidoy Phosphatidylserine), and DOPS (Dioleoyl Phosphatidylserine), L-α-lysophosphatidylserine, L-α-lysophosphatidylinositol, tetradecylphosphonic acid, L-α-phosphatidylinositol-4-phosphate, L-α-phosphatidylinositol-4,5-bisphosphate, 1,2-diphytanoyl-sn-glycero-3-phosphate, 1,2-di-O-tetradecyl-sn-glycero-3-phospho-(1'-rac-glycerol) and mixtures thereof.

Specific anionic phospholipids for use in the present invention are 1,2-Distearoyl-sn-Glycero-3-Phosphoethanolamine (DSPE) conjugated Polyethylene Glycol, the structure of which is as follows:

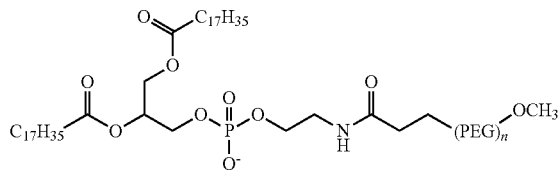

with the value of "n" varying with molecular weight. Such anionic phospholipids are referred to herein as mPEG-(Mol. Wt.)DSPE. Suitable examples include, mPEG-2,000-DSPE and mPEG-5,000-DSPE wherein DSPE is 1,2-disteroyl-sn-glycero-3-phosphoethanolamine. Other example include mPEG-2,000-DPPE and mPEG-5,000-DPPE wherein DPPE is 1,2-dipalmitoyl-sn-glycero-3-phosphoethanolamine.

Synthetically anionic phospholides with chain lengths shorter than $C_{16}$ can also be obtained and utilized. Synthetic lipids can also be obtained with fatty acids that provide for additional anionic groups in the fatty acid chains. For example, a 1-palmitoyl-2-glutaryl-sn-glycero-3-phosphocholine which incorporates a shorter fatty acid chain that terminates in a carboxylate group.

These naturally occurring and synthetic anionic lipids may be obtained from several commercial sources such as, Avanti polar lipids (Alabaster, AL), or Lipoid LLC (Newark, NJ), or Cordon Pharma (Boulder, CO), or NOF Corp America (White Plains, NY).

Fatty Acid:

As used herein, a "fatty acid" is a carboxylic acid with a long aliphatic tail (chain), which is either saturated or unsaturated and has a carbon atom chain of 10 or more atoms. The carbon atom chain can be a linear, branched, saturated, mono or poly-unsaturated chain.

Suitable saturated fatty acids include, but are not limited to: capric acid, lauric acid, myristic acid, palmitic acid, stearic acid, arachidic acid, docosanoic acid, tetracosanoic acid, and hexacosanoic acid.

Suitable unsaturated fatty acids include, but are not limited to: cis-2-decenoic acid, myristoleic acid, palmitoleic acid, sapienic acid, oleic acid, elaidic acid, vaccenic acid, linoleic acid, linoelaidic acid, α-linolenic acid, arachidonic acid, cis-parinaric acid, eicosapentaenoic acid, and phytanic acid.

PEG-Carboxylic Acids:

As used herein, a "PEG-carboxylic acid" means a polyethylene glycol (PEG) polymer that has been functionalized with a carboxylic acid. The PEG can be functionalized to be monofunctional (monocarboxylate) or homobifunctional (dicarboxylate). The functionalized PEG can be linear or branched. The PEG-carboxylic acid suitable for use in the invention can have an average molecular weight range of from about 1,000 to about 100,000.

Homobifunctional PEGs suitable for use in the invention can be generally depicted as COOH-PEG-COOH, or by the chemical formula:

COOH—$(CH_2CH_2O)_n$—$CH_2CH_2$—COOH, or COOH—$CH_2CH_2$—CO—O$(CH_2CH_2O)_n$—$CH_2CH_2$—COOH, or COOH—$CH_2CH_2$—CO—O$(CH_2CH_2O)_n$—CO—$CH_2CH_2$—COOH with the value of "n" varying with molecular weight. For example, the PEG-carboxylic acid denoted in the examples as PEG-10,000-dicarboxylate is a homobifunctional PEG having a molecular weight of 10,000. An average molecular weight range of from about 1,000 to about 100,000 is suitable. Typically, molecular weights can range from 1,000-40,000

One type of monofunctional PEG-carboxylic acids suitable for use in the invention can be generally depicted as mPEG-COOH, or by the chemical formula: $CH_3O$—$(CH_2CH_2O)_n$—$CH_2CH_2$—COOH or $CH_3O$—$(CH_2CH_2O)_n$—CO—$CH_2CH_2$—COOH again with the value of "n" varying with molecular weight. For example, the mPEG-10000 used in the examples would a monofunctional PEG having a methoxy group as indicate in the formula. An average molecular weight range of from about 1,000 to about 100,000 is suitable. Typically, molecular weights can range from 1,000-40,000

Another type of monofunctional PEG-carboxylic acid suitable for use in the invention can be generally depicted as PEG-COOH or by the chemical formula: HO—($CH_2CH_2O)_n$—$CH_2CH_2$—COOH with the value of "n" varying with molecular weight. For example, the PEG-carboxylic acid denoted in the examples as PEG-10,000-monocarboxylate is a monofunctional PEG having a molecular weight of 10,000. An average molecular weight range of from about 1,000 to about 100,000 is suitable. Typically, molecular weights can range from 1,000-40,000

Suitable PEG-carboxylic acids include, but are not limited to, PEG-10,000-monocarboxylate, PEG-20,000-monocarboxylate, mPEG-1,000-monocarboxylate, mPEG-2,000-monocarboxylate, mPEG-5,000-monocarboxylate, mPEG-10,000-monocarboxylate, mPEG-20,000-monocarboxylate, mPEG-30,000-monocarboxylate, mPEG-40,000-monocarboxylate, PEG-1,000-dicarboxylate, PEG-2,000-dicarboxylate, PEG-3,500-dicarboxylate, PEG-5,000-dicarboxylate, PEG-7,500-dicarboxylate, PEG-10,000-dicarboxylate, and Y-shape PEG-40,000-monocarboxylate. The Y-Shaped PEG-Carboxylic Acids referred to above can be depicted as follows:

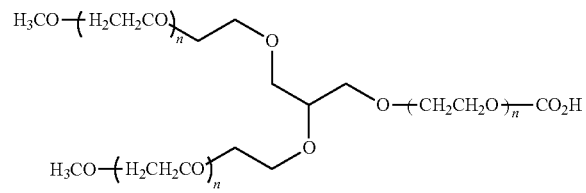

again with the value of "n" determining the molecular weight.

In particular embodiments, the PEG-carboxylic acid is selected from: PEG-5,000-monocarboxylate, PEG-10,000-monocarboxylate, PEG-20,000-monocarboxylate, mPEG-5,000-monocarboxylate, mPEG-10,000-monocarboxylate, mPEG-20,000-monocarboxylate, PEG-5,000-dicarboxylate, and PEG-10,000-dicarboxylate.

Suitable PEG-carboxylic acids can be commercially obtained from Nanocs, Inc. (New York, NY), JenKem Technology (Allen, TX), or NOF Corp America (White Plains, NY).

In certain embodiments, two or more of the anionic excipients described above (e.g., PEG-carboxylic acid, anionic phospholipid and fatty acid) can be employed in the formulation. For example, a PEG-carboxylic acid and an anionic phospholipid, a PEG-carboxylic acid and a fatty acid, or a fatty acid and an anionic phospholipid can be used in the pharmaceutical formulation of the invention. In yet another embodiment, three or more anionic excipients selected from a fatty acid, an anionic phospholipid, and a PEG-carboxylic acid are present in the pharmaceutical formulation. In particular embodiments, the combination of anionic excipients is selected from: stearic acid and mPEG-2,000-DSPE; DPPA and PEG-10,000-dicarboxylate; DPPA and PEG-3,350; DPPA; DPPA and mPEG-3,350 and mPEG-2,000-DSPE. In yet another embodiment, any of the anionic pospholipids described herein can be further combined with carboxymethyl cellulose (CMC), such as a combination of mPEG-2000-DSPE and CMC.

Cationic Peptides:

As used herein, "cationic polypeptide" means any polypeptide that carries a positive charge at a pH of about 5.0. The cationic polypeptide can include naturally occurring amino acid residues, non-naturally occurring amino acid residues or a mixture thereof. The positive charge of the cationic polypeptides results from a cationic functional group which is present either in the side chain of an amino acid of the polypeptide sequence, as part of the alpha amino group of an amino acid of the polypeptide sequence or both. The positive charge of the cationic polypeptide can also result from a cationic functional group ligated to the polypeptide at either of the termini of the peptide sequence or in the side chain of an amino acid in the sequence. There can be more than one cationic functional group present in the cationic polypeptide. For example, the cationic polypeptide can have 1, 2, 3, 4, 5, 6 or more cationic functional groups, each of which can provide a positive charge. Such functional groups include, for example, amino groups (primary, secondary or tertiary), quaternary ammonium groups, guanidino groups, amidino groups, pyridine groups, imidazole groups, phosphonium groups and sulfonium groups. In a particular embodiment, the cationic group is an amino group, a guanidino group or an imidazole group.

The cationic polypeptides of the invention may possess one or more chiral centers and so exist in a number of stereoisomeric forms. All stereoisomers and mixtures thereof are included in the scope of the present invention. Racemic compounds may either be separated using preparative HPLC and a column with a chiral stationary phase or resolved to yield individual enantiomers utilizing methods known to those skilled in the art. In addition, chiral intermediate compounds may be resolved and used to prepare chiral compounds of the invention.

The cationic polypeptides described herein may exist in one or more tautomeric forms. All tautomers and mixtures thereof are included in the scope of the present invention.

Cationic polypeptides suitable for use in the present invention include, but art not limited to the polypeptides categories and specific polypeptides listed below and the polypeptides represented by Formula I. The cationic polypeptides are pharmacologically active.

| LHRH (GnRH) agonists: | |
|---|---|
| Leuprolide: | Pyr-His-Trp-Ser-Tyr-D-Leu-Leu-Arg-Pro-NHEt (SEQ ID NO: 46) |
| Buserelin: | Pyr-His-Trp-Ser-Tyr-D-Ser(tBu)-Leu-Arg-Pro-NHEt (SEQ ID NO: 47): |
| Histrelin: | Pyr-His-Trp-Ser-Tyr-D-His(Bzl)-Leu-Arg-Pro-NHEt (SEQ ID NO: 48) |
| Goserelin: | Pyr-His-Trp-Ser-Tyr-D-Ser(tBu)-Leu-Arg-Pro-Azagly-$NH_2$ (SEQ ID NO: 49) |
| Deslorelin | Pyr-His-Trp-Ser-Tyr-D-Trp-Leu-Arg-Pro-NHEt (SEQ ID NO: 50) |
| Nafarelin | Pyr-His-Trp-Ser-Tyr-D-Nal(2)-Leu-Arg-Pro-Gly-$NH_2$ (SEQ ID NO: 51) |

| | |
|---|---|
| Triptorelin | Pyr-His-Trp-Ser-Tyr-D-Trp-Leu-Arg-Pro-Gly-NPh (SEQ ID NO: 52) |
| Avorelin | Pyr-His-Tip-Ser-Tyr-D-Tip(2-Me)-Leu-Arg-Pro-NHEt (SEQ ID NO: 53) |
| GnRH antagonists: | |
| Abarelix: | Ac-D-Nal(2)-D-Phe(4Cl)-D-Pal(3)-Ser-(Me)Tyr-D-Asn-Leu-Lys(iPr)-Pro-D-Ala-NH$_2$ (SEQ ID NO: 54) |
| Cetrorelix: | Ac-D-Nal(2)-D-Phe(4Cl)-D-Pal(3)-Ser-Tyr-D-Cit-Leu-Arg-Pro-D-Ala-NH$_2$ (SEQ ID NO: 55) |
| Degarelix: | Ac-D-Nal(2)-D-Phe(4Cl)-D-Pal(3)-Ser-Phe(4-(4S)-hexahydro-2,6-dioxo-4-pyrimidinyl(carbonyl)amino)-D-Phe(4-guanidino)-Leu-Lys(iPr)-Pro-D-Ala-NH$_2$ (SEQ ID NO: 56) |
| Ganirelix: | Ac-D-Nal(2)-D-Cpa(4)-D-Pal(3)-Ser-Tyr-D-Harg(Et)$_2$-Leu-Harg(Et)$_2$-Pro-D-Ala-NH$_2$ (SEQ ID NO: 57) |
| Somatostatin analogs: | |
| Octreotide | D-Phe-[Cys-Phe-D-Trp-Lys-Thr-Cys]-Thr-ol (SEQ ID NO: 58) |
| Lanreotide | D-Nal(2)-[Cys-Tyr-D-Trp-Lys-Val-Cys]-Thr-NH$_2$ (SEQ ID NO: 59) |
| Vapreotide | D-Phe-[Cys-Tyr-D-Trp-Lys-Val-Cys]-Trp-NH$_2$ (SEQ ID NO: 60) |
| Pasireotide (Signifor) | Cyclo[-(4R-4-(2-aminoethylcarbamoyloxy)-L-prolyl-L-phenylglycyl-D-tryptophyl-L-lysyl-4-O-benzyl-L-tyrosyl-L-phenylalanyl-] (SEQ ID NO: 60) |

Other Peptides:
Glucagon
Amylin
Pramlintide
Insulin
Glucagon-like peptide-1 (GLP-1)
a GLP-1 agonist
Exenatide
Parathyroid hormone (PTH)
Adrenocorticotropic hormone (ACTH)
Botulinum toxin
an amyloid peptide
Cholecystikinin
Calcitonin
a conotoxin
Prialt
a gastric inhibitory peptide
an insulin-like growth factor, including recombinantly manufactured IGF-1, such as Increlex
a growth hormone releasing factor
an anti-microbial factor
Glatiramer (Copaxone)
Hematide (peginesatide)
Nasiritide
ANF peptide
Angiotensin peptide
ACTH
Human Growth Hormone (hGH), including recombinantly manufactured hGH
Melanocortin
An opioid peptide
Dynorphin
Oxytocin
Oxytocin analog, including antagonists
Vasopressin and analogs and
Somatostatin and its analogs
Cationic Polypeptides of Formula I:

Cationic Polypeptides for use in the invention are those of Formula (I) or a pharmaceutically acceptable salt thereof:

$$R^1-A^1-A^2-A^3-A^4-A^5-A^6-A^7-A^8-R^2,$$

or a pharmaceutically acceptable salt thereof,
wherein:
$R^1$ is H, or a C1-C6 acyl;
$R^2$ is, $-NR^3R^4$, or $-OR^5$ wherein $R^3$, $R^4$, and $R^5$ are each independently is H or a C1-C6 alkyl;
$A^1$ is an amino acid residue selected from Arg, Lys, Orn, His, Nle, Phe, Val, Leu, Trp, Tyr, Ala, Ser, Thr, Gln, Asn, Asp, Glu, or TzAla; or
$A^1$ is a moiety selected from an optionally substituted C1-C12 alkyl, an optionally substituted C6-C18 aryl, an optionally substituted C5-C18 heteroaryl, an aralkyl wherein the aryl portion is an optionally substituted C6-C18 aryl, and the alkyl portion is an optionally substituted C1-C12 alkyl, or a heteroaralkyl, wherein the heteroaryl portion is an optionally substituted C5-C18 heteroaryl, and the alkyl portion is an optionally substituted C1-C12 alkyl;
$A^2$ and $A^8$ is each independently an amino acid residue selected from Cys, hCys, Pen, Asp, Glu, Lys, Orn, Dbu, or Dpr, wherein $A^2$ and $A^8$ are pairwise selected so as to be able to form covalent bond between their respective side chains;
$A^3$ is absent or is an amino acid residue selected from Ala, Tle, Val, Leu, Ile, Cha, Pro, Ser, Thr, Lys, Arg, His, Phe, Gln, Sar, Gly, Asn, or Aib;
$A^4$ is absent or an amino acid residue selected from Atc, Ala, QAla, Aib, Sar, Ser, Thr, Pro, Hyp, Asn, Gln, an optionally substituted His, Trp, Tyr, Lys, Arg, sChp, or residue X, where the X is an amino acid represented by the following structural formula

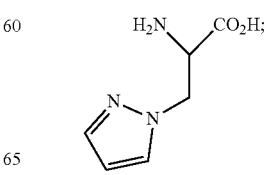

$A^5$ is an optionally substituted Phe, an optionally substituted 1-Nal, or an optionally substituted 2-Nal;

$A^6$ is Arg; and $A^7$ is Trp, wherein any amino acid residue is either in L- or in D-configuration.

In example embodiments, $A^3$ and $A^4$ are not both absent. Values and preferred values of the remainder of the variables are as defined above and below with respect to Formula (I).

In example embodiments, when $A^4$ is an amino acid, $A^3$ is not Aib or Gly. Values and preferred values of the remainder of the variables are as defined above with respect to Formula (I).

In example embodiments, when $A^4$ is His and $A^5$ is a D-Phe or 2-Nal, $A^3$ is not a D-amino acid or L-Ala. Values and preferred values of the remainder of the variables are as defined above with respect to Formula (I).

In example embodiments, when $A^2$ and $A^8$ each is selected from Cys, hCys or Pen, then: (a) when $A^4$ is absent, then $A^3$ is not L-His; (b) when $A^3$ is absent, then $A^4$ is not L-His; and (c) when $A^4$ is His, then $A^3$ is not Glu, Leu, or Lys. Values and preferred values of the remainder of the variables are as defined above with respect to Formula (I).

In example embodiments: 1) $A^3$ and $A^4$ are not both absent; 2) when $A^4$ is an amino acid, $A^3$ is not Aib or Gly; and 3) when $A^4$ is His and $A^5$ is a D-Phe or 2-Nal, $A^3$ is not a D-amino acid or L-Ala; 4) when $A^2$ and $A^8$ each is selected from Cys, hCys or Pen, then: (a) when $A^4$ is absent, then $A^3$ is not L-His; (b) when $A^3$ is absent, then $A^4$ is not L-His; and (c) when $A^4$ is His, then $A^3$ is not Glu, Leu, or Lys. Values and preferred values of the remainder of the variables are as defined above with respect to Formula (I).

In another embodiment, the polypeptides of Formula (I), $A^4$ is an L-amino acid. In yet other embodiments, $A^4$ is absent. Values and preferred values of the remainder of the variables are as defined above with respect to Formula (I).

In example embodiments, $A^5$ can be an optionally substituted 1-Nal or an optionally substituted 2-Nal, for example, an optionally substituted D-2-Nal. $A^5$ can be substituted at any of the five aromatic carbons with a substituent selected from F, Cl, Br, I, —CH$_3$, —OH, —CN, amine, —NO$_2$, or —OCH$_3$.

In a further embodiment, the polypeptides of Formula (I), $A^5$ is an optionally substituted D-Phe. $A^5$ can be substituted at any of the five aromatic carbons with a substituent selected from F, Cl, Br, I, —CH$_3$, —OH, —CN, amine, —NO$_2$, or —OCH$_3$. Suitable examples of $A^5$ include, but are not limited to, a D-amino acid residue selected from: Phe, Phe(2'-F), Phe(2'-Cl), Phe(2'-Br), Phe(2'-I), Phe(2'-CN), Phe(2'-CH$_3$), Phe(2'-OCH$_3$), Phe(2'-CF$_3$), Phe(2'-NO$_2$), Phe(3'-F), Phe(3'-Cl), Phe(3'-Br), Phe(3'-I), Phe(3'-CN), Phe(3'-CH$_3$), Phe(3'-OCH$_3$), Phe(3'-CF$_3$), Phe(3'-NO$_2$), Phe(4'-F), Phe(4'-Cl), Phe(4'-Br), Phe(4'-I), Phe(4'-CN), Phe(4'-CH$_3$), Phe(4'-OCH$_3$), Phe(4'-CF$_3$), Phe(4'-NO$_2$), Phe(4'-t-Bu), Phe(2',4'-diF), Phe(2',4'-diCl), Phe(2',4'-diBr), Phe(2',4'-diI), Phe(2',4'-di-CN), Phe(2',4'-di-CH$_3$), Phe(2',4'-di-OCH$_3$), Phe(3',4'-diF), Phe(3',4'-diCl), Phe(3',4'-diBr), Phe(3',4'-diI), Phe(3',4'-di-CN), Phe(3',4'-di-CH$_3$), Phe(3',4'-di-OCH$_3$), Phe(3',5'-diF), Phe(3',5'-diCl), Phe(3',5'-diBr), Phe(3',5'-diI), Phe(3', 5'-di-CN), Phe(3',5'-diCH$_3$), Phe(3',5'-di-OCH$_3$), or Phe(3',4',5'-triF). Values and preferred values of the remainder of the variables are as defined above with respect to Formula (I).

In a further embodiment, the polypeptides of Formula (I), $A^5$ is an optionally substituted D-2-Nal. $A^5$ can be substituted at any of the five aromatic carbons with a substituent selected from F, Cl, Br, I, —CH$_3$, —OH, —CN, amine, —NO$_2$, or —OCH$_3$.

In yet another embodiment, the polypeptides of Formula (I), $A^4$ is His, optionally substituted at any substitutable position with a substituent selected from F, Cl, Br, I, —CH$_3$, —OH, —CN, amine, —NO$_2$, benzyl or —OCH$_3$. Values and preferred values of the remainder of the variables are as defined above with respect to Formula (I).

In a particular embodiment, the compounds of the present invention are those polypeptides of Formula (I) that possess $EC_{50}$ with respect to MC4R from about 0.01 nM to about 10 nM, for example 0.01-3 nM, while possessing the ratio of $EC_{50}(MC1R)/EC_{50}(MC4R)$ of at least 10.

In another embodiment, the polypeptides of the present invention include a polypeptide represented by any one of the following structural formulas:

Ac-Arg-Cys-D-Ala-His-D-Phe-Arg-Trp-Cys-NH$_2$ (SEQ ID NO: 1)

Ac-Arg-Cys-D-Ala-His-D-Phe-Arg-Trp-Cys-OH (SEQ ID NO: 43)

H-Arg-Cys-D-Ala-His-D-Phe-Arg-Trp-Cys-OH (SEQ ID NO: 44)

H-Arg-Cys-D-Ala-His-D-Phe-Arg-Trp-Cys-NH$_2$ (SEQ ID NO: 45)

Ac-Arg-Cys-D-Ala-His-D-Phe(p-F)-Arg-Trp-Cys-NH$_2$ SEQ ID NO: 62

Ac-Arg-Cys-D-Ala-Pro-D-Phe-Arg-Trp-Cys-NH$_2$ SEQ ID NO: 14

Ac-Arg-Cys-D-Ala-Pro-D-Phe(p-F)-Arg-Trp-Cys-NH$_2$ SEQ ID NO: 15

Ac-Arg-Cys-D-Ala-Pro-D-Phe(p-F)-Arg-Trp-Cys-NH$_2$ SEQ ID NO: 15

Ac-Arg-Cys-D-Ala-Ser-D-Phe(p-F)-Arg-Trp-Cys-NH$_2$ SEQ ID NO: 63

Ac-Arg-Cys-D-Ala-Thr-D-Phe(p-F)-Arg-Trp-Cys-NH$_2$ SEQ ID NO: 64

Ac-Arg-Cys-D-Ala-Asn-D-Phe(p-F)-Arg-Trp-Cys-NH$_2$ SEQ ID NO: 10

Ac-Arg-Cys-D-Ala-Gln-D-Phe-Arg-Trp-Cys-NH$_2$ SEQ ID NO: 9

Ac-Arg-Cys-D-Ala-Trp-D-Phe-Arg-Trp-Cys-NH$_2$ SEQ ID NO: 8

Ac-Arg-Cys-D-Val-His-D-Phe-Arg-Trp-Cys-NH$_2$ SEQ ID NO: 5

Ac-Arg-Cys-D-Val-Gln-D-Phe-Arg-Trp-Cys-NH$_2$ SEQ ID NO: 34

Ac-Arg-Cys-D-Val-Pro-D-Phe-Arg-Trp-Cys-NH$_2$ (SEQ ID NO: 65) [Cys–Cys cyclized]

Ac-Arg-Cys-D-Ser-Pro-D-Phe-Arg-Trp-Cys-NH$_2$, (SEQ ID NO: 66) [Cys–Cys cyclized]

or a pharmaceutically acceptable salt thereof.

In yet another embodiment, the polypeptides of the present invention include any one of the following structural formulas:

Ac-Arg-hCys-D-Ala-D-Phe-Arg-Trp-Cys-NH$_2$ (SEQ ID NO: 21) [hCys–Cys cyclized]

Ac-Arg-hCys-D-Ala-D-Phe-Arg-Trp-Cys-NH$_2$ (SEQ ID NO: 20) [hCys–Cys cyclized]

Ac-Arg-hCys-D-Ala-D-Phe-Arg-Trp-Cys-OH (SEQ ID NO: 67) [hCys–Cys cyclized]

Ac-Arg-Cys-D-Ala-D-Phe-Arg-Trp-hCys-NH$_2$ (SEQ ID NO: 33) [Cys–hCys cyclized]

Ac-Arg-Pen-D-Ala-D-Phe-Arg-Trp-hCys-NH$_2$ (SEQ ID NO: 34) [Pen–hCys cyclized]

Ac-Arg-hCys-D-Ala-D-Phe(p-F)-Arg-Trp-Cys-NH$_2$ (SEQ ID NO: 68) [hCys–Cys cyclized]

Ac-Arg-hCys-Pro-D-Phe-Arg-Trp-Cys-NH$_2$ (SEQ ID NO: 36) [hCys–Cys cyclized]

Ac-Nle-hCys-Pro-D-Phe-Arg-Trp-Cys-NH$_2$ (SEQ ID NO: 69) [hCys–Cys cyclized]

Arg-hCys-Pro-D-Phe-Arg-Trp-Cys-NH$_2$ (SEQ ID NO: 70) [hCys–Cys cyclized]

CH$_3$—(CH$_2$)$_4$—CO—hCys-Pro-D-Phe-Arg-Trp-Cys-NH$_2$ (SEQ ID NO: 71) [hCys–Cys cyclized]

Benzyl-CO-hCys-Pro-D-Phe-Arg-Trp-Cys-NH$_2$, (SEQ ID NO: 72) [hCys–Cys cyclized]

or a pharmaceutically acceptable salt thereof.

In a further embodiment, the polypeptides of the present invention include the polypeptide represented by any one of the following structural formulas:

Ac-Arg-Asp-D-Ala-D-Phe-Arg-Trp-Dbu-NH$_2$ (SEQ ID NO: 73) [Asp–Dbu cyclized]

Ac-Arg-Glu-D-Ala-D-Phe-Arg-Trp-Dpr-NH$_2$ (SEQ ID NO: 74) [Glu–Dpr cyclized]

Ac-Arg-Glu-D-Ala-D-Phe-Arg-Trp-Dpr-NH$_2$ (SEQ ID NO: 75) [Glu–Dpr cyclized]

Ac-Arg-Dpr-D-Ala-D-Phe-Arg-Trp-Glu-NH$_2$ (SEQ ID NO: 76) [Dpr–Glu cyclized]

Ac-Arg-Dpr-D-Ala-D-Phe(4-F)-Arg-Trp-Glu-NH2 (SEQ ID NO: 77) [Dpr–Glu cyclized]

Ac-Arg-Dpr-D-Ala-D-Phe-Arg-Trp-Glu-NH$_2$ (SEQ ID NO: 78) [Dpr–Glu cyclized]

Ac-Arg-Dpr-Ala-D-Phe-Arg-Trp-Glu-OH (SEQ ID NO: 79) [Dpr–Glu cyclized]

Ac-Nle-Dpr-D-Ala-D-Phe-Arg-Trp-Glu-NH$_2$ (SEQ ID NO: 80) [Dpr–Glu cyclized]

Arg-Dpr-Ala-D-Phe-Arg-Trp-Glu-NH$_2$ (SEQ ID NO: 81) [Dpr–Glu cyclized]

CH$_3$—(CH$_2$)$_4$—CO—Dpr-Ala-D-Phe-Arg-Trp-Glu-NH$_2$ (SEQ ID NO: 82) [Dpr–Glu cyclized]

Benzyl-CO-Dpr-Ala-D-Phe-Arg-Trp-Glu-NH$_2$, (SEQ ID NO: 83) [Dpr–Glu cyclized]

or a pharmaceutically acceptable salt thereof.

In yet another embodiment, the polypeptides of the present invention include a polypeptide represented by formula (I), wherein $A^4$ is an amino acid residue selected from Atc, Ala, QAla, Aib, Sar, Ser, Thr, Pro, Hyp, Asn, Gln, a substituted His, Trp, Tyr, Lys, Arg, sChp, or residue X. Examples of such peptides include peptides represented by any one of the following structural formulas:

```
                                     (SEQ ID NO: 6)
        Ac-Arg-cyclo[Cys-D-Ala-His (3-Me)-D-Phe-Arg-Trp-Cys]-NH2;

(SEQ ID NO: 7)
        Ac-Arg-cyclo[Cys-D-Ala-His (1-Me)-D-Phe-Arg-Trp-Cys]-NH2;

(SEQ ID NO: 8)
        Ac-Arg-cyclo[Cys-D-Ala-Trp-

D-Phe-Arg-Trp-Cys]-NH2;

(SEQ ID NO: 9)
        Ac-Arg-cyclo[Cys-D-Ala-Gln-

D-Phe-Arg-Trp-Cys]-NH2;

(SEQ ID NO: 10)
        Ac-Arg-cyclo[Cys-D-Ala-Asn-

D-Phe-Arg-Trp-Cys]-NH2;

(SEQ ID NO: 11)
        Ac-Arg-cyclo[Cys-D-Ala-Arg-

D-Phe-Arg-Trp-Cys]-NH;

(SEQ ID NO: 12)
        Ac-Arg-cyclo[Cys-D-Ala-Tyr-

D-Phe-Arg-Trp-Cys]-NH2;
```

Ac-Arg-cyclo[Cys-D-Ala-D-Pro-D-Phe-Arg-Trp-Cys]-NH$_2$; (SEQ ID NO: 13)

Ac-Arg-cyclo[Cys-D-Ala-Pro-D-Phe-Arg-Trp-Cys]-NH$_2$; (SEQ ID NO: 14)

Ac-Arg-cyclo[Cys-D-Ala-Pro-D-Phe(p-F)-Arg-Trp-Cys]-NH$_2$; (SEQ ID NO: 15)

Ac-Arg-cyclo[Cys-D-Ala-Atc-D-Phe-Arg-Trp-Cys]-NH$_2$; (SEQ ID NO: 16)

Ac-Arg-cyclo[Cys-D-Ala-QAla-D-Phe-Arg-Trp-Cys]-NH$_2$; (SEQ ID NO: 17)

Ac-Arg-cyclo[Cys-D-Ala-sChp-D-Phe-Arg-Trp-Cys]-NH$_2$; or (SEQ ID NO: 18)

Ac-Arg-cyclo[Cys-D-Ala-X-D-Phe-Arg-Trp-Cys]-NH$_2$, (SEQ ID NO: 19)

or a pharmaceutically acceptable salt thereof.

In example embodiments, the polypeptides of the present invention include a polypeptide represented by any one of the following structural formulas:

Ac-Arg-cyclo[hCys-Ala-D-Phe-Arg-Trp-Cys]-NH$_2$; (SEQ ID NO: 20)

Ac-Arg-cyclo[hCys-D-Ala-D-Phe-Arg-Trp-Cys]-NH$_2$; (SEQ ID NO: 21)

Ac-Arg-cyclo[hCys-D-Ala-D-Phe-Arg-Trp-Pen]-NH$_2$; (SEQ ID NO: 22)

Ac-Arg-cyclo[Glu-D-Ala-D-Phe-Arg-Trp-Dpr]-NH$_2$; (SEQ ID NO: 23)

Ac-Arg-cyclo[Glu-Ala-D-Phe-Arg-Trp-Dpr]-NH$_2$; (SEQ ID NO: 24)

Ac-Arg-cyclo[hCys-Aib-D-Phe-Arg-Trp-Cys]-NH$_2$; (SEQ ID NO: 25)

Ac-Arg-cyclo[hCys-Sar-D-Phe-Arg-Trp-Cys]-NH$_2$; (SEQ ID NO: 26)

Ac-Arg-cyclo[hCys-Val-D-Phe-Arg-Trp-Cys]-NH$_2$; (SEQ ID NO: 27)

Ac-Arg-cyclo[hCys-D-Val-D-Phe-Arg-Trp-Cys]-NH$_2$; (SEQ ID NO: 28)

Ac-Arg-cyclo[hCys-Gln-D-Phe-Arg-Trp-Cys]-NH$_2$; (SEQ ID NO: 29)

Ac-Arg-cyclo[hCys-D-Gln-D-Phe-Arg-Trp-Cys]-NH$_2$; (SEQ ID NO: 30)

Ac-Arg-cyclo[hCys-Ala-D-Phe-Arg-Trp-Pen]-NH$_2$; (SEQ ID NO: 31)

Ac-Arg-cyclo[D-Pen-D-Ala-D-Phe-Arg-Trp-hCys]-NH$_2$; (SEQ ID NO: 32)

Ac-Arg-cyclo[Cys-D-Ala-D-Phe-Arg-Trp-hCys]-NH$_2$; (SEQ ID NO: 33)

Ac-Arg-cyclo[Pen-D-Ala-D-Phe-Arg-Trp-hCys]-NH$_2$; (SEQ ID NO: 34)

Ac-Arg-cyclo[D-hCys-D-Ala-D-Phe-Arg-Trp-Cys]-NH$_2$; (SEQ ID NO: 35)

Ac-Arg-cyclo[hCys-Pro-D-Phe-Arg-Trp-Cys]-NH$_2$; or (SEQ ID NO: 36)

Ac-Arg-cyclo[hCys-D-Pro-D-Phe-Arg-Trp-Cys]-NH$_2$, (SEQ ID NO: 37)

or a pharmaceutically acceptable salt thereof.

In another embodiment, the polypeptides of the present invention include polypeptides represented by formula (I), wherein A$^3$ is an amino acid residue selected from Tle, Val, Leu, Ile, Cha, Pro, Ser, Thr, Lys, Arg, His, Phe, Gln, Sar, Gly, Asn, or Aib; and A$^4$ is an amino acid residue selected from Atc, Ala, QAla, Aib, Sar, Ser, Thr, Pro, Hyp, Asn, Gln, a substituted His, Trp, Tyr, Lys, Arg, sChp, or residue X. Examples of such polypeptides are polypeptides represented by any one of the following structural formulas:

Ac-Arg-cyclo[Cys-Val-Gln-D-Phe-Arg-Trp-Cys]-NH$_2$; (SEQ ID NO: 38)

```
                                               (SEQ ID NO: 39)
Ac-Arg-cyclo[Cys-D-Val-Gln-D-

Phe-Arg-Trp-Cys]-NH2;
or
                                               (SEQ ID NO: 40)
Ac-Arg-cyclo[Cys-D-Val-His (1-Me)-D-Phe-Arg-Trp- Cys]-NH2,
``` or a pharmaceutically acceptable salt thereof.

In a further embodiment, the polypeptides of the present invention include a polypeptide represented by any one of the following structural formulas:

```
                                               (SEQ ID NO: 41)
Ac-TzAla-cyclo[Cys-Ala-Gln-D-

Phe-Arg-Trp-Cys]-NH2;
or
                                               (SEQ ID NO: 42)
Ac-Glu-cyclo[Cys-Ala-His-D-

Phe-Arg-Trp-Cys]-NH2,
``` or a pharmaceutically acceptable salt thereof.

In yet another embodiment, the polypeptides of the present invention include a polypeptide represented by any one of the following structural formulas:

```
                                               (SEQ ID NO: 7)
Ac-Arg-cyclo[Cys-D-Ala-His(1-Me)-

D-Phe-Arg-Trp-Cys]-NH2
                                               (SEQ ID NO: 9)
Ac-Arg-cyclo[Cys-D-Ala-Gln-D-Phe- Arg-Trp-Cys]-NH2
                                               (SEQ ID NO: 10)
Ac-Arg-cyclo[Cys-D-Ala-Asn-D-Phe- Arg-Trp-Cys]-NH2
``` or a pharmaceutically acceptable salt thereof.

In a further embodiment, the polypeptides of the present invention include a polypeptide represented by any one of the following structural formulas:

```
                                               (SEQ ID NO: 2)
Ac-Arg-cyclo[Cys-D-Leu-His-D-

Phe-Arg-Trp-Cys]-NH2;
                                               (SEQ ID NO: 3)
Ac-Arg-cyclo[Cys-D-Ile-His-D-

Phe-Arg-Trp-Cys]-NH2;
                                               (SEQ ID NO: 4)
Ac-Arg-cyclo[Cys-D-Tle-His-D-

Phe-Arg-Trp-Cys]-NH2;
                                               (SEQ ID NO: 5)
Ac-Arg-cyclo[Cys-D-Val-His-D-

Phe-Arg-Trp-Cys]-NH2,
``` or a pharmaceutically acceptable salt thereof.

In a further embodiment, the polypeptides of the present invention include a polypeptide represented by any one of the following structural formulas:

```
                                               (SEQ ID NO: 84)
Ac-Arg-cyclo[Cys-D-Ala-His(1-Me)-

D-2-Nal-Arg-Trp-Cys]-NH2;
                                               (SEQ ID NO: 85)
Ac-Arg-cyclo[Cys-D-Ala-Gln-D-2-

Nal-Arg-Trp-Cys]-NH2;
or
                                               (SEQ ID NO: 86)
Ac-Arg-cyclo[Cys-D-Ala-Asn-D-2-

Nal-Arg-Trp-Cys]-NH2,
``` or a pharmaceutically acceptable salt thereof. In a further eptides of the present invention include a polypeptide represented by any one of the following structural formulas:

```
                                               (SEQ ID NO: 87)
Ac-Arg-cyclo[Cys-D-Ala-His(1-Me)-

D-Phe-Arg-Trp-Cys]-OH;
                                               (SEQ ID NO: 88)
Ac-Arg-cyclo[Cys-D-Ala-Gln-D-Phe- Arg-Trp-Cys]-OH;
or
                                               (SEQ ID NO: 89)
Ac-Arg-cyclo[Cys-D-Ala-Asn-D-Phe- Arg-Trp-Cys]-OH,
``` or a pharmaceutically acceptable salt thereof.

In an alternative embodiment, the cationic peptides for use in the invention are those of Formula (II) or a pharmaceutically acceptable salt thereof:

An isolated polypeptide of the following structural Formula (II):

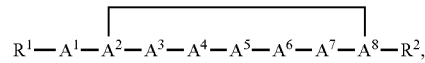

or a pharmaceutically acceptable salt thereof, wherein:

$R^1$ is —H, or a C1-C6 acyl;

$R^2$ is —$NR^3R^4$, or —$OR^5$ wherein $R^3$, $R^4$, and $R^5$ are each independently is H or a C1-C6 alkyl;

$A^1$ is absent; or $A^1$ is an amino acid residue selected from Arg, Lys, Orn, His, Nle, Phe, Val, Leu, Trp, Tyr, Ala, Ser, Thr, Gln, Asn, Asp, Glu, or TzAla; or $A^1$ is a moiety selected from an optionally substituted C1-C12 alkyl, an optionally substituted C6-C18 aryl, an optionally substituted C5-C18 heteroaryl, an aralkyl wherein the aryl portion is an optionally substituted C6-C18 aryl, and the alkyl portion is an optionally substituted C1-C12 alkyl, or a heteroaralkyl, wherein the heteroaryl portion is an optionally substituted C5-C18 heteroaryl, and the alkyl portion is an optionally substituted C1-C12 alkyl;

$A^2$ and $A^8$ is each independently an amino acid residue selected from Cys, hCys, Pen, Asp, Glu, Lys, Orn, Dbu, or Dpr, wherein $A^2$ and $A^8$ are pairwise selected so as to be able to form covalent bond between their respective side chains;

$A^3$ is absent or is an amino acid residue selected from Ala, Tle, Val, Leu, Ile, Cha, Pro, Ser, Thr, Lys, Arg, His, Phe, Gln, Sar, Gly, Asn, Aib, or residue Y, wherein Y is an amino acid selected from amino acids represented by the following structural formulas

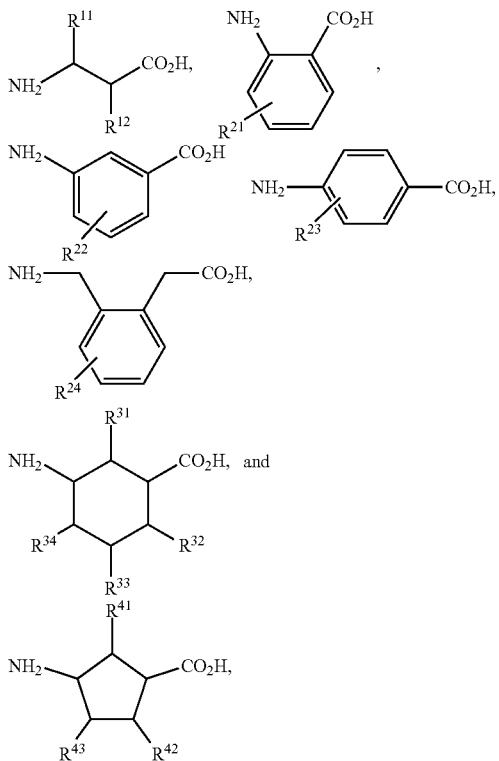

wherein:
$R^{11}$ and $R^{12}$, each independently, is H, —CH$_3$, phenyl, or benzyl;
$R^{21}$, $R^{22}$, $R^{23}$ and $R^{24}$, each independently is H, —CH$_3$, —CF$_3$, phenyl, benzyl, F, Cl, Br, I, —OCH$_3$, or —OH;
$R^{31}$, $R^{32}$, $R^{33}$, $R^{34}$, $R^{41}$, $R^{42}$ and $R^{43}$, each independently is H, —CH$_3$, —CF$_3$, phenyl, benzyl, F, Cl, Br, I, —OCH$_3$, or —OH;

$A^4$ is absent or is an amino acid residue selected from Atc, Ala, QAla, Aib, Sar, Ser, Thr, Pro, Hyp, Asn, Gln, an optionally substituted His, Trp, Tyr, Lys, Arg, sChp, or residue X, where the X is an amino acid selected from amino acids represented by the following structural formulas:

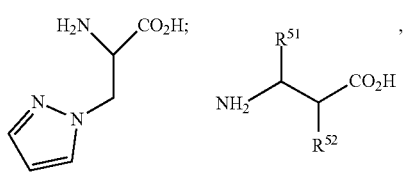

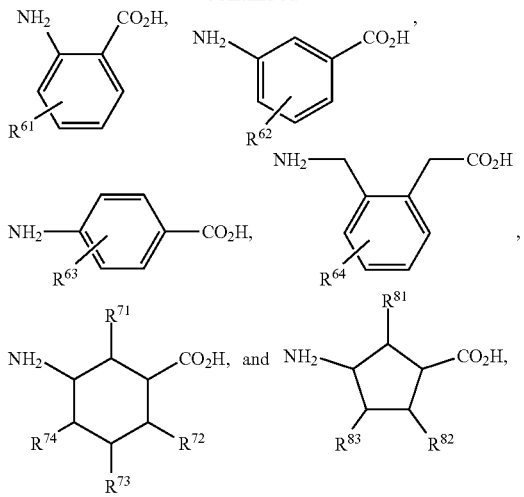

wherein:
$R^{51}$ and $R^{52}$, each independently, is H, —CH$_3$, phenyl, or benzyl;
$R^{61}$, $R^{62}$, $R^{63}$, and $R^{64}$, each independently is H, —CH$_3$, —CF$_3$, phenyl, benzyl, F, Cl, Br, I, —OCH$_3$, or —OH;
$R^{71}$, $R^{72}$, $R^{73}$, $R^{74}$, $R^{81}$, $R^{82}$, and $R^{83}$, each independently is H, —CH$_3$, —CF$_3$, phenyl, benzyl, F, Cl, Br, I, —OCH$_3$, or —OH;

$A^5$ is an optionally substituted Phe, an optionally substituted 1-Nal, or an optionally substituted 2-Nal;
$A^6$ is Arg; and
$A^7$ is Trp,
wherein any amino acid residue is either in L- or in D-configuration.

In example embodiments, $A^3$ and $A^4$, each independently, is a residue of an amino acid selected from amino acids represented by the following structural formulas:

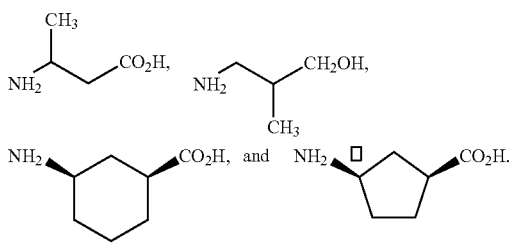

Values and preferred values of the remainder of the variables are as defined herein with respect to Formula (I).

"Alkyl" used alone or as part of a larger moiety such as "hydroxyalkyl", "alkoxyalkyl", "alkylamine" refers to a straight or branched, saturated aliphatic group having the specified number of carbons, typically having 1 to 12 carbon atoms. More particularly, the aliphatic group may have 1 to 8, 1 to 6, or 1 to 4 carbon atoms. This term is exemplified by groups such as methyl, ethyl, n-propyl, isopropyl, n-butyl, isobutyl, tert-butyl, n-hexyl, and the like.

"Haloalkyl" refers to an alkyl group substituted with one or more halogen atoms.

"Halogen" and "halo" refer to fluoro, chloro, bromo or iodo.

"Cyano" refers to the group —CN.
"Ph" refers to a phenyl group.
"Carbonyl" refers to a divalent —C(O)— group.

"Aryl" used alone or as part of a larger moiety as in "aralkyl" refers to an aromatic carbocyclic group of from 6 to 18 carbon atoms having a single ring or multiple condensed rings. The term "aryl" also includes aromatic carbocycle(s) fused to cycloalkyl or heterocycloalkyl groups. Examples of aryl groups include phenyl, benzo[d][1,3]dioxole, naphthyl, phenanthrenyl, and the like.

"Aryloxy" refers to an —OAr group, wherein O is an oxygen atom and Ar is an aryl group as defined above.

"Aralkyl" refers to an alkyl having at least one alkyl hydrogen atom replaced with an aryl moiety, such as benzyl, —(CH$_2$)$_2$phenyl, —(CH$_2$)$_3$phenyl, —CH(phenyl)$_2$, and the like.

"Heteroaryl" used alone or a part of a larger moiety as in "heteroaralkyl" refers to a 5 to 18 membered monocyclic, bicyclic or tricyclic heteroaromatic ring system, containing one to four ring heteroatoms independently selected from nitrogen, oxygen and sulfur. The term "heteroaryl" also includes heteroaromatic ring(s) fused to cycloalkyl or heterocycloalkyl groups. Particular examples of heteroaryl groups include optionally substituted pyridyl, pyrrolyl, pyrimidinyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxa-zolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 1,2,3,4-tetrahydroquinolyl, 1,2,3,4-tetrahydroisoquinolyl, purinyl, pteridinyl, carbazolyl, xanthenyl, benzoquinolyl, and the like.

"Heteroaralkyl" refers to an alkyl having at least one alkyl hydrogen atom replaced with a heteroaryl moiety, such as —CH$_2$-pyridinyl, —CH$_2$-pyrimidinyl, and the like.

"Alkoxy" refers to the group —O—R where R is "alkyl", "cycloalkyl", "alkenyl", or "alkynyl". Examples of alkoxy groups include for example, methoxy, ethoxy, ethenoxy, and the like.

"Hydroxyalkyl" and "alkoxyalkyl" are alkyl groups substituted with hydroxyl and alkoxy, respectively.

"Amino" means —NH$_2$; "alkylamine" and "dialkylamine" mean —NHR and —NR$_2$, respectively, wherein R is an alkyl group. "Cycloalkylamine" and "dicycloalkylamine" mean —NHR and —NR$_2$, respectively, wherein R is a cycloalkyl group. "Cycloalkylalkylamine" means —NHR wherein R is a cycloalkylalkyl group. "[Cycloalkylalkyl][alkyl]amine" means —N(R)$_2$ wherein one R is cycloalkylalkyl and the other R is alkyl.

"Acyl" refers to R"—C(O)—, where R$^{11}$ is H, alkyl, substituted alkyl, heteroalkyl, substituted heteroalkyl, alkenyl, substituted alkenyl, aryl, alkylaryl, or substituted alklyaryl, and is indicated in the general formula of a particular embodiment as "Ac".

Suitable substituents for "alkyl", "aryl", or "heteroaryl", etc., are those which will form a stable compound of the invention. Examples of suitable substituents are those selected from the group consisting of halogen, —CN, —OH, —NH$_2$, (C1-C4)alkyl, (C1-C4)haloalkyl, aryl, heteroaryl, (C3-C7)cycloalkyl, (5-7 membered) heterocycloalkyl, —NH(C1-C6)alkyl, —N((C1-C6)alkyl)$_2$, (C1-C6)alkoxy, (C1-C6)alkoxycarbonyl, —CONH$_2$, —OCONH$_2$, —NHCONH$_2$, —N(C1-C6)alkylCONH$_2$, —N(C1-C6)alkylCONH(C1-C6)alkyl, —NHCONH(C1-C6)alkyl, —NHCON((C1-C6)alkyl)$_2$, —N(C1-C6)alkylCON((C1-C6)alkyl)$_2$, —NHC(S)NH$_2$, —N(C1-C6)alkylC(S)NH$_2$, —N(C1-C6)alkylC(S)NH(C1-C6)alkyl, —NHC(S)NH(C1-C6)alkyl, —NHC(S)N((C1-C6)alkyl)$_2$, —N(C1-C6)alkylC(S)N((C1-C6)alkyl)$_2$, —CONH(C1-C6)alkyl, —OCONH(C1-C6)alkyl —CON((C1-C6)alkyl)$_2$, —C(S)(C1-C6)alkyl, —S(O)$_p$(C1-C6)alkyl, —S(O)$_p$NH$_2$, —S(O)$_p$NH(C1-C6)alkyl, —S(O)$_p$N((C1-C6)alkyl)$_2$, —CO(C1-C6)alkyl, —OCO(C1-C6)alkyl, —C(O)O(C1-C6)alkyl, —OC(O)O(C1-C6)alkyl, —C(O)H or —CO$_2$H. More particularly, the substituents are selected from halogen, —CN, —OH, —NH$_2$, (C1-C4)alkyl, (C1-C4)haloalkyl, (C1-C4)alkoxy, phenyl, and (C3-C7)cycloalkyl. Within the framework of this invention, said "substitution" is also meant to encompass situations where a hydrogen atom is replaced with a deuterium atom. p is an integer with a value of 1 or 2.

Suitable substituents on a substituted Phe include one to five substituents on any aromatic carbons, the substituents being selected from F, Cl, Br, I, —CH$_3$, —OH, —CN, amine, —NO$_2$, or —OCH$_3$. Examples include Phe(2'-F), Phe(2'-Cl), Phe(2'-Br), Phe(2'-I), Phe(2'-CN), Phe(2'-CH$_3$), Phe(2'-OCH$_3$), Phe(2'-CF$_3$), Phe(2'-NO$_2$), Phe(3'-F), Phe(3'-Cl), Phe(3'-Br), Phe(3'-I), Phe(3'-CN), Phe(3'-CH$_3$), Phe(3'-OCH$_3$), Phe(3'-CF$_3$), Phe(3'-NO$_2$), Phe(4'-F), Phe(4'-Cl), Phe(4'-Br), Phe(4'-I), Phe(4'-CN), Phe(4'-CH$_3$), Phe(4'-OCH$_3$), Phe(4'-CF$_3$), Phe(4'-NO$_2$), Phe(4'-t-Bu), Phe(2',4'-diF), Phe(2',4'-diCl), Phe(2',4'-diBr), Phe(2',4'-diI), Phe(2',4'-di-CN), Phe(2',4'-di-CH$_3$), Phe(2',4'-di-OCH$_3$), Phe(3',4'-diF), Phe(3',4'-diCl), Phe(3',4'-diBr), Phe(3',4'-diI), Phe(3',4'-di-CN), Phe(3',4'-di-CH$_3$), Phe(3',4'-di-OCH$_3$), Phe(3',5'-diF), Phe(3',5'-diCl), Phe(3',5'-diBr), Phe(3',5'-diI), Phe(3',5'-di-CN), Phe(3',5'-diCH$_3$), Phe(3',5'-di-OCH$_3$), or Phe(3',4',5'-triF).

Suitable substituents on a substituted His include one to three substituents on any substitutable ring atom, the substituents being selected from F, Cl, Br, I, —CH$_3$, —OH, —CN, amine, —NO$_2$, benzyl, or —OCH$_3$. Examples include 1-Methyl-Histidine and 3-Methyl-Histidine.

Designation "(amino acid)$_n$" means that an amino acid is repeated n times. For example, designation "(Pro)$_2$" or "(Arg)$_3$" mean that proline or arginine residues are repeated, respectively, two or three times.

Pharmaceutically acceptable salts of the compounds disclosed herein are included in the present invention. For example, an acid salt of a compound containing an amine or other basic group can be obtained by reacting the compound with a suitable organic or inorganic acid, resulting in pharmaceutically acceptable anionic salt forms. Examples of anionic salts include the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate, triethiodide, and trifluoroacetate salts.

Salts of the compounds containing an acidic functional group can be prepared by reacting with a suitable base. Such a pharmaceutically acceptable salt can be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bisdehydroabietylamine, glucamine, N-methylglucamine, collidine, quinine, quinoline, and basic amino acids such as lysine and arginine.

Pharmaceutical Compositions

The invention further relates to a pharmaceutical composition comprising an ionic complex comprising: a cationic polypeptide; an anionic excipient selected from: a PEG-carboxylic acid; a fatty acid having 10 or more carbon atoms; an anionic phospholipid; and a combination thereof; and a pharmaceutically acceptable carrier. In one embodiment, the pharmaceutical composition further comprises an additional excipient as described below (e.g., carboxymethylcellulose (CMC)). For example, any of the anionic pospholipids described herein can be further combined with carboxymethyl cellulose (CMC), such as a combination of mPEG-200-DSPE and CMC.

The ratio of concentrations of the cationic peptide and an anionic excipient is determined in terms of molar ratio of a cationic charge in the polypeptide to the charge of the anionic excipient. For example, in terms of one positive charge in the polypeptide, the amount of the anionic excipient could range from 1:1 to 1:10. For additional positive charges in the polypeptide, the ratio of anionic excipient may be adjusted accordingly. By varying the amount of anionic excipient within this ratio, the in vivo release characteristic of a polypeptide may be modulated. A higher ratio typically can yield a composition that provides for a slower release of the polypeptide from the site of administration than the one with lower ratio.

The term "pharmaceutically acceptable carrier" in the pharmaceutical composition of the invention, means a biocompatible, polar liquid. The polar nature of liquid assists in maintaining the complex in its ionic form. Biocompatible, polar liquids include, but are not limited to, a PEG (polyethylene glycol, e.g., a polyethylene glycol having an average molecular weight of 100 to 500), polyol (e.g., propylene glycol (PG), tripropylene glycol, glycerol), ethanol, benzyl alcohol, DMSO, NMP, DMF, water, pH buffered solutions, and mixtures thereof. It is understood that additional diluents and additional excipients as described below can be included in the pharmaceutical composition.

In certain embodiments, the pharmaceutical composition of the invention forms a drug depot when injected into a subject. In some embodiments, the drug depot slowly releases the active compound over time following injection into a subject. In one aspect, at least a portion of the pharmaceutical composition precipitates to form a drug depot and releases the pharmacologically active compound over time when injected into the subject. In some embodiments, the compositions of the invention allow for high concentrations of polypeptide of structural Formula (I) appropriate for creating drug depots for sustained steady state release of therapeutically effective levels of the polypeptide in vivo. An example range of concentrations of polypeptide of structural Formula (I) in formulation is from about 0.001 mg/mL to about 100 mg/mL.

The pharmaceutical composition of the invention can include additional excipients (also referred to herein as co-excipients). Suitable examples of additional excipients include pH stabilizing buffers, preservatives, surfactants, stabilizers, anti-oxidants, tonicity agents and ionic and non-ionic polymers as defined herein.

Such a co-excipient can be added to aid in the formation of homogenous suspensions and dispersion of the ionic complex or even the hydrophobic class of anionic excipient, for example, a lipid or fatty acid. The class of co-excipients include the dispersing and emulsifying agents such as lecithin, soybean oil, castor oil, migliol, polyethylene glycol (MW ranging 200 to 5,000), methyl cellulose, and carboxymethyl cellulose.

As used herein, the term "surfactant" refers to a surface-active agent or a substance that tends to reduce the surface tension of the liquid in which it is dissolved. Suitable surfactants include polysorbates, poloxamers, Triton, sodium dodecyl sulfate, sodium lauryl sulfate, and betaines. For example, surfactants include polyoxyethylene (20) sorbitan monolaurate (Tween® 20, e.g. from Sigma-Aldrich), polyoxyethylene (20) sorbitan monopalmitate (Tween® 40), polyoxyethylene (20) sorbitan monooleate (Tween® 80), poloxamer 188, polyoxyethylene-polyoxypropylene block copolymer (Pluronic® F-68, e.g. from Sigma-Aldrich), polyethyleneglycol 660-12-hydroxystearate (Solutol® HS 15, BASF), cocamidopropyl betaine, linoleyl betaine, myristyl betaine, cetyl betaine, polyethoxylated castor oil (Cremophor®, now Kolliphor BASF), and lecithin.

As used herein, the term "tonicity agents" refers to substances used to modulate the tonicity of a formulation. Tonicity in general relates to the osmotic pressure of a solution usually relative to that of human blood serum. The formulation can be hypotonic, isotonic or hypertonic. A formulation is typically preferably isotonic. An isotonic formulation is liquid or liquid reconstituted from a solid form, e.g. from a lyophilized form and denotes a solution having the same tonicity as some other solution with which it is compared, such as physiologic salt solution and the blood serum. Tonicity agents can help to reduce pain and irritation in a subject upon injection. Suitable tonicity agents include dextrose, glycerin, hydroxyethyl starch, lactose, mannitol (e.g., D-mannitol), raffinose, sorbitol, sucrose, trehalose, sodium chloride, calcium chloride, magnesium chloride, and potassium chloride.

The term "buffer" as used herein denotes an excipient which stabilizes the pH of the pharmaceutical composition. Suitable buffers are well known in the art and can be found in the literature. Examples of suitable buffers include histidine-buffers, citrate-buffers, succinate-buffers, acetate-buffers and phosphate-buffers or mixtures thereof. Most preferred buffers comprise citrate, L-histidine or mixtures of L-histidine and L-histidine hydrochloride. Other preferred buffer is acetate buffer. Independently from the buffer used, the pH can be adjusted with an acid or a base known in the art, e.g. hydrochloric acid, acetic acid, phosphoric acid, sulfuric acid and citric acid, sodium hydroxide and potassium hydroxide.

The ionic polymers suitable for use as an additional excipient include ionic carboxymethyl cellulose (CMC), hyaluronic acid, poly(glutamic acid), poly(aspartic acid), poly(glutamic acid-co-glycine), poly(aspartic acid-co-glycine), poly(glutamic acid-co-alanine), poly(aspartic acid-co-alanine), starch glycolate, polygalacturonic acid, poly(acrylic acid), carrageenan and alginic acid.

In certain embodiments, the CMC has an average molecular weight range of about 5,000 to about 700,000. In some embodiments, methyl cellulose and carboxymethyl cellulose may help modulate the viscosity of the ionic complex to enhance a slow releasing drug depot of the active compound and release the active compound over time when injected into a subject.

The non-ionic polymers suitable for use as an additional excipient include polyethylene glycol having a MW ranging from about 100 to 100,000, for example from about 100 to about 60,000, such as from about 100 to about 10,000 such as from about 100 to about 5000. Other weight ranges include from about 200 to about 60,000. Suitable examples of neutral polymers include PEG-3350 and PEG-3400. The polyethylene glycol polymers include both PEG and mPEG, which can be either monomethoxy or dimethoxy. PEG can be structurally depicted as follows:

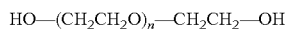

with the value of "n" varying with molecular weight. For example, the PEG-3500 acid has a molecular weight of 3,500.

The mPEG can have on of the following two structures:
Monomethoxy mPEG: $CH_3O—(CH_2CH_2O)_n—CH_2CH_2—OH$. One end capped as methoxy group and the other end has a hydroxyl (OH) group.
Di-methoxy mPEG: $CH_3O—(CH_2CH_2O)_n—CH_2CH_2—OCH_3$. Both the ends are capped as methoxy groups Diluents can be added to pharmaceutical compositions of the invention to further dissolve or suspend the ionic complex of the invention. Diluents include biologically compatible materials such as non aqueous injectable liquids of low viscosity. Non aqueous injectable liquids of low viscosity include castor oil, vegetable oil, mineral oil, squalene, monoglycerides, diglycerides, triglycerides, or mixtures of glycerides. In some embodiments, the diluent is Miglyol® 812 (from Sasol GmbH, Germany), Labrafac® WL1349 (caprylic acid triglyceride from Gattefosse company, France), or Lipoid MCT (from Lipoid company, Germany) and the like.

As used herein, a "drug depot" refers to the precipitate that can form following injection of the pharmaceutical composition of the invention. The compositions can form a slow releasing drug depot of the active compound and release the active compound over time when injected into a subject. In one aspect, at least a portion of the composition precipitates and releases the pharmacologically active compound over time when injected into the subject.

A "preservative" is a compound which can be added to the formulation to reduce bacterial activity or undesirable chemical changes in the formulations. Examples of preservatives include benzyl alcohol, ethanol, methanol, isopropanol, butyl paraben, ethyl paraben, methyl paraben, propyl paraben, cathechol, 2-chlorophenol, m-cresol, phenol, resorcinol, xylitol, 2,6-dimethylcyclohexanol, 2-methyl-2,4-pentadiol, polyvinylpyrrolidone, benzethonium chloride, merthiolate (thimersosal), benzoic acid, benzalkonium chloride, chlorobutanol, sodium benzoate, sodium propionate, and cetylpyridinium chloride.

Methods of Treatment

The invention relates to the use of the the ionic complex and pharmaceuctical composition comprising same to treat a subject suffering from a disease or disorder that is responsive to the pharmacological activity possessed by the cationic polypeptide of the ionic complex. In one embodiment, the disorder to be treated is responsive to the modulation of MC4R in a subject in need of treatment. The method comprises administering to the subject an effective amount of an ionic complex comprising as the cationic polypeptide an MC4R modulator such as those described in Formula I herein. In a particular embodiment, the disorder responsive to modulation of the MC4R includes type 1 diabetes, type 2 diabetes, obesity, insulin resistance, metabolic syndrome, male erectile dysfunction, female sexual disorder, non-alcoholic fatty liver disease, non-alcoholic steatohepatitis, disorders of substance abuse, including alcoholism feeding disorders, cachexia, inflammation and anxiety.

In certain embodiments, the ionic complex and pharmaceutical composition comprising a cationic polypeptide of Formula I can possess higher selectivity and potency for the MC4R and melanocortin-3 receptor (MC3R) when compared to melanocortin-1 receptor (MC1R). The ionic complex and pharmaceutical composition of the present invention can reduce or eliminate such undesirable side effects as increase in blood pressure effects, increase in heart rate, undesired effects on sexual arousal, and increase in skin pigmentation.

As used herein, the phrase "a disorder responsive to the modulation of the melanocortin-4 receptor" refers to any disorder that can be treated by activation (agonizing) or inhibition of MC4R. Examples of such disorders will be described in detail below.

As used herein, the term "modulator" refers to compounds which interact with the target receptor and affects its biological function. Examples of modulators include full agonists, partial agonists, neutral antagonists, and inverse agonists.

As used herein, the term "agonist" refers to any chemical compound, either naturally occurring or synthetic, that, upon interacting with (e.g., binding to) its target, here, MC4R, raises the signaling activity of MC4R above its basal level. An agonist can be a superagonist (i.e. a compound that is capable of producing a greater maximal response than the endogenous agonist for the target receptor, and thus has an efficacy of more than 100%), a full agonist (i.e. a compound that elicits a maximal response following receptor occupation and activation) or a partial agonist (i.e. a compounds that can activate receptors but are unable to elicit the maximal response of the receptor system). Examples of MC4R agonists will be described in detail below.

As used herein, the term "antagonist" refers to any chemical compound, that, upon interacting with (e.g., binding to) its target, here, MC4R, blocks, in a dose dependent manner, the signaling activity of an agonist compound with the MC4R.

As used herein, the term "inverse agonist" refers to any chemical compound, that, upon interacting with (e.g., binding to) its target, here, MC4R, decreases, in a dose dependent manner, the basal level of signaling activity of the MC4R.

As used herein, an "effective amount" refers to an amount of a pharmacologically active agent either as the ionic complex or a a pharmaceutical composition comprising the ionic complex that is therapeutically or prophylactically sufficient to treat the target disorder. Examples of effective amounts typically range from about 0.0001 mg/kg of body weight to about 500 mg/kg of body weight. An example range is from about 0.001 mg/kg of body weight to about 500 mg/kg. For example, the effective amount can range from about 0.005 mg/kg to about 500 mg/kg. In other examples, the range can be from about 0.0001 mg/kg to about 5 mg/kg. In still other examples, effective amounts range from about 0.01 mg/kg of body weight to 50 mg/kg of body weight, or from 0.01 mg/kg of body weight to 20 mg/kg of body weight.

As used herein, the term "second agent" includes any active pharmaceutical ingredient (API) that, in combination with a peptide described herein, enhances the therapeutic effect produced by a peptide described herein alone or shows synergy with a peptide described herein (i.e. shows the combined effect that is greater than the additive effect). As used herein, "an enhanced therapeutic effect" includes an improved therapeutic profile other than synergy. Examples of enhanced therapeutic effects include lowered effective dose of a peptide described herein, prolonged therapeutic window of a peptide described herein, etc. One or more second agents can be administered. Examples of second agents will be described in detail below.

A second agent can be administered before, simultaneously with, or after the administration of a peptide described herein. Accordingly, a peptide described herein and a second agent can be administered together in a single formulation or can be administered in separate formulations, e.g., either simultaneously or sequentially. For example, if a peptide described herein and a second agent are administered sequentially in separate compositions, a peptide described herein can be administered before or after a second therapeutic agent. In addition, a peptide described herein and a second agent may or may not be administered on similar dosing schedules. For example, a peptide described herein and a second therapeutic agent may have different half-lives and/or act on different time-scales such that a peptide described herein is administered with greater frequency than the second therapeutic agent or vice-versa. Finally, a peptide described herein can be followed by a second agent, which further enhances therapeutic efficacy, as a result of the consecutive application of both therapeutic agents. Either a peptide described herein or a second agent can be administered acutely or chronically.

An effective amount can be achieved in the methods or compositions of the invention by co-administering a first amount of a compound having an MC4R modulator activity or a pharmaceutically acceptable salt thereof and a second amount of at least one second agent. In one embodiment, a peptide described herein and second agent are each administered in a respective effective amount (i.e., each in an amount which would be therapeutically effective if administered alone). In another embodiment, a peptide described herein and a second agent are each administered in an amount which alone does not provide a therapeutic effect (a sub-therapeutic dose). In yet another embodiment, a peptide described herein can be administered in an effective amount, while the second agent is administered in a sub-therapeutic dose. In still another embodiment, a peptide described herein can be administered in a sub-therapeutic dose, while the second agent is administered in an effective amount. In example embodiment, a combination of a peptide described herein and a second agent exhibits enhanced therapeutic effect or synergy compared to either a peptide described herein or a second agent alone.

The presence of a synergistic effect can be determined using suitable methods for assessing drug interaction. Suitable methods include, for example, the Sigmoid-Emax equation (Holford, N. H. G. and Scheiner, L. B., Clin. Pharmacokinet. 6: 429-453 (1981)), the equation of Loewe additivity (Loewe, S. and Muischnek, H., Arch. Exp. Pathol. Pharmacol. 114: 313-326 (1926)), and the median-effect equation (Chou, T. C. and Talalay, P., Adv. Enzyme Regul. 22: 27-55 (1984)). Each equation referred to above can be applied with experimental data to generate a corresponding graph to aid in assessing the effects of the drug combination. The corresponding graphs associated with the equations referred to above are the concentration-effect curve, isobologram curve and combination index curve, respectively.

As used herein, the term "subject" refers to a mammal, preferably a human, but can also mean an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

As used herein "treating" includes achieving, partially or substantially, delaying, inhibiting or preventing the progression of clinical indications related to the target disorder. For example, "treating" includes achieving, partially or substantially, one or more of the following results: partially or totally reducing the body weight (as measured, for example, by a body mass index, BMI); ameliorating or improving a clinical symptom or indicators associated with obesity, such as type-2 diabetes, pre-diabetic condition, blood level of hemoglobin A1C (Hb1Ac) above 6%, hyperinsulimenia, hyperlipidemia, insulin insensitivity, glucose intolerance etc; delaying, inhibiting or preventing the progression of obesity and obesity related indication; or partially or totally delaying, inhibiting or preventing the onset or development of obesity or obesity related indication. Delaying, inhibiting or preventing the progression of the obesity includes for example, delaying, inhibiting or preventing the progression of a subject having normal weight to obesity. The term "treating" further includes partially or totally reducing the risk for coronary artery disease, stroke, and diabetes (e.g. type 2) associated with the metabolic syndrome as well as ameliorating or improving a clinical symptom or signs of metabolic syndrome associated with metabolic syndrome, such as any one or more of the five indicators listed above. For example, the term "treating" includes delaying, inhibiting or preventing the progression of parameters associated with the metabolic syndrome, including insulin resistance, glucose clearance and parameters of cardiovascular disease including heart rate and blood pressure, joint disease, inflammation, sleep apnea, binge eating and other eating disorders including bulimia, supportive therapy for weight loss surgery and supportive weight loss therapy prior to orthopedic surgery. "Prophylactic treatment" refers to treatment before onset of clinical symptoms of a target disorder to prevent, inhibit or reduce its occurrence.

Responsive Disorders

Examples of disorders responsive to the modulation of MC4R and more generally disorders responsive to the pharmacological action of the polypeptide categories and specific polypeptide listed above, include acute and chronic inflammatory diseases such as general inflammation, inflammatory bowel disease, brain inflammation, sepsis and septic shock; diseases with an autoimmune component such as rheumatoid arthritis, gouty arthritis, and multiple sclerosis; metabolic diseases and medical conditions accompanied by weight gain such as obesity, feeding disorders and Prader-Willi Syndrome; metabolic diseases and medical conditions accompanied by weight loss such as anorexia, bulimia, AIDS wasting, cachexia, cancer cachexia and wasting in frail elderly; diabetes and diabetalogical related conditions and complications of diabetes such as retinopathy; neoplastic proliferation such as skin cancer, and prostate cancer; reproductive or sexual medical conditions such as endometriosis and uterine bleeding in women, sexual dysfunction, erectile dysfunction and decreased sexual response in females; diseases or conditions resulting from treatment or insult to the organism such as organ transplant rejection, ischemia and reperfusion injury, treatment of spinal cord injury and to accelerate wound healing, as well as weight loss caused by chemotherapy, radiation therapy, temporary or permanent immobilization or dialysis; cardiovascular diseases or conditions such as hemorrhagic shock, cardiogenic shock, hypovolemic shock, cardiovascular disorders and cardiac cachexia; pulmonary diseases or conditions such as acute respiratory distress syndrome, chronic obstructive pulmonary disease, asthma and pulmonary fibrosis; to enhance immune tolerance and to combat assaults to the immune system such as those associated with certain allergies or organ transplant rejection; treatment of dermatological diseases and conditions such as psoriasis, skin pigmentation depletion, acne, keloid formation and skin cancer; behavioral, central nervous system or neuronal conditions and disorders such as anxiety, depression, memory and memory dysfunction, modulating pain perception and treating neuropathic pain; conditions and diseases associated with alcohol consumption, alcohol abuse and/or alcoholism; and renal conditions or diseases such as the treatment of renal cachexia or natriuresis. Additional examples include normalizing or homeostatic activities in a subject, including thyroxin release, aldosterone synthesis and release, body temperature, blood pressure, heart rate, vascular tone, brain blood flow, blood glucose levels, bone metabolism, bone formation or development, ovarian weight, placental development, prolactin and FSH secretion, intrauterine fetal growth, parturition, spermatogenesis, sebum and pheromone secretion, neuroprotection and nerve growth as well as modulating motivation, learning and other behaviors. Further examples include binge eating, bulimia or other eating disorders.

In example embodiments, the disorders responsive to the modulation of the MC4R receptor are type 1 diabetes, type 2 diabetes, obesity, insulin resistance, metabolic syndrome, cardiovascular disease, or low density lipoprotein/high density lipoprotein/triglyceride imbalance, non-alcoholic fatty liver disease, and disorders of substance abuse.

In example embodiments, the disorders responsive to the modulation of the MC4R receptor is type 1 diabetes, type 2 diabetes, obesity, insulin resistance or metabolic syndrome.

Obesity

As used herein, the term "obese" refers to a subject having a body mass index (BMI) of about 30 kg/m$^2$ or higher, e.g., a BMI of 25, 26, 27, 28, 29, 30, 31, 32, 33, 34, 35, 36, 37 kg/m$^2$, or more. In particular embodiments, an obese subject has a BMI within the ranges defined as "obese" by the Center for Desease Control. See, URL http://www.cdc.gov/obesity/defining.html, last accessed on Oct. 28, 2011. For example, in some embodiments, an adult who has a BMI>=30.0 kg/m$^2$ is obese.

Diabetes and Related Disorders

In example embodiments, subjects to be treated by the methods provided by the invention have or are at increased risk for developing diabetes related disorders. "Diabetes-related disorders," refers to diabetes (including type 1 (OMIM 222100) and type 2 (OMIM 125853)), insulin resistance and metabolic syndrome.

In example embodiments, the subject to be treated has diabetes (type 1 or type 2), insulin resistance or metabolic syndrome. In example embodiments, the disorder is diabetes, e.g. type 2 diabetes. In example embodiments, the subject has, or is at increased risk for developing, type 2 diabetes as defined by the World Health Organization and the International Diabetes Federation in "Definition and diagnosis of diabetes mellitus and intermediate hyperglycaemia," published in 2006, which is incorporated by reference in its entirety. In example embodiments, a diabetic subject exhibits a fasting plasma glucose of >=126 mg/dL or a 2-hour plasma glucose (2 hours after oral administration of 75 glucose)>=200 mg/dL. In example embodiments a diabetic or pre-diabetic subject exhibits elevated levels of glycated hemoglobin, e.g., greater than 4.5, 4.6, 4.7, 4.8, 4.9, 5.0, 5.1, 5.2, 5.3, 5.4, 5.5, 5.6, 5.8, 6.0, 6.2, 6.4, 6.6, 6.8, 7.0, 7.2, 7.4, 7.6%, or more of total hemoglobin. In example embodiments, a diabetic or pre-diabetic subject may be identified or further characterized by genetic polymorphisms (including, for example, polymorphisms leading to altered expression levels, e.g., elevated or reduced expression levels and/or variations in coding sequences) in or near one or more of the genes in Table 1, below:

TABLE 1

| Location | Gene/Locus | OMIM No. |
|---|---|---|
| 2q24.1 | GPD2 | 138430 |
| 2q31.3 | NEUROD1 | 601724 |
| 2q36.3 | IRS1 | 147545 |
| 3p25.2 | PPARG | 601487 |
| 3q27.2 | IGF2BP2 | 608289 |
| 4p16.1 | WFS1 | 606201 |
| 5q34-q35.2 | NIDDM4 | 608036 |
| 6p22.3 | CDKAL1 | 611259 |
| 6p21.31 | HMGA1 | 600701 |
| 6q23.2 | ENPP1 | 173335 |
| 7p13 | GCK | 138079 |
| 7q32.1 | PAX4 | 167413 |
| 8q24.11 | SLC30A8 | 611145 |
| 10q25.2-q25.3 | TCF7L2 | 602228 |
| 11p15.1 | KCNJ11 | 600937 |
| 11p15.1 | ABCC8 | 600509 |
| 11p11.2 | MAPK8IP1 | 604641 |
| 12q24.31 | HNF1A | 142410 |
| 13q12.2 | IPF1 | 600733 |
| 13q34 | IRS2 | 600797 |
| 15q21.3 | LIPC | 151670 |
| 17p13.1 | SLC2A4 | 138190 |
| 17q12 | HNF1B | 189907 |
| 17q25.3 | GCGR | 138033 |
| 19p13.2 | RETN | 605565 |
| 19p13.2 | RETN | 605565 |
| 19q13.2 | AKT2 | 164731 |
| 20q12-q13.1 | NIDDM3 | 603694 |
| 20q13.12 | HNF4A | 600281 |
| 20q13.13 | PTPN1 | 176885 |

In example embodiments, additional genes that can be used to identify or further characterize subjects to be treated by the methods provided by the invention include FTO (OMIM 610966), JAZF1 (OMIM 606246) and HHEX (604420).

In example embodiments, a subject to be treated by the methods provided by the invention has type 1 diabetes. In example embodiments, a subject with type 1 diabetes is characterized by virtue of a C-peptide assay, e.g., fasting C-peptide levels of less than about 1.0 nmol/L, e.g., less than 1.2, 1.1, 1.0, 0.9, 0.8, 0.7, 0.6, 0.5, 0.4 nmol/L, or less, e.g., less than 0.33, 0.25, 0.2, or 0.1 nmol/L. In example embodiments, C-peptide levels are measured after oral glucose challenge (2 hours after oral administration of 75 g of glucose) and an increase of less than 0.54 nmol/L, e.g., less than 0.50, 0.45, 0.40, 0.35, 0.30, 0.25, 0.20, 0.15, or 0.10 nmol/L is detected. Impaired fasting glucose (110-125 mg/dL) or impaired glucose tolerance (2 hours after oral administration of 75 g of glucose challenge: 140-199 mg/dL) may be used to identify or further characterize the reduced beta-cell function in subjects with type 1 diabetes. In example embodiments, type1 diabetics are identified or further characterized by the presence of autoantibodies to islet cell antigens and/or insulin, e.g., autoantibodies directed to 65 kDa of GAD (OMIM 138275) and/or phosphatase-related IA-2 molecule.

Insulin Resistance

In example embodiments, the disorder is "insulin resistance," which may be identified by any means known in the art, and is characterized by a reduced ability of insulin to lower blood glucose levels. In example embodiments, the insulin resistance is identified or further characterized by the presence of one or more polymorphisms (including, for example, polymorphisms leading to altered expression levels, e.g., elevated or reduced expression levels as well as coding sequence variants of gene products, such as proteins) in one or more of the following genes: RETN, PTPN1, TCF1 (OMIM 142410; see, e.g., polymorphism 0011), PPP1R3A (OMIM 600917; see, e.g., polymorphisms 0001, 0003), PTPN1 176885; see, e.g., polymorphism 0001), ENPP1 (OMIM 173335; see, e.g., polymorphism 0006), IRS1 (OMIM 147545; see, e.g., polymorphism 0002), EPHX2 (OMIM 132811; see, e.g., polymorphism 0001), leptin (OMIM 164160, see, e.g., polymorphisms 0001 and 0002), leptin receptor (OMIM 601007, see, e.g., polymorphisms 0001, 0002, 0004, and 0005), or the insulin receptor (INSR, OMIM 147670, see, e.g., polymorphisms 0001-0037).

Metabolic Syndrome

In example embodiments, the disorder is metabolic syndrome. As used herein, the term "metabolic syndrome" refers to a group of symptoms that occur together and increase the risk for coronary artery disease, stroke, and type 2 diabetes. According to the American Heart Association and the National Heart, Lung, and Blood Institute, metabolic syndrome also referred to as Syndrome X) is present if a subject has three or more of the following signs:

1) Blood pressure equal to or higher than 130/85 mmHg;
  2) Fasting blood sugar (glucose) equal to or higher than 100 mg/dL;
  3) Large waist circumference (length around the waist):
  Men—40 inches or more;
  Women—35 inches or more;
  4) Low HDL cholesterol:
  Men—under 40 mg/dL;
  Women—under 50 mg/dL;
  5) Triglycerides equal to or higher than 150 mg/dL.

Metabolic syndrome can be diagnosed by testing the subject's blood pressure, blood glucose level, HDL cholesterol level, LDL cholesterol level, total cholesterol level, and triglyceride level.

In example embodiments the subject has central obesity (waist circumference>=80 cm for women; >=90 cm for Asian men, including ethnic South and Central Americans, and >=94 cm for all other males), BMI>30 kg/m$^2$, raised triglycerides (>=150 mg/dL, or specific treatment for this lipid abnormality), reduced HDL cholesterol (<40 mg/dL in males, <50 mg/dL in females or specific treatment for this lipid abnormality), raised blood pressure (sBP>=130 mmHg or dBP>=85 mmHg or treatment of previously diagnosed hypertension) or raised fasting plasma glucose (FPG>=100 mg/dL or previous type 2 diabetes diagnosis), including combinations thereof. In example embodiments, the subject to be treated by the methods provided by the invention has or is at increased risk for metabolic syndrome, as defined by the International Diabetes Federation in "The IDF consensus worldwide definition of the metabolic syndrome," published in 2006, which is incorporated by reference in its entirety, i.e., the subject has central obesity (as described above, and/or BMI>30 kg/m$^2$) AND any two of raised triglyceries, reduced HDL cholesterol, raised blood pressure, or raised fasting plasma glucose. In example embodiments, metabolic syndrome is characterized, or further characterized, by the presence of a mutation at a locus selected from 3q27 (see, for example, OMIM 605552) and/or 17p12 (see, for example, OMIM 605572) in the subject.

Disorders Caused by MC4R Mutations

The present invention relates to a method of treating a disorder in a subject suffering from an attenuated response of MC4R to α-melanocortin stimulating hormone (α-MSH). The method comprises administering an effective amount of an agonist of the melanocortin-4 receptor (MC4R). In an example embodiment, the subject is a heterozygous carrier of an MC4R mutation resulting in the attenuated response of MC4R to α-melanocortin stimulating hormone (α-MSH). Because heterozygous carriers retain an ability to respond to the natural ligand of MC4R, treating MC4R-associated disorders in heterozygous carriers by administration of an MC4R agonist does not rely on the knowledge of the type of the MC4R mutation.

In one example embodiment, the disorder is obesity, for example, MC4R-associated obesity. In another example embodiment, the disorder is metabolic syndrome.

Human MC4R gene (hMC4R) is a well-characterized protein encoded by a genomic sequence having GenBank accession number CH471077.

Mutations in the MC4R receptor are an associated cause of severe childhood obesity. The carrier prevalence for MC4R mutations in a juvenile-onset obese population has been noted to be around 2.5% with a highest prevalence of 6% among severe obese children. Humans with MC4R mutations show a more or less similar phenotype as has been described for mice with mutations in the MC4 receptor gene. Those people show clear hyperphagia, hyperinsulinaemia, increased fat mass, accompanied by lean body mass, bone mineral density and linear growth rate, with no changes in cortisol levels, gonadotropin, thyroid and sex steroid levels. In contrast to MC4 receptor deletion, hyperphagia and hyperinsulinaemia tends to subside with age in human subjects. Similar to the MC4R knockout mice, the phenotype in heterozygote carriers is intermediate in comparison to homozygote carriers. The exhibited hyperphagia observed upon a test meal is less severe than that observed in people with a leptin deficiency. The severity of MC4 receptor dysfunction seen in assays in vitro can predict the amount of food ingested at a test meal by the subject harboring that particular mutation and correlates with the onset and severity of the obese phenotype. At least 90 different MC4 receptor mutations have been associated with obesity and additional mutations in the MC4 receptor are likely to be discovered, leading to a similar obesity phenotype.

Examples of the MC4R mutations that cause obesity in humans are described in Farooqi et al., *The Journal of Clinical Investigation*, July 2000, vol. 106 (2), pp. 271-279 and Vaisse et al., *The Journal of Clinical Investigation*, July 2000, vol. 106(2), pp. 253-262, the relevant portions of which are incorporated herein by reference.

Additional mutations that potentially cause obesity in humans include, R18H, R18L, S36Y, P48S, V50M, F51L, E61K, I69T, D90N, S94R, G98R, I121T, A154D, Y157S, W174C, G181D, F202L, A219 V, I226T, G231S, G238D, N240S, C271R, S295P, P299L, E308K, I317V, L325F, and 750DelGA, as described in Xiang et al., "Pharmacological characterization of 30 human melanocortin-4 receptor polymorphisms with the endogenous proopiomelanocortin-derived agonists, synthetic agonists, and the endogenous agouti-related protein antagonist." Biochemistry, 2010 Jun. 8; 49(22):4583-600, the relevant portions of which are incorporated herein by reference.

Further examples of mutations that potentially cause obesity in humans are those listed in Online Mendelian Inheritance in Man (OMIM), a database of human genes and genetic disorders, under the accession number 155541 (MC4R) (more precisely, accession nos. 155541.0001-155541.0023) at the URL http://omim.org/entry/155541. Representative examples include 4-BP DEL, NT631; 4-BP INS, NT732; TYR35TER; ASP37VAL; SER58CYS; ILE102SER; ASN274SER; 1-BP INS, 112A; 4-BP DEL, 211CTCT; ILE125LYS; ALA175THR; ILE316SER; TYR287TER; ASN97ASP; 15-BP DEL (delta88-92 codons); and SER127LEU. The relevant portions of the OMIM database are incorporated herein by reference.

In example embodiments, the MC4R mutation results in retention of the MC4R signaling activity.

Mutations in the genomic sequence encoding MC4R can be detected by the methods that are well known to a person of ordinary skill in the art. For example, the genomic sequence can be cloned using nucleotide primers, such as e.g., the primers described in Farooqi et al., The Journal of Clinical Investigation, July 2000, vol. 106 (2), pp. 271-279 and Vaisse et al., The Journal of Clinical Investigation, July 2000, vol. 106(2), pp. 253-262, and the cloned sequence analyzed using commercially available sequencers and software.

Activity of MC4R can be measured by the methods well known to a person of ordinary skill in the art. For example, cells can be transiently transfected with the cloned MC4R DNA, the transfected cells contacted by an agonist of MC4R (e.g. α-MSH), and the intracellular level of cAMP, the secondary messenger of MC4R, measured by an electrochemiluminescence assay described, e.g., in Roubert et al., Journal of Endocrinology (2010) 207, pp. 177-183. A reduction in MC4R signaling can be ascertained by comparing the intracellular level of cAMP produced in response to a given agonist by a wild type MC4R to that produced by a mutant MC4R.

MC4R modulators (e.g. agonists) may also be used to treat patients suffering from other disorders, such as reduced tone of the natural agonists of the MC4R. Example of such patients include individuals heterozygous or homozygous for mutations in the genes important in leptin-dependent pathway (Nature Clinical Practice Endocrinology and Metabolism, 2006; 2; 6; 318 and NEng J Med: 2007; 356; 3; 237), proopiomelanocortin processing (Nature Genetics, 1998, 155; Cell Metabolism, 2006; 3; 135; Annals Acad Med, 2009, 38; 1; 34), or mutations in the genes coding for prohormone convertases.

Modes of Administration

Administration of a ionic complex or pharmaceutical composition described herein useful to practice the methods described herein, can be continuous, hourly, four times daily, three time daily, twice daily, once daily, once every other day, twice weekly, once weekly, once every two weeks, once a month, or once every two months, once every 3 months, once every 4 months, once every 5 months or once every 6 months or longer or some other intermittent dosing regime. The ionic comple compositions of this invention are suitable for effective therapeutic administration ranging from once daily, once weekly, once every 2 weeks, once every four weeks, once every 2 months, once every 3 months, once every 4 months, once every 5 months or once every 6 months.

Suitable methods of administration include, but are not limited to peripheral administration. Examples of peripheral administration include oral, subcutaneous, intraperitoneal, intramuscular, intravenous, rectal, transdermal, buccal, sublingual, inhalation, pulmonary, or intranasal forms of administration. Preferred embodiments use subcutaneous administration.

Combination Therapy

Any peptide described herein whether part of an ionic complex or uncomplexed (e.g., Peptide 1 before complexation) can be used for treatment of any of the disorders responsive to the modulation of MC4R, by administration in combination with one or more other pharmaceutically active compounds ("second agent"). Such combination administration can be by means of a single dosage form which includes one or more peptides described herein and one or more second agents, such single dosage forms include a tablet, capsule, spray, inhalation powder, injectable liquid, or the like. Alternatively, combination administration can be by means of administration of two different dosage forms, with one dosage form containing one or more peptides described herein, and the other dosage form including one or more second agents. In this instance, the dosage forms may be the same or different. Without meaning to limit combination therapies, the following exemplifies certain combination therapies which may be employed.

A peptide described herein (e.g., as part of the ionic complex or uncomplexed) can be combined with one or more second agents useful in the treatment of various weight and feeding-related disorders, such as obesity and/or overweight. In particular, a second agent can be an anti-obesity drug that affects energy expenditure, glycolysis, gluconeogenesis, glucogenolysis, lipolysis, lipogenesis, fat absorption, fat storage, fat excretion, hunger and/or satiety and/or craving mechanisms, appetite/motivation, food intake, or gastrointestinal motility. Drugs that reduce energy intake include, in part, various pharmacological agents, referred to as anorectic drugs, which are used as adjuncts to behavioral therapy in weight reduction programs.

Generally, a total dosage of the obesity control agents or medications, when used in combination with one or more peptide described herein can range from 0.1 to 3,000 mg/day, preferably from about 1 to 1,000 mg/day, and more preferably from about 1 to 200 mg/day in single or 2-4 divided doses. The exact dose, however, is determined by the attending clinician and is dependent on such factors as the potency of the compound administered, the age, weight, condition, and response of the patient.

One or more peptides described herein (either as part of an ionic complex or uncomplexed) can be combined with one or more second agents useful in the treatment of diabetes.

One or more peptides described herein can in addition or alternatively further be combined with one or more second agents useful in the treatment of diseases, disorders and/or conditions associated with obesity and/or overweight, such as insulin resistance; impaired glucose tolerance; type 2 diabetes; metabolic syndrome; dyslipidemia (including hyperlipidemia); hypertension; heart disorders (e.g. coronary heart disease, myocardial infarction); cardiovascular disorders; non-alcoholic fatty liver disease (including non-alcoholic steatohepatitis); joint disorders (including secondary osteoarthritis); gastroesophageal reflux; sleep apnea; atherosclerosis; stroke; macro and micro vascular diseases; steatosis (e.g. in the liver); gall stones; and gallbladder disorders.

Second Agent

The one or more second agents are, for example, selected from:

insulin and insulin analogues;
insulin secretagogues, including sulphonylureas (e.g. glipizide) and prandial glucose regulators (sometimes called "short-acting secretagogues"), such as meglitinides (e.g. repaglinide and nateglinide);

agents that improve incretin action: an incretin, an incretin mimetic, an agents that improves incretin function e.g. GLP-1, GIP; GLP-1 agonists (e.g., exenatide and liraglutide (VICTOZA)), DPP-4 inhibitors (e.g. vildagliptin, saxagliptin, and sitagliptin)

insulin sensitising agents including peroxisome proliferator activated receptor gamma (PPARγ) agonists, such as thiazolidinediones (e.g. pioglitazone and rosiglitazone), and agents with any combination of PPAR alpha, gamma and delta activity;

agents that modulate hepatic glucose balance, for example biguanides (e.g. metformin), fructose 1,6-bisphosphatase inhibitors, glycogen phopsphorylase inhibitors, glycogen synthase kinase inhibitors, and glucokinase activators;

agents designed to reduce/slow the absorption of glucose from the intestine, such as alpha-glucosidase inhibitors (e.g. miglitol and acarbose);

agents which antagonize the actions of or reduce secretion of glucagon, such as amylin analogues (e.g. pramlintide);

agents that prevent the reabsorption of glucose by the kidney, such as sodium-dependent glucose transporter 2 (SGLT-2) inhibitors (e.g. dapagliflozin);

agents designed to treat the complications of prolonged hyperglycaemia, such as aldose reductase inhibitors (e.g. epalrestat and ranirestat);

agents used to treat complications related to microangiopathies;

anti-dyslipidemia agents, such as HMG-CoA reductase inhibitors (statins, e.g. rosuvastatin) and other cholesterol-lowering agents;

PPARα agonists (fibrates, e.g. gemfibrozil and fenofibrate);

bile acid sequestrants (e.g. cholestyramine);

cholesterol absorption inhibitors (e.g. plant sterols (i.e. phytosterols), synthetic inhibitors);

cholesteryl ester transfer protein (CETP) inhibitors; inhibitors of the ileal bile acid transport system (IBAT inhibitors);

bile acid binding resins;

nicotinic acid (niacin) and analogues thereof;

anti-oxidants, such as probucol;

omega-3 fatty acids;

antihypertensive agents, including adrenergic receptor antagonists, such as beta blockers (e.g. atenolol), alpha blockers (e.g. doxazosin), and mixed alpha/beta blockers (e.g. labetalol);

adrenergic receptor agonists, including alpha-2 agonists (e.g. clonidine);

angiotensin converting enzyme (ACE) inhibitors (e.g. lisinopril), calcium channel blockers, such as dihydropyridines (e.g. nifedipine), phenylalkylamines (e.g. verapamil), and benzothiazepines (e.g. diltiazem);

angiotensin II receptor antagonists (e.g. candesartan); aldosterone receptor antagonists (e.g. eplerenone);

centrally acting adrenergic drugs, such as central alpha agonists (e.g. clonidine); and diuretic agents (e.g. furosemide);

haemostasis modulators, including antithrombotics, such as activators of fibrinolysis;

thrombin antagonists;

factor VIIa inhibitors; anticoagulants, such as vitamin K antagonists (e.g. warfarin), heparin and low molecular weight analogues thereof, factor Xa inhibitors, and direct thrombin inhibitors (e.g. argatroban); antiplatelet agents, such as cyclooxygenase inhibitors (e.g. aspirin), adenosine diphosphate (ADP) receptor inhibitors (e.g. clopidogrel), phosphodiesterase inhibitors (e.g. cilostazol), glycoprotein IIB/IIA inhibitors (e.g. tirofiban), and adenosine reuptake inhibitors (e.g. dipyridamole);

anti-obesity agents, such as appetite suppressant (e.g. ephedrine), including noradrenergic agents (e.g. phentermine) and serotonergic agents (e.g. sibutramine), pancreatic lipase inhibitors (e.g. orlistat), microsomal transfer protein (MTP) modulators, diacyl glycerolacyltransferase (DGAT) inhibitors, and cannabinoid (CB1) receptor antagonists (e.g. rimonabant);

feeding behavior modifying agents, such as orexin receptor modulators and melanin-concentrating hormone (MCH) modulators;

neuropeptide Y (NPY)/NPY receptor modulators;

pyruvate dehydrogenase kinase (PDK) modulators;

serotonin receptor modulators;

leptin/leptin receptor modulators;

ghrelin/ghrelin receptor modulators;

an agent that enhances Beta-cell function;

an agent that stimulates energy expenditure (e.g. beta-adrenergic stimulants, UCP-1 agonists, brown fat modulators and stimulants);

an agent that induces lysis of adipocytes (e.g. an antibody);

nicotine or a nicotine withdrawal aid;

estrogen, a natural or synthetic modulator of an estrogen receptor;

a µ-opioid receptor modulator; and monoamine transmission-modulating agents, such as selective serotonin reuptake inhibitors (SSRI) (e.g. fluoxetine), noradrenaline reuptake inhibitors (NARI), noradrenaline-serotonin reuptake inhibitors (SNRT), triple monoamine reuptake blockers (e.g. tesofensine), and monoamine oxidase inhibitors (MAOI) (e.g. toloxatone and amiflamine), or a pharmaceutically acceptable salt thereof.

In an example embodiment, an MC4R agonist (e.g., an MC4R agonist that is part of an ionic complex or uncomplexed) and a second agent are administered with the simultaneous, sequential or separate administration of a very low calorie diets (VLCD) or low-calorie diets (LCD).

Method of Preparing the Ionic Complex

The invention further relates to a method of for preparing the ionic complex and pharmaceutical composition of the invention. The method includes providing a cationic polypeptide and an anionic excipient selected from a PEG-carboxylic acid, a fatty acid having 10 or more carbon atoms, a phospholipid, or a combination thereof. Combining the cationic polypeptide and the anionc excipient under conditions to form an ionic complex and preparing a pharmaceutical composition comprising the ionic complex.

For example, a mixture of an anionic excipient selected from a PEG-carboxylic acid, a fatty acid having 10 or more carbon atoms, a phospholipid, or a combination thereof and any additional excipients in an aqueous medium (e.g., water) can be uniformly constituted in a well dispersed state by autoclaving the mixture under suitable conditions. Suitable conditions can include, for example, from about 3 minutes to about 25 minutes at a temperature of 121° C. to 134° C. An example of suitable conditions includes, a time of about 15 minutes at a temperature of about 121° C. The use of autoclaving also affords a sterile mixture. A sterile aqueous solution of the cationic peptide can then be added to the mixture to afford, a sterile, homogeneous ionic complex of this invention. Depending on the nature of the anionic excipient, either a clear solution or a uniform suspension of the ionic complex can be obtained. For example, the PEG-carboxylate and mPEG2000-DSPE used in the examples described herein typically results in a clear solution comprising the ionic complex, while the use of DPPA lipid typically results in a homogenous suspension comprising the ionic complex.

Alternatively, the mixture of the ionic complex can be prepared by dissolving the excipients in water with the cationic polypeptide and sterile filtering the resulting mixture through a 0.2 micron filter.

A method of making an ionic complex comprising a cationic polypeptide and an anionic excipient selected from: a PEG-carboxylic acid; a fatty having 10 or more carbon atoms; a phospholipid; and a combination thereof, comprising:
 a) preparing a mixture of the anionic excipient and an aqueous excipient diluent;
 b) autoclaving the mixture under conditions sufficient to sterilize the excipient;
 c) adding a sterile peptide solution comprising a cationic polypeptide and a aqueous peptide diluent to the excipient mixture.

In one embodiment, the excipient mixture is a suspension. In another embodiment, the excipient mixture is a solution.

In an alternative embodiment, the invention relates to a method of making an ionic complex comprising a cationic polypeptide and an anionic excipient selected from: a PEG-carboxylic acid; a fatty having 10 or more carbon atoms; a phospholipid; and a combination thereof, comprising:
 a) preparing a solution of the anionic excipient and an aqueous excipient diluent;
 b) filtrating the solution of step a through a 0.2 micron filter;
 c) adding a sterile peptide solution comprising a cationic polypeptide of and an aqueous peptide diluent to the excipient solution of step b.

In yet another embodiment, the invention relates to a method of making an ionic complex comprising a cationic polypeptide and an anionic excipient selected from: a PEG-carboxylic acid; a fatty having 10 or more carbon atoms; a phospholipid; and a combination thereof, comprising:
 a) preparing a solution comprising the anionic excipient an aqueous excipient diluent, and a cationic polypeptide;
 b) sterilizing the resulting solution by filtering through a 0.2 micron filter.

Suitable examples of excipient and cationic polypeptide excipient include polyol (e.g., propylene glycol, tripropylene glycol, glycerol, ethanol, benzyl alcohol, DMSO, NMP, DMF, water, pH stabilizing buffered solutions and mixtures thereof.

Exemplification

Peptide Synthesis

The cationic polypeptides suitable for use in this invention were prepared by conventional solid phase peptide synthesis. For example, Peptide 1 and other MC4R analogs described herein can be prepared according to the methods described in U.S. Pat. No. 8,349,797, the entire content of which is hereby incorporated by reference. The peptide chain was elongated in a step-wise manner starting with its C-terminal end amino acid derivative coupled on to an appropriately selected solid support resin known to be suitable for peptide synthesis. For the synthesis of peptide with a C-terminal amide function, Rink amide MBHA resin was employed as solid support. For the synthesis of peptides with the C-terminal free carboxyl function, resins such as 2-chlorotrityl chloride resin, Wang, or Merrifield resin may be utilized that form an ester bond with the Fmoc-amino acid. Most of these ester linked Fmoc-amino acid-resin types are commercially available from various sources and generally used when feasible.

Synthesis of Disulfide-Cyclized Peptides

The linear derivative of a disulfide cyclic peptides amide was assembled using Fmoc chemistry on a solid-phase peptide synthesizer. The Fmoc-Rink amide resin was placed in a reaction vessel and swollen with NMP. It was then treated with 20% piperidine in NMP for 15 minutes, followed by 3 washes of NMP. The resin was tested for positive Kaiser's test (Kaiser, E., Colescot, R. L., Bossinge, C. D. & Cook, P. I. Anal. Biochem., 1990, 34: 595-598). It was resuspended in NMP and mixed with the required first C-terminal Fmoc-amino acid derivative and HOBt. The coupling reaction was started by the addition of HBTU reagent and DIPEA. After mixing for 2-3 hours, the completion of coupling was confirmed by a negative Kaiser's test on a small aliquot of the resin withdrawn from the reaction mixture. The resin was then washed three times with NMP. Thereafter, the Fmoc group was removed as described earlier and the whole cycle repeated with the second C-terminal Fmoc-amino acid derivative as described. The same cycle of reactions was repeated sequentially with each of the incoming amino acid. The chloranil color test (Vojkovsky, T. Pept. Res., 1995, 8: 236-237) was used instead of Kaiser's test for positive testing of Fmoc deprotection from the proline residue in the peptide sequence as well for testing completion of coupling of an amino acid to proline (a negative chloranil test). In case of peptides with N-terminal acetyl group, the Fmoc deprotected peptide resin was treated for 10 minutes with acetic anhydride and pyridine. The resin after testing negative for Kaiser's test was washed with NMP, dichlormethane and dried in vacuo. The Fmoc-amino acid derivatives were used for the synthesis of these peptides. The trifunctional amino acid derivatives used were the following: Fmoc-Cys(Trt)-OH, Fmoc-Trp(Boc)-OH, Fmoc-Arg(Pbf)-OH, Fmoc-His(Trt)-OH, Fmoc-Asn(Trt)-OH, Fmoc-Gln(Trt)-OH, Fmoc-hCys(Trt)-OH, Fmoc-Pen(Trt)-OH, Fmoc-Tyr(But)-OH, Fmoc-His(1-Me)-OH, Fmoc-His (3-Me)-OH, and Fmoc-Glu(OBut)-OH.

To cleave the peptide off the resin as well as to deprotect the side chain functions, the peptide resin was taken in: 2% TIS/5% water/5% (w/v) DTT/88% TFA. The solution was allowed to mix for 3.5 hours and then filtered. The filtrate was mixed with cold anhydrous ethyl ether. The precipitate was collected by centrifugation. The solvent was decanted and the peptide pellet was re-suspended in fresh ether. The ether workup was repeated two more times. The peptide was dried in vacuo. The crude linear peptide product was diluted to a concentration of 2 mg/mL in 5% acetic acid and 0.5M iodine/methanol was added dropwise with vigorous stirring until a persistent pale yellow color of the solution was achieved. The solution was stirred for additional 10 minutes. Excess iodine was then quenched by adding 1M sodium thiosulfate under mixing until the mixture was rendered colorless. The cyclized peptide solution was lyophilized and the crude powder purified by preparative HPLC using a reversed-phase C-18 column. The purified product fractions were pooled and lyophilized. The peptides were analyzed by mass spectrometry using electrospray ionization technique and identified to correct mass.

Synthesis of Lactm-Cyclized Peptides

The cyclic lactam peptides were also synthesized by standard solid phase peptide synthesis methods. For peptides with a C-terminus Dpr, an Fmoc-Dpr(Mtt)-BHA resin was transferred to a solid phase peptide synthesizer reactor. The Fmoc group, was removed as described above and the next Fmoc-protected amino acid, such as for example Fmoc-Trp (Boc)-OH, was coupled to the resin through standard coupling procedures. The Fmoc protective group was removed and the remaining amino acids added individually in the correct sequence, by repeating coupling and deprotection procedures until the amino acid sequence was completed. For glutamic acid, coupling Fmoc-Glu(OPip) was employed. The fully assembled peptide was then acetylated at the N-terminus as per method described earlier for the disulfide series of peptides. The orthogonally protected side chains were then removed. For example, a peptide resin with either an orthogonally protected side chain of Glu as 2-phenylisoproply (OPip) ester or Dpr as 4-methyltrityl (Mtt), were cleaved by treatment with 1% TFA in dicholoromethane. The deprotected peptide resin was suspended in NMP, and treated with HBTU/DIPEA. After cyclization (a negative Kaiser's test), the peptide-resin was washed with DCM and dried. The cyclic peptide was cleaved from the resin along with any remaining protective groups using trifluoroacetic acid (TFA) in the presence of water and 1,2-ethanedithiol (EDT). The product was collected by precipitation upon the addition of cold anhydrous ether and collected by centrifugation. Final purification was by reversed phase HPLC using a reversed phase C-18 column. The purified peptide collected by lyophilization and analyzed for its mass by mass spectrometry using electron spray methodology.

TABLE 1

Examples of Cationic Peptides of Formula I

| Compound | (SEQ ID NO: 1) |
|---|---|
| Peptide 1 | Ac-Arg-Cys-D-Ala-D-His-D-Phe-Arg-Trp-Cys-NH$_2$ |
| 1 | Ac-Arg-cyclo[Cys-D-Leu-His-D-Phe-Arg-Trp-Cys]-NH$_2$ (SEQ ID NO: 2) |
| 2 | Ac-Arg-cyclo[Cys-D-Ile-His-D-Phe-Arg-Trp-Cys]-NH$_2$ (SEQ ID NO: 3) |
| 3 | Ac-Arg-cyclo[Cys-D-Tie-His-D-Phe-Arg-Trp-Cys]-NH$_2$ |
|   | Tle = t-butyl glycine (SEQ ID NO: 4) |
| 4 | Ac-Arg-cyclo[Cys-D-Val-His-D-Phe-Arg-Trp-Cys]-NH$_2$ (SEQ ID NO: 5) |
| 5 | Ac-Arg-cyclo[Cys-D-Ala-His(3-Me)-D-Phe-Arg-Trp-Cys]-NH$_2$ (SEQ ID NO: 6) |
| 6 | Ac-Arg-cyclo[Cys-D-Ala-His(1-Me)-D-Phe-Arg-Trp-Cys]-NH$_2$ (SEQ ID NO: 7) |
| 7 | Ac-Arg-cyclo[Cys-D-Ala-Trp-D-Phe-Arg-Trp-Cys]-NH$_2$ (SEQ ID NO: 8) |
| 8 | Ac-Arg-cyclo[Cys-D-Ala-Gln-D-Phe-Arg-Trp-Cys]-NH$_2$ (SEQ ID NO: 9) |
| 9 | Ac-Arg-cyclo[Cys-D-Ala-Asn-D-Phe-Arg-Trp-Cys]-NH$_2$ (SEQ ID NO: 10) |
| 10 | Ac-Arg-cyclo[Cys-D-Ala-Arg-D-Phe-Arg-Trp-Cys]-NH$_2$ (SEQ ID NO: 11) |
| 11 | Ac-Arg-cyclo[Cys-D-Ala-Tyr-D-Phe-Arg-Trp-Cys]-NH$_2$ (SEQ ID NO: 12) |
| 12 | Ac-Arg-cyclo[Cys-D-Ala-D-Pro-D-Phe-Arg-Trp-Cys]-NH$_2$ (SEQ ID NO: 13) |
| 13 | Ac-Arg-cyclo[Cys-D-Ala-Pro-D-Phe-Arg-Trp-Cys]-NH$_2$ (SEQ ID NO: 14) |
| 14 | Ac-Arg-cyclo[Cys-D-Ala-Pro-D-Phe(p-F)-Arg-Trp-Cys]-NH$_2$ (SEQ ID NO: 15) |
| S1 | Ac-Arg-cyclo[Cys-D-Ala-Atc-D-Phe-Arg-Trp-Cys]-NH$_2$ (SEQ ID NO: 16) |
|   | Atc = 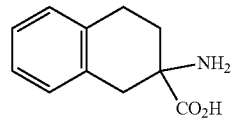 |
| S2 | Ac-Arg-cyclo[Cys-D-Ala-QAla-D-Phe-Arg-Trp-Cys]-NH$_2$ (SEQ ID NO: 17) |
|   | QAla = 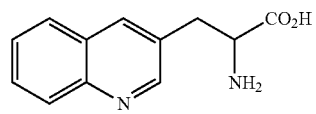 [SMILES: NC(Cc1cnc2ccccc2c1)C(=O)O] |

TABLE 1-continued

Examples of Cationic Peptides of Formula I

| Compound | | (SEQ ID NO: 1) |
|---|---|---|
| Peptide 1 | Ac-Arg-Cys-D-Ala-D-His-D-Phe-Arg-Trp-Cys-NH₂ | |

S3  Ac-Arg-cyclo[Cys-D-Ala-sChp-D-Phe-Arg-Trp-Cys]-NH2 (SEQ ID NO: 18)
sChp =

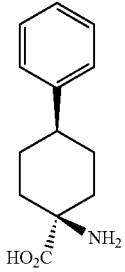

S4  Ac-Arg-cyclo[Cys-D-Ala-X-D-Phe-Arg-Trp-Cys]-NH₂ (SEQ ID NO: 19)
X =

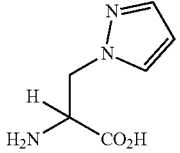

15   Ac-Arg-cyclo[hCys-Ala-D-Phe-Arg-Trp-Cys]-NH₂ (SEQ ID NO: 20)
16   Ac-Arg-cyclo[hCys-D-Ala-D-Phe-Arg-Trp-Cys]-NH₂ (SEQ ID NO: 21)
17   Ac-Arg-cyclo[hCys-D-Ala-D-Phe-Arg-Trp-Pen]-NH₂ (SEQ ID NO: 22)
18   Ac-Arg-cyclo[Glu-D-Ala-D-Phe-Arg-Trp-Dpr]-NH₂ (SEQ ID NO: 23)
19   Ac-Arg-cyclo[Glu-Ala-D-Phe-Arg-Trp-Dpr]-NH₂ (SEQ ID NO: 24)
S5   Ac-Arg-cyclo[hCys-Aib-D-Phe-Arg-Trp-Cys]-NH₂ (SEQ ID NO: 25)
S6   Ac-Arg-cyclo[hCys-Sar-D-Phe-Arg-Trp-Cys]-NH₂ (SEQ ID NO: 26)
S7   Ac-Arg-cyclo[hCys-Val-D-Phe-Arg-Trp-Cys]-NH₂ (SEQ ID NO: 27)
S8   Ac-Arg-cyclo[hCys-D-Val-D-Phe-Arg-Trp-Cys]-NH₂ (SEQ ID NO: 28)
S9   Ac-Arg-cyclo[hCys-Gln-D-Phe-Arg-Trp-Cys]-NH₂ (SEQ ID NO: 29)
S10  Ac-Arg-cyclo[hCys-D-Gln-D-Phe-Arg-Trp-Cys]-NH₂ (SEQ ID NO: 30)
S11  Ac-Arg-cyclo[hCys-Ala-D-Phe-Arg-Trp-Pen]-NH₂ (SEQ ID NO: 31)
S12  Ac-Arg-cyclo[D-Pen-D-Ala-D-Phe-Arg-Trp-hCys]-NH₂ (SEQ ID NO: 30)
S13  Ac-Arg-cyclo[Cys-D-Ala-D-Phe-Arg-Trp-hCys]-NH₂ (SEQ ID NO: 33)
S14  Ac-Arg-cyclo[Pen-D-Ala-D-Phe-Arg-Trp-hCys]-NH₂ (SEQ ID NO: 34)
S15  Ac-Arg-cyclo[D-hCys-D-Ala-D-Phe-Arg-Trp-Cys]-NH₂ (SEQ ID NO: 35)
D1   Ac-Arg-cyclo[hCys-Pro-D-Phe-Arg-Trp-Cys]-NH₂ (SEQ ID NO: 36)
D2   Ac-Arg-cyclo[hCys-D-Pro-D-Phe-Arg-Trp-Cys]-NH₂ (SEQ ID NO: 37)
20   Ac-Arg-cyclo[Cys-Val-Gln-D-Phe-Arg-Trp-Cys]-NH₂ (SEQ ID NO: 38)
21   Ac-Arg-cyclo[Cys-D-Val-Gln-D-Phe-Arg-Trp-Cys]-NH₂ (SEQ ID NO: 39)
D3   Ac-Arg-cyclo[Cys-D-Val-His(1-Me)-D-Phe-Arg-Trp-Cys]-NH₂ (SEQ ID NO: 40)
D4   Ac-TzAla-cyclo[Cys-Ala-Gln-D-Phe-Arg-Trp-Cys]-NH2 (SEQ ID NO: 41)
TzAla = 3-(1,2,4-triazol-1-yl)-L- Ala

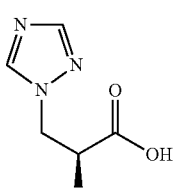

22  Ac-Glu-cyclo[Cys-Ala-His-D-Phe-Arg-Trp-Cys]-NH₂ (SEQ ID NO: 42)

23  (SEQ ID NO: 43)
Ac-Arg-Cys-D-Ala-D-His-D-Phe-Arg-Trp-Cys-OH 24  (SEQ ID NO: 44)
H-Arg-Cys-D-Ala-D-His-D-Phe-Arg-Trp-Cys-OH

TABLE 1-continued

Examples of Cationic Peptides of Formula I

| Compound | | (SEQ ID NO: 1) |
|---|---|---|
| Peptide 1 | Ac-Arg-Cys-D-Ala-D-His-D-Phe-Arg-Trp-Cys-NH$_2$ | |
| 25 | Ac-Arg-Cys-D-Ala-D-His-D-Phe-Arg-Trp-Cys-NH$_2$ | (SEQ ID NO: 45) |

Certain cationic polypeptides of Table 1 were tested to assess activity in the assays described below. The data is provided in Table 2.

Peptide Testing:

Radioligand Binding Assays:

Receptor binding assays for determining the binding constant ($K_d$) or inhibition concentration (IC$_{50}$) for displacing a radio-labeled ligand from the receptor of a cyclic peptide of the invention may be conducted by any means known in the art.

As an example, the cell membrane preparations for a binding assay are prepared from CHO-K1 cells transfected to stably express hMC receptor subtypes 1, 3, 4 or 5. Competitive inhibition of [$^{125}$I](Tyr$^2$)-(Nle$^4$-D-Phe$^7$)-alpha-MSH ([$^{125}$I]-NDP-α-MSH binding is carried out in polypropylene 96 well plates. Briefly, the cell membranes (1-10 μg protein/well), prepared as described above, is incubated in 50 mM Tris-HCl at pH 7.4 containing 0.2% BSA, 5 mM MgCl$_2$, 1 mM CaCl$_2$) and 0.1 mg/mL bacitracin, with increasing concentrations of the test compound and 0.1-0.3 nM [$^{125}$I]-NDP-α-MSH for approximately 120 minutes at 37° C. Bound [$^{125}$I]-NDP-α-MSH ligand is separated from free [$^{125}$I]-NDP-α-MSH by filtration through GF/C glass fiber filter plates (Unifilter®, Meriden, CT, USA) presoaked with 0.1% (w/v) polyethylenimine (PEI). Filters are washed three times with 50 mM Tris-HCl at pH 7.4 at a temperature of approximately 0-4° C. and then assayed for radioactivity. The binding data are analyzed by computer-assisted non-linear regression analysis.

Cyclic AMP Stimulation Assay:

Functional assays to determine agonist or antagonist status of a cyclic peptide of the invention may be conducted by any means known in the art.

Electrochemiluminescence (ECL) Assay

Stimulation of intracellular cyclic AMP (cAMP) levels by the peptides is determined in a dose dependent manner by an electrochemiluminescence (ECL) assay (Meso Scale Discovery, Gaithersburg, MD, USA; referred to hereinafter as "MSD"). Briefly, the CHO-K1 cells stably expressing the hMC receptor subtypes are suspended in RMPI 1640® assay buffer (RMPI 1640 buffer contains 0.5 mM IBMX, and 0.2% protein cocktail (MSD blocker A)). About 7,000 cells/well of the transgenic CHO-K1 cells stably expressing hMC receptor subtypes 1, 3, 4 or 5 are dispensed in 384-well Multi-Array plates (MSD) containing integrated carbon electrodes and coated with anti-cAMP antibody. Increasing concentrations of the test compounds are added and the cells are incubated for approximately 40 minutes at 37° C. A cell lysis buffer (HEPES-buffered saline solution with MgCl$_2$ and Triton X-100® at pH 7.3) containing 0.2% protein cocktail and 2.5 nM TAG™ ruthenium-labeled cAMP (MSD) is added and the cells are incubated for approximately 90 minutes at room temperature. At the end of the second incubation period, the read buffer (Tris-buffered solution containing an ECL co-reactant and Triton X-100 at pH 7.8) is added and the cAMP levels in the cell lysates are immediately determined by ECL detection with a Sector Imager 6000 Reader® (MSD). Data are analyzed using a computer-assisted non-linear regression analysis (XL fit; IDBS) and reported as either an EC$_{50}$ value. The EC$_{50}$ represents the concentration of an agonist compound needed to obtain 50% of the maximum reaction response, e.g., 50% of the maximum level of cAMP as determined using the assay described above.

cAMP Measurement Assay:

Human MC4-R transfected cells are grown to confluence in 96 well plates (plating approximately 250,000 cells per well). The cells are treated in triplicate sets with 0.2 mM isobutylmethylxanthine (IBMX) and graded concentrations of the peptide or alternatively the peptide in the presence of 20 nM NDP-MSH. Cells similarly treated but with only 20 nM NDP-MSH serve as positive controls in a volume of 200 μL. A buffer blank serving as a negative control is also included. After incubation of one hour at 37° C., the cells are lysed by the addition of 50 μL of a cell lysis buffer. Total cAMP accumulated in 250 μL of this incubation medium is quantitated using a commercially available low pH cAMP assay kit (Amersham BioSciences) as per procedure specified by the kit supplier. A peptide showing cAMP accumulation in the range same or higher than the alpha-MSH as positive control is considered to be an agonist. The data for agonist is plotted and curve fitted to determine the EC$_{50}$ value. A peptide showing accumulation in the same range as the negative control (buffer blank in the absence of alpha-MSH) is ineffective at the test concentration. A peptide showing attenuated accumulation is considered to be an antagonist if there is inhibition in cAMP when alpha-MSH is also present in the assay. Similar assay can be performed with hMC-1R, hMC-3R, and hMC-5R cells.

cAMP Accumulation Measurement via a β-galactosidase (β-Gal) Reporter System:

A chemiluminescence readout system that uses an enzyme fragment complementation (EFC) system with β-galactosidase (β-Gal) as the functional reporter system was used. This assay system for various melanocortin receptor systems is commercially available (cAMP Hunter GPCR assay system, Discoverx Corp, Fremont, CA). This assay utilizes the β-Gal enzyme that is split into two complementary portions; EA for Enzyme Acceptor and ED for Enzyme Donor. In the assay, the ED portion fused to cAMP is made to compete with cAMP generated by cells for binding to a cAMP-specific antibody. The EA is then added to form active β-Gal with any unbound ED-cAMP. This active enzyme then converts a chemiluminescent substrate to generate an output signal that is recorded on a standard microplate reader.

Briefly, 10000 cells per well are plated overnight and each well (cells incubated with 10 μl assay buffer) is then incubated with 4× serial concentration of the test compound in the cell assay buffer (5 μL) and cAMP antibody reagent (5 μL) for 30 min at 37° C. The cell lysis buffer (20 μL)

containing ED-cAMP coupled enzyme fragment and the reporter substrate (Emerald II-Galacton Star, 5:1) is then added and incubated for 60 min at room temperature. Next, 20 μL of EA β-Gal fragment reagent is added. After further incubation for 120 min at room temperature, the chemiluminescence is measured by a plate reader (Envision), and the data used to calculate $EC_{50}$ values for the test peptide.

The results are presented in Table 2.

was taken in a vial. The vial was stoppered, sealed and autoclaved for 15 min at 121° C. to give a uniform clear viscous solution. Upon cooling the vial was transferred to an aseptic flow hood. The vial was opened, and a sterile aqueous solution of Peptide 1 (30 mg in 0.5 mL), that was pre-filtered through a 0.2 μm filter, was mixed to it. The formulated peptide was obtained as a uniform clear viscous solution. The HPLC analysis assayed the Peptide 1 concentration of 6 mg/mL.

TABLE 2

EC50 (nM) values of example cationic polypeptides useful in the invention

| | cAMP Assay (EC-50) | | | | Ratios of EC50 values | | |
|---|---|---|---|---|---|---|---|
| Compound | MC1R | MC3R | MC4R | MC5R | MC1/4 | MC3/4 | MC5/4 |
| PEPTIDE 1 | 5.8 | 5.3 | 0.3 | 1600 | 20 | 20 | 5333 |
| 1 | 0.47 | 0.79 | 0.70 | 91 | 0.68 | 1.13 | 130 |
| 2 | 0.69 | 0.96 | 1 | 420 | 0.69 | 0.96 | 420 |
| 3 | 1 | 0.7 | 0.7 | 672 | 1 | 1 | 930 |
| 4 | 1.25 | 1.59 | 1.34 | 782 | 0.93 | 1.19 | 584 |
| 5 | 4.1 | 405.8 | 1.15 | 1085 | 4 | 350 | 945 |
| 6 | 30.4 | 4.3 | 0.7 | 467 | 40 | 6 | 662 |
| 7 | 273 | >10 uM | 34 | 259 | 8 | >290 | 7 |
| 8 | 71 | 8.6 | 1.6 | 255 | 40 | 5 | 155 |
| 9 | 248 | 81 | 3 | 1490 | 90 | 30 | 530 |
| 10 | 6.2 | 3.9 | 2.7 | | 2.31 | 1.45 | |
| 11 | 300.9 | >1000 | 45.1 | | 6.67 | >22.2 | |
| 12 | | | | | | | |
| 13 | 280 | >10 uM | 56 | 707 | 5 | >200 | 13 |
| 14 | 169 | >10 uM | 24 | 283 | 7 | >400 | 12 |
| 15 | 4 | 1 | 0.26 | 42 | 15 | 3.8 | 161 |
| 16 | 888 | 3158 | 7.5 | >10000 | 120 | 420 | >1338 |
| 17 | 195 | 233 | 13.7 | 2181 | 15 | 17 | 159 |
| 22 | 1.7 | 9.9 | <0.5 | 1282 | >3 | >20 | >2563 |

Preparation of the Ionic Complex and Pharmaceutical Composition of the Invention Example 1: Preparation of Formulation 2A (Peptide 1 and mPEG-10,000-Monocarboxylate)

A mixture of mPEG-10,000-mono-carboxylate (5.4 g) in 8.4 g of water was taken in a vial. The vial was stoppered, sealed and autoclaved for 15 min at 121° C. to give a uniform clear viscous solution. Upon cooling the vial was transferred to an aseptic flow hood. The vial was opened, and a sterile aqueous solution of Peptide 1 (100 mg in 1 mL), that was pre-filtered through a 0.2 μm filter, was mixed to it. The formulated peptide was obtained as a uniform clear viscous solution. The HPLC analysis assayed the Peptide 1 concentration of 9.9 mg/mL.

Example 2: Preparation of Formulation 2B (Peptide 1 and PEG-10,000-Dicarboxylate)

A mixture of PEG-10,000-dicarboxylate (2.7 g) in 2.0 g of water was taken in a vial. The vial was stoppered, sealed and autoclaved for 15 min at 121° C. to give a uniform clear viscous solution. Upon cooling the vial was transferred to an aseptic flow hood. The vial was opened, and a sterile aqueous solution of Peptide 1 (50 mg in 0.5 mL), that was pre-filtered through a 0.2 μm filter, was mixed to it. The formulated peptide was obtained as a uniform clear viscous solution. The HPLC analysis assayed the Peptide 1 concentration of 10.8 mg/mL.

Example 3: Preparation of Formulation 2C (Peptide 1 and mPEG-20,000-Mono-Carboxylate)

A mixture of PEG-m20,000-carboxylate (1.8 g) in 3.5 g of propylene glycol-ethanol-water mixture (40:15:45 ratio v/v)

Example 4: Preparation of Formulation 2D (Peptide 1 and Sodium DPPA)

A mixture of sodium DPPA (302 mg) in 8.6 g of 1:1 propylene glycol-water mixture was taken in a vial. The vial was stoppered, sealed and autoclaved for 15 min at 121° C. to yield a uniform lipid dispersion. Upon cooling the vial was transferred to an aseptic flow hood. The vial was opened, and a sterile aqueous solution of Peptide 1 (100 mg in 1 mL), that was pre-filtered through a 0.2 μm filter, was mixed to it. The formulated peptide was obtained as a uniform non-viscous dispersion. The HPLC analysis assayed the Peptide 1 concentration in the formulation of 9.6 mg/mL.

Example 5: Preparation of Formulation 2E (Peptide 1 and Sodium Stearate)

A mixture of mannitol (300 mg) and sodium stearate (165 mg) was taken in 8.3 g of water in a vial. The vial was stoppered and heated at 75° C. for 0.5 hour to give a clear solution. Upon cooling about 400 μL of 1.0N acetic acid was added to adjust pH to be within the 6-7 range. The vial was stoppered, sealed and autoclaved for 15 min at 121° C. Upon cooling the vial was transferred to an aseptic flow hood. The vial was opened, and a sterile aqueous solution of Peptide 1 (100 mg in 1.0 g aqueous solution), that was pre-filtered through a 0.2 μm filter, was mixed to it. The formulated peptide was obtained as a uniform light milky white opaque non-viscous suspension. The HPLC analysis assayed the Peptide 1 concentration of 9.7 mg/mL.

Example 6: Preparation of Formulation #3B (Peptide 1 with Sodium Stearate and mPEG-2,000-DSPE)

A mixture of mPEG-2000-DSPE (1.85 g) and sodium stearate (100.1 mg) taken in 10.8 mL of water in a vial. The vial was stoppered and heated at 75° C. for 1 hour. Upon cooling about 240 µL of acetic acid was added to adjust pH to be within the 6-7 range. The vial was stoppered, sealed and autoclaved for 15 min at 121° C. Upon cooling the vial was transferred to an aseptic flow hood. The vial was opened, and a sterile aqueous solution of Peptide 1 (120 mg in 1.2 g), that was pre-filtered through a 0.2 µm filter, was mixed to it. The formulated peptide was obtained as a uniform light milky white opaque non-viscous suspension. The HPLC analysis assayed the Peptide 1 concentration of 10.1 mg/mL.

Example 7: Preparation of Formulation #3C (Peptide 1 and Sodium DPPA and PEG-10,000-Dicarboxylate)

A mixture of PEG-10,000-dicarboxylate (1.68 g) and sodium DPPA (362.4 mg) taken in 9.1 mL of water in a vial. The vial was stoppered, sealed and autoclaved for 15 min at 121° C. to give a uniform milky white opaque suspension. Upon cooling the vial was transferred to an aseptic flow hood. The vial was opened, and a sterile aqueous solution of Peptide 1 (120 mg in 1.2 g), that was pre-filtered through a 0.2 µm filter, was mixed to it. The formulated peptide was obtained as a uniform milky white opaque suspension. The HPLC analysis assayed the Peptide 1 concentration of 10.6 mg/mL.

Example 8: Preparation of Formulation #3D (Peptide 1 and Sodium DPPA and PEG-3,350)

A mixture of PEG-3,350 (1.8 g contained in 10.8 mL aqueous solution) and sodium DPPA (363 mg) was taken in a vial. The vial was stoppered, sealed and autoclaved for 15 min at 121° C. to give a uniform milky white opaque suspension. Upon cooling the vial was transferred to an aseptic flow hood. The vial was opened, and a sterile aqueous solution of Peptide 1 (120 mg in 1.2 g), that was pre-filtered through a 0.2 µm filter, was mixed to it. The formulated peptide was obtained as a uniform milky white opaque suspension. The HPLC analysis assayed the Peptide 1 concentration of 10.1 mg/mL.

Example 9: Preparation of Formulation #3E (Peptide Land Sodium DPPA, PEG-3,350, and Sodium CMC)

An aqueous solution of sodium CMC (Av 1\4W 90,000), (72 mg in 9.0 mL) was mixed with PEG-3,350 (1.8 g). To the resulting clear solution sodium DPPA (216 mg) was added. The vial was stoppered, sealed and autoclaved for 15 min at 121° C. to give a uniform milky white opaque suspension. Upon cooling the vial was transferred to an aseptic flow hood. The vial was opened, and a sterile aqueous solution of Peptide 1 (120 mg in 1.2 g), that was pre-filtered through a 0.2 µm filter, was mixed to it. The formulated peptide was obtained as a uniform milky white opaque suspension. The HPLC analysis assayed the Peptide 1 concentration of 10.9 mg/mL.

Example 10: Preparation of Formulation #3F (Peptide 1 and mPEG-2,000-DSPE and Sodium CMC)

An aqueous solution of sodium CMC (Av 1\4W 90,000), (72 mg in 10.8 mL or 6.7 mg/mL) was mixed with mPEG-2,000-DSPE (1.85 g). The vial was stoppered, sealed and autoclaved for 15 min at 121° C. to give a uniform clear solution. Upon cooling the vial was transferred to an aseptic flow hood. Alternatively, the contents of the vial containing the mixture of sodium CMC and mPEG-2,000-DSPE were mixed overnight to give rise to a clear solution that was sterile filtered through a 0.2 µm filter. The vial was opened inside an aseptic flow hood, and a sterile aqueous solution of Peptide 1 (120 mg in 1.2 g), that was pre-filtered through a 0.2 µm filter, was mixed to it. The formulated peptide was obtained as a uniform clear solution. The HPLC analysis assayed the Peptide 1 concentration of 10.5 mg/mL.

Example 11: Preparation of Formulation #4B (Peptide 1 and mPEG-2,000-DSPE)

A mixture of mPEG-2,000-DSPE (1.855 g) and mannitol (181 mg) was taken in 8.8 mL of water for injection (nitrogen purged for 10 min) in a vial. The vial was stoppered and gently rotated to completely wet all the solid ingredients with water. It was then autoclaved for 15 min at 121° C. The contents of the vial at this stage were a clear solution. Upon cooling the vial was transferred to an aseptic flow hood. The vial was opened, and a sterile aqueous solution of Peptide 1 (120 mg in 1.2 g), that was pre-filtered through a 0.2 µm filter, was mixed to it for 1 h. The formulated peptide was obtained as a uniform clear solution. The HPLC analysis assayed the Peptide 1 concentration of 8.7 mg/mL.

Example 12: Preparation of Formulation #4C (Peptide 1 and mPEG-2,000-DSPE and CMC)

An aqueous solution of sodium CMC (Av MW 90,000), at a concentration of 8.9 mg/mL was prepared in nitrogen purged water for injection. To 9.8 mL of this solution taken in a vial was added mPEG-2,000-DSPE (1.853 g) and mannitol (182 mg). The vial was stoppered and gently rotated to completely wet all the solid ingredients with the solvent. It was then autoclaved for 15 min at 121° C. The contents of the vial at this stage were a clear solution. Upon cooling the vial was transferred to an aseptic flow hood. The vial was opened, and a sterile aqueous solution of Peptide 1 (120 mg in 1.2 g), that was pre-filtered through a 0.2 µm filter, was mixed to it for 1 h. The formulated peptide was obtained as a uniform clear solution. The HPLC analysis assayed the Peptide 1 concentration of 8.0 mg/mL.

Example 13: Preparation of Formulation #4D (Peptide 1 and mPEG-2,000-DSPE and DPPA)

A mixture of mPEG-2,000-DSPE (1.86 g), sodium DPPA (363 mg), and mannitol (60.2 mg) was taken in 9 mL of water for injection (nitrogen purged for 10 min) in a vial. The vial was stoppered and gently rotated to completely wet all the solid ingredients with water. It was then autoclaved for 15 min at 121° C. The contents of the vial at this stage were a light milky white homogenous suspension. Upon cooling the vial was transferred to an aseptic flow hood. The vial was opened, and a sterile aqueous solution of Peptide 1 (120 mg in 1.2 g), that was pre-filtered through a 0.2 µm filter, was mixed to it for 1 h to give a uniform light milky white opaque non-viscous suspension. The HPLC analysis assayed the Peptide 1 concentration of 9.2 mg/mL.

Example 14: Preparation of Formulation #4E (Peptide 1 and mPEG-2,000-DSPE and CMC)

An aqueous solution of sodium CMC at a concentration of 7.2 mg/mL was prepared in nitrogen purged water for injection. To 10 mL of this solution taken in a vial was added mPEG-2,000-DSPE (0.94 g) and mannitol (181.7 mg). The vial was stoppered and gently rotated to completely wet all the solid ingredients with the solvent. It was then autoclaved for 15 min at 121° C. The contents of the vial at this stage were a clear, colorless solution. Upon cooling the vial was transferred to an aseptic flow hood. The vial was opened, and a sterile aqueous solution of Peptide 1 (120 mg in 1.2 g), that was pre-filtered through a 0.2 µm filter, was mixed to it for 1 h. The formulated peptide was obtained as a uniform clear solution. The HPLC analysis assayed the Peptide 1 concentration of 9.6 mg/mL.

Example 15: Preparation of Formulation #4F (Peptide 1 and mPEG-2,000-DSPE and DPPA)

A mixture of mPEG-2,000-DSPE (0.954 g), sodium DPPA (183.7 mg), and mannitol (61.7 mg) was taken in 9.6 mL of water for injection (nitrogen purged for 10 min) in a vial. The vial was stoppered and gently rotated to completely wet all the solid ingredients with water. It was then autoclaved for 15 min at 121° C. The contents of the vial at this stage were a light milky white homogenous suspension. Upon cooling the vial was transferred to an aseptic flow hood. The vial was opened, and a sterile aqueous solution of Peptide 1 (120 mg in 1.2 g), that was pre-filtered through a 0.2 µm filter, was mixed to it for 1 h to obtain a uniform light milky white opaque non-viscous suspension. The HPLC analysis assayed the Peptide 1 concentration of 9.9 mg/mL.

Example 16: Preparation of Formulation Having Peptide 1, mPEG-2,000-DSPE, CMA and D-Mannitol

|  | Strength |
| --- | --- |
| Peptide 1 | 10 mg/mL* |
| mPEG2000-DSPE · Na | 100 mg/mL |
| CMC · Na (Av MW, 90K) | 8 mg/mL |
| D-Mannitol | 22 mg/mL |
| Water | As needed to 1 mL final volume |

*Based on peptide content

The following preparation is based on a 10 mL formulation and can be easily scaled down to provide the 1 mL final volume in the table above.

An aqueous solution of sodium CMC (Av 1\4W 90,000), (80 mg) and D-mannitol (220 mg) is taken in 7 ml of water for injection in a pre-weighed vial with a stir bar and stopper. To this solution solid sodium mPEG-2,000-DSPE (1 g) is added. The vial is stoppered, and sealed. It is placed in a water bath set at 60° C. and the contents stirred. Alternatively, the vial can be placed in an oven maintained at 60° C. Initially the contents of the vial may be cloudy, but will turn into a clear uniform solution within 1-2 hours. The vial is allowed to attain room temperature. It is then opened and an aqueous solution of Peptide 1 (100 mg in 1 mL, based on its net peptide content) is mixed into it. The contents may turn cloudy momentarily, but will turn into a clear homogenous solution upon mixing. The vial is weighed and the weight of the total contents adjusted to 10.1 gm by adding the required amount of water for injection solution. The resulting formulation is then mixed and filtered through a 0.2 µm filter inside an aseptic flow hood. The formulated peptide was obtained as a uniform clear solution and is assayed by HPLC to confirm the 10 mg/ml concentration of Peptide-1.

Example 17: Preparation of Formulation Having Peptide 1, Sodium DPPA, and PEG-3,350

|  | Strength |
| --- | --- |
| Peptide 1 | 10 mg/mL* |
| DPPA · Na | 30.2 mg/mL |
| PEG-3350 | 120 mg/mL |
| Water | As need to 1 mL final volume |

*Based on peptide content

The following preparation is based on a 10 mL formulation and can be easily scaled down to provide the 1 mL final volume in the table above.

In a pre-weighed stoppered vial is added 1.2 gm of PEG-3350 and 8 mL of water for injection. The contents are dissolved by mixing and 302 mg of sodium DPPA is added. The vial is stoppered, sealed and placed in an autoclave autoclaved for 15 min at 121° C. to give a uniform milky white opaque suspension. Upon cooling the vial is transferred to an aseptic flow hood. The vial is opened, and a sterile aqueous solution of Peptide 1 (100 mg in 1 mL water, based on its net peptide content), that was pre-filtered through a 0.2 µm filter, is mixed to it. The total content of vial is adjusted to 10.1 gm by the addition of appropriate amount of water for injection. Upon mixing, the formulated peptide is obtained as a uniform milky white opaque suspension. The formulated peptide is assayed by HPLC to confirm the 10 mg/ml concentration of Peptide-1.

Figure 2:
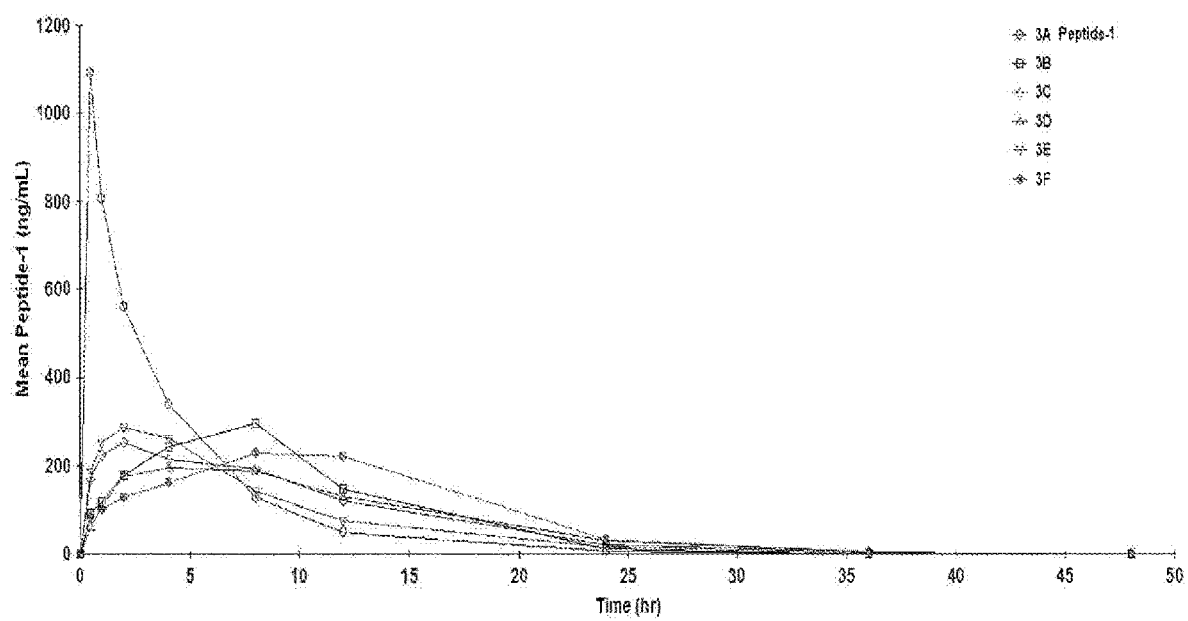
FIG. 2 is a graph showing the pharmacokinetic profile of each of the identified pharmaceutical compositions following administration to cynomolgous monkeys.
Figure 3:
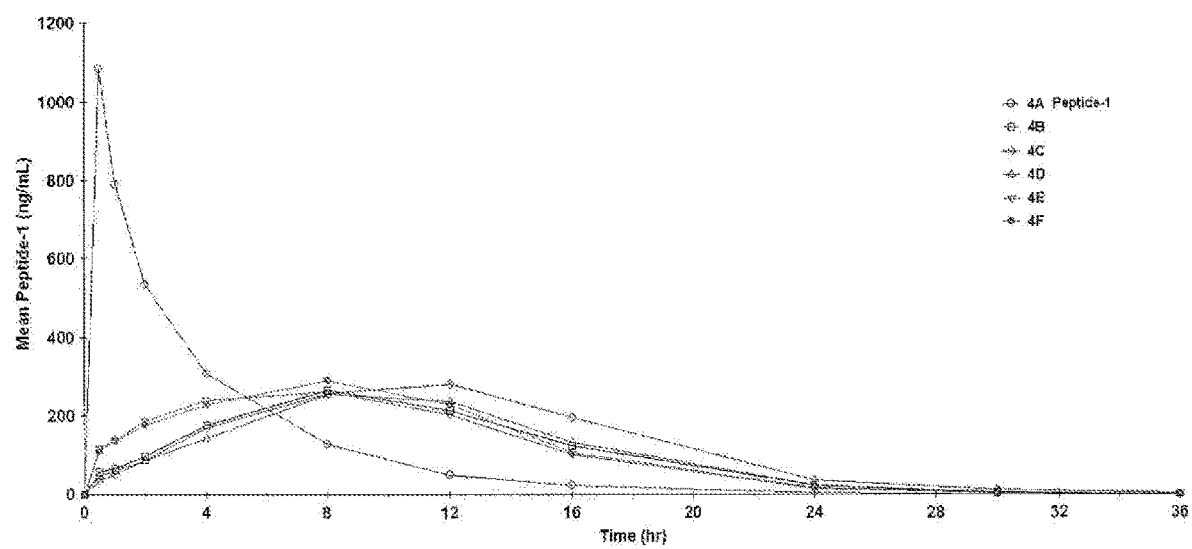
FIG. 3 is a graph showing the pharmacokinetic profile of each of the identified pharmaceutical compositions following administration to cynomologous monkeys.

Example 18: Administration of Formulations to Cynomolgus Monkeys to Evaluate Pharmacokinetics A group of Cynomolgus monkeys (average body weight range of 3 to 7 kg) were randomized into a group of 6 for each formulation described above and for Formulation 3A. Each monkey in the cohort was subcutaneously administered in the scapular area with a single bolus dose of a formulation calculated at 0.5 mg/kg body weight. Blood samples were taken at various time points staring at 30 minutes post dosing to 36 or 48 hours. The plasma was harvested and peptide drug concentration assays using LC-MS/MS technique. The pharmacokinetic data is presented in Table 3 below, and the pharmacokinetic profile is set forth graphically in FIG. 1, FIG. 2, and FIG. 3.

TABLE 3

Pharmacokinetic Data for Formulations (N = 6; Dose = 0.5 mg/Kg Control formulations contain Peptide 1 in citrate buffer)

| Formulation Description | Cmax (ng/mL) | Tmax (hr) | AUC last (hr * ng/mL) | T-1/2 (hr) | % Fr |
|---|---|---|---|---|---|
| CONTROL; SC formulation-Citrate: | | | | | |
| SC Control-D27455, (Citrate) 4A 10 mg/ml | 1080 ± 210 | 0.50 ± 0 | 3680 ± 850 | 3.55 ± 0.536 | 100 |
| SC Control-D27455, (Citrate) 3A 10 mg/ml | 1100 ± 101 | 0.50 ± 0 | 3970 ± 777 | 3.50 ± 0.48 | 100 |
| Group: 2 | | | | | |
| PEPTIDE 1 AND mPEG-COOH-10K 2A | 438 ± 62 | 2.17 ± 0.98 | 3140 ± 295 | 3.64 ± 0.134 | 85.3* |
| PEPTIDE 1 AND PEG-(COOH)2-10K 2B | 472 ± 125 | 2.33 ± 0.82 | 3830 ± 1090 | 3.85 ± 1.27 | 104 * |
| PEPTIDE 1 AND mPEG-COOH-20K 2C | 443 ± 116 | 3.33 ± 1.03 | 4240 ± 902 | 4.13 ± 0.536 | 115 * |
| PEPTIDE 1 AND DPPA/PG (PG is propylene glycol as solvent) 2D | 351 ± 30.4 | 1.0 ± 0.55 | 3530 ± 696 | 6.81 ± 1.17 | 96 * |
| PEPTIDE 1 AND Na · stearate 2E | 838 ± 73 | 0.5 ± 0.0 | 2800 ± 281 | 3.46 ± 0.798 | 76 * |
| Group: 3 | | | | | |
| PEPTIDE 1, Na·Stearate, AND mPEG-DSPE 3B | 303 ± 26.4 | 7.33 ± 1.63 | 3640 ± 608 | — | 91.7 |
| PEG-(COOH)2-10K/Na · DPPA AND PEPTEDE 1 3C | 272 ± 52.4 | 2.00 ± 0 | 3330 ± 707 | 4.47 ± 1.07 | 83.9 |
| PEG3350/Na · DPPA AND PEPTEDE 1 3D | 228 ± 50 | 4.33 ± 1.97 | 3180 ± 542 | 1.07 ± 0.15 | 80.1 |
| PEG3350, CMC, sodium DPPA AND PEPTIDE 1 3E | 317 ± 68.4 | 2.50 ± 1.22 | 2890 ± 266 | 4.49 ± 0.80 | 72.8 |
| CMC/mPEG-DSPE AND PEPTIDE 1 3F | 258 ± 77.8 | 10.0 ± 2.19 | 3990 ± 788 | 4.53 ± 0 | 100.5 |
| Group: 4 | | | | | |
| mPEG-DSPE AND PEPTIDE 1, 4B | 270 ± 53.5 | 8.67 ± 3.01 | 3570 ± 550 | 3.36 ± 0.654 | 96.7 |
| mPEG-DSPE/CMC AND PEPTIDE 1, 4C | 320 ± 49.9 | 11.3 ± 3.01 | 4340 ± 353 | 3.79 ± 0.503 | 117 |
| mPEG-DSPE/DPPA AND PEPTIDE 1, 4D | 283 ± 72.4 | 9.33 ± 2.07 | 3570 ± 789 | 3.09 ± 0.304 | 96.6 |
| mPEG-DSPE/CMC AND PEPTIDE 1, 4E | 292 ± 38.0 | 8.00 ± 3.03 | 3710 ± 531 | 3.05 ± 0.304 | 100 |
| mPEG-DSPE/DPPA AND PEPTEDE 1 4F | 302 ± 24.2 | 8.00 ± 2.53 | 3940 ± 242 | 3.25 ± 0.352 | 106.5 |

* % Fr represents the bioavailability of a formulation when compared to the Control 4A.

As is evident from the results of comparative pharmacokinetic studies with the exemplified ionic-complexes of Peptide-1, there was significant reduction in the C-max (Peptide 1 Cmax of 1100 ng/mL vs 228 ng/mL observed with complex 3D). Many other ionic complexes of this invention displayed similar range of blunted C-max as compared to Peptide-1. In addition to this, the T-max was also significantly increase with several of these ionic complexes (T-max of Peptide-1 was 0.5 hrs vs. T-max of several hours with many of the ionic complexes).

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. An ionic complex comprising:
   (i) a cationic polypeptide represented by the following structural formula:

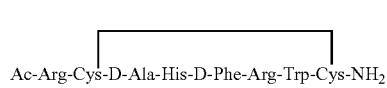

(SEQ ID NO: 1)

or a pharmaceutically acceptable salt thereof; and
   (ii) a 1,2-distearoyl-sn-glycero-3-phosphoethanolamine (DSPE) conjugated polyethylene glycol,
   wherein the molar ratio of the cationic polypeptide to the 1,2-distearoyl-sn-glycero-3-phosphoethanolamine (DSPE) conjugated polyethylene glycol ranges from about 1:1 to about 1:10.

2. The ionic complex of claim 1, wherein the molar ratio of the cationic peptide to the 1,2-distearoyl-sn-glycero-3-phosphoethanolamine (DSPE) conjugated polyethylene glycol ranges from about 1:2 to about 1:8.

3. The ionic complex of claim 1, wherein the molar ratio of the cationic peptide to the 1,2-distearoyl-sn-glycero-3-phosphoethanolamine (DSPE) conjugated polyethylene glycol ranges from about 1:3 to about 1:6.

4. The ionic complex of claim 1, further comprising an anionic excipient selected from carboxymethylcellulose (CMC), stearic acid, and DPPA.

5. The ionic complex of claim 4, wherein the anionic excipient is CMC.

6. The ionic complex of claim 1, wherein the 1,2-distearoyl-sn-glycero-3-phosphoethanolamine (DSPE) conjugated polyethylene glycol is selected from mPEG-2,000-DSPE and mPEG-5,000-DSPE.

7. The ionic complex of claim 6, wherein the 1,2-distearoyl-sn-glycero-3-phosphoethanolamine (DSPE) conjugated polyethylene glycol is mPEG-2,000-DSPE.

8. The ionic complex of claim 1, further comprising a combination of anionic excipients.

9. The ionic complex of claim 8, wherein the combination of anionic excipients is selected from: stearic acid and mPEG-2,000-DSPE; DPPA and mPEG-2,000-DSPE; mPEG-2,000-DSPE and CMC; and mPEG-2,000-DSPE.

10. The ionic complex of claim 1, wherein the ionic complex has the property that it forms a drug depot in a physiological environment.

11. The ionic complex of claim 1, wherein the ionic complex has the property that it forms a drug depot when delivered subcutaneously.

* * * * *

SEQUENCE LISTING

<160> NUMBER OF SEQ ID NOS: 89

<210> SEQ ID NO 1
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: misc_feature
<222> LOCATION: (2)..(8)
<223> OTHER INFORMATION: /note="Cyclic peptide"
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (5)..(5)
<223> OTHER INFORMATION: D-amino acid
<220> FEATURE:
<221> NAME/KEY: source
<223> OTHER INFORMATION: /note="C-term NH2"

<400> SEQUENCE: 1

Arg Cys Ala His Phe Arg Trp Cys
1               5

<210> SEQ ID NO 2
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: misc_feature
<222> LOCATION: (2)..(8)
<223> OTHER INFORMATION: /note="Cyclic peptide"
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (5)..(5)
<223> OTHER INFORMATION: D-amino acid
<220> FEATURE:
<221> NAME/KEY: source
<223> OTHER INFORMATION: /note="C-term NH2"

<400> SEQUENCE: 2

Arg Cys Leu His Phe Arg Trp Cys
1               5

<210> SEQ ID NO 3
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source

```
<223> OTHER INFORMATION: /note="N-term Ac"
<220> FEATURE:
<221> NAME/KEY: misc_feature
<222> LOCATION: (2)..(8)
<223> OTHER INFORMATION: /note="Cyclic peptide"
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (5)..(5)
<223> OTHER INFORMATION: D-amino acid
<220> FEATURE:
<221> NAME/KEY: source
<223> OTHER INFORMATION: /note="C-term NH2"

<400> SEQUENCE: 3

Arg Cys Ile His Phe Arg Trp Cys
1               5

<210> SEQ ID NO 4
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: misc_feature
<222> LOCATION: (2)..(8)
<223> OTHER INFORMATION: /note="Cyclic peptide"
<220> FEATURE:
<221> NAME/KEY: MOD_RES
<222> LOCATION: (3)..(3)
<223> OTHER INFORMATION: D-Tert-Leu (D-Tert-butyl-Gly)
<220> FEATURE:
<221> NAME/KEY: MOD_RES
<222> LOCATION: (5)..(5)
<223> OTHER INFORMATION: D-amino acid
<220> FEATURE:
<221> NAME/KEY: source
<223> OTHER INFORMATION: /note="C-term NH2"

<400> SEQUENCE: 4

Arg Cys Xaa His Phe Arg Trp Cys
1               5

<210> SEQ ID NO 5
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: misc_feature
<222> LOCATION: (2)..(8)
<223> OTHER INFORMATION: /note="Cyclic peptide"
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (5)..(5)
<223> OTHER INFORMATION: D-amino acid
```

```
<220> FEATURE:
<221> NAME/KEY: source
<223> OTHER INFORMATION: /note="C-term NH2"

<400> SEQUENCE: 5

Arg Cys Val His Phe Arg Trp Cys
1               5

<210> SEQ ID NO 6
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: misc_feature
<222> LOCATION: (2)..(8)
<223> OTHER INFORMATION: /note="Cyclic peptide"
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (4)..(4)
<223> OTHER INFORMATION: 3-Methyl-His
<220> FEATURE:
<221> NAME/KEY: MOD_RES
<222> LOCATION: (5)..(5)
<223> OTHER INFORMATION: D-amino acid
<220> FEATURE:
<221> NAME/KEY: source
<223> OTHER INFORMATION: /note="C-term NH2"

<400> SEQUENCE: 6

Arg Cys Ala His Phe Arg Trp Cys
1               5

<210> SEQ ID NO 7
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: misc_feature
<222> LOCATION: (2)..(8)
<223> OTHER INFORMATION: /note="Cyclic peptide"
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (4)..(4)
<223> OTHER INFORMATION: 1-Methyl-His
<220> FEATURE:
<221> NAME/KEY: MOD_RES
<222> LOCATION: (5)..(5)
<223> OTHER INFORMATION: D-amino acid
<220> FEATURE:
<221> NAME/KEY: source
<223> OTHER INFORMATION: /note="C-term NH2"

<400> SEQUENCE: 7
```

Arg Cys Ala His Phe Arg Trp Cys
1               5

<210> SEQ ID NO 8
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: misc_feature
<222> LOCATION: (2)..(8)
<223> OTHER INFORMATION: /note="Cyclic peptide"
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (5)..(5)
<223> OTHER INFORMATION: D-amino acid
<220> FEATURE:
<221> NAME/KEY: source
<223> OTHER INFORMATION: /note="C-term NH2"

<400> SEQUENCE: 8

Arg Cys Ala Trp Phe Arg Trp Cys
1               5

<210> SEQ ID NO 9
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: misc_feature
<222> LOCATION: (2)..(8)
<223> OTHER INFORMATION: /note="Cyclic peptide"
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (5)..(5)
<223> OTHER INFORMATION: D-amino acid
<220> FEATURE:
<221> NAME/KEY: source
<223> OTHER INFORMATION: /note="C-term NH2"

<400> SEQUENCE: 9

Arg Cys Ala Gln Phe Arg Trp Cys
1               5

<210> SEQ ID NO 10
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<220> FEATURE:
<221> NAME/KEY: source
<223> OTHER INFORMATION: /note="N-term Ac"
<220> FEATURE:
<221> NAME/KEY: misc_feature
<222> LOCATION: (2)..(8)
<223> OTHER INFORMATION: /note="Cyclic peptide"
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (5)..(5)
<223> OTHER INFORMATION: D-amino acid
<220> FEATURE:
<221> NAME/KEY: source
<223> OTHER INFORMATION: /note="C-term NH2"

<400> SEQUENCE: 10

Arg Cys Ala Asn Phe Arg Trp Cys
1               5

<210> SEQ ID NO 11
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: misc_feature
<222> LOCATION: (2)..(8)
<223> OTHER INFORMATION: /note="Cyclic peptide"
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (5)..(5)
<223> OTHER INFORMATION: D-amino acid
<220> FEATURE:
<221> NAME/KEY: source
<223> OTHER INFORMATION: /note="C-term NH2"

<400> SEQUENCE: 11

Arg Cys Ala Arg Phe Arg Trp Cys
1               5

<210> SEQ ID NO 12
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: misc_feature
<222> LOCATION: (2)..(8)
<223> OTHER INFORMATION: /note="Cyclic peptide"
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
```

```
<222> LOCATION: (5)..(5)
<223> OTHER INFORMATION: D-amino acid
<220> FEATURE:
<221> NAME/KEY: source
<223> OTHER INFORMATION: /note="C-term NH2"

<400> SEQUENCE: 12

Arg Cys Ala Tyr Phe Arg Trp Cys
1               5

<210> SEQ ID NO 13
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: misc_feature
<222> LOCATION: (2)..(8)
<223> OTHER INFORMATION: /note="Cyclic peptide"
<220> FEATURE:
<221> NAME/KEY: MOD_RES
<222> LOCATION: (3)..(5)
<223> OTHER INFORMATION: D-amino acid
<220> FEATURE:
<221> NAME/KEY: source
<223> OTHER INFORMATION: /note="C-term NH2"

<400> SEQUENCE: 13

Arg Cys Ala Pro Phe Arg Trp Cys
1               5

<210> SEQ ID NO 14
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: misc_feature
<222> LOCATION: (2)..(8)
<223> OTHER INFORMATION: /note="Cyclic peptide"
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (5)..(5)
<223> OTHER INFORMATION: D-amino acid
<220> FEATURE:
<221> NAME/KEY: source
<223> OTHER INFORMATION: /note="C-term NH2"

<400> SEQUENCE: 14

Arg Cys Ala Pro Phe Arg Trp Cys
1               5

<210> SEQ ID NO 15
<211> LENGTH: 8
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: misc_feature
<222> LOCATION: (2)..(8)
<223> OTHER INFORMATION: /note="Cyclic peptide"
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (5)..(5)
<223> OTHER INFORMATION: 4-fluoro-D-Phe
<220> FEATURE:
<221> NAME/KEY: source
<223> OTHER INFORMATION: /note="C-term NH2"

<400> SEQUENCE: 15

Arg Cys Ala Pro Phe Arg Trp Cys
1               5

<210> SEQ ID NO 16
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: misc_feature
<222> LOCATION: (2)..(8)
<223> OTHER INFORMATION: /note="Cyclic peptide"
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (4)..(4)
<223> OTHER INFORMATION: 2-aminotetralin-2-carboxylic acid
<220> FEATURE:
<221> NAME/KEY: MOD_RES
<222> LOCATION: (5)..(5)
<223> OTHER INFORMATION: D-amino acid
<220> FEATURE:
<221> NAME/KEY: source
<223> OTHER INFORMATION: /note="C-term NH2"

<400> SEQUENCE: 16

Arg Cys Ala Xaa Phe Arg Trp Cys
1               5

<210> SEQ ID NO 17
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: misc_feature
<222> LOCATION: (2)..(8)
```

```
<223> OTHER INFORMATION: /note="Cyclic peptide"
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (4)..(4)
<223> OTHER INFORMATION: Quinolinyl-Ala (2-amino-3-(quinolin-3-
      yl)propanoic acid)
<220> FEATURE:
<221> NAME/KEY: MOD_RES
<222> LOCATION: (5)..(5)
<223> OTHER INFORMATION: D-amino acid
<220> FEATURE:
<221> NAME/KEY: source
<223> OTHER INFORMATION: /note="C-term NH2"

<400> SEQUENCE: 17

Arg Cys Ala Ala Phe Arg Trp Cys
1               5

<210> SEQ ID NO 18
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: misc_feature
<222> LOCATION: (2)..(8)
<223> OTHER INFORMATION: /note="Cyclic peptide"
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (4)..(4)
<223> OTHER INFORMATION: 1-amino-4-phenylcyclohexane-1-carboxylic acid
<220> FEATURE:
<221> NAME/KEY: MOD_RES
<222> LOCATION: (5)..(5)
<223> OTHER INFORMATION: D-amino acid
<220> FEATURE:
<221> NAME/KEY: source
<223> OTHER INFORMATION: /note="C-term NH2"

<400> SEQUENCE: 18

Arg Cys Ala Xaa Phe Arg Trp Cys
1               5

<210> SEQ ID NO 19
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: misc_feature
<222> LOCATION: (2)..(8)
<223> OTHER INFORMATION: /note="Cyclic peptide"
<220> FEATURE:
<221> NAME/KEY: MOD_RES
<222> LOCATION: (3)..(3)
```

```
<223> OTHER INFORMATION: D-amino acid
<220> FEATURE:
<221> NAME/KEY: MOD_RES
<222> LOCATION: (4)..(4)
<223> OTHER INFORMATION: 2-amino-3-(1H-pyrazol-1-yl)propanoic acid
<220> FEATURE:
<221> NAME/KEY: MOD_RES
<222> LOCATION: (5)..(5)
<223> OTHER INFORMATION: D-amino acid
<220> FEATURE:
<221> NAME/KEY: source
<223> OTHER INFORMATION: /note="C-term NH2"

<400> SEQUENCE: 19

Arg Cys Ala Xaa Phe Arg Trp Cys
1               5

<210> SEQ ID NO 20
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: misc_feature
<222> LOCATION: (2)..(7)
<223> OTHER INFORMATION: /note="Cyclic peptide"
<220> FEATURE:
<221> NAME/KEY: MOD_RES
<222> LOCATION: (2)..(2)
<223> OTHER INFORMATION: homoCys
<220> FEATURE:
<221> NAME/KEY: MOD_RES
<222> LOCATION: (4)..(4)
<223> OTHER INFORMATION: D-amino acid
<220> FEATURE:
<221> NAME/KEY: source
<223> OTHER INFORMATION: /note="C-term NH2"

<400> SEQUENCE: 20

Arg Cys Ala Phe Arg Trp Cys
1               5

<210> SEQ ID NO 21
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: misc_feature
<222> LOCATION: (2)..(7)
<223> OTHER INFORMATION: /note="Cyclic peptide"
<220> FEATURE:
<221> NAME/KEY: MOD_RES
<222> LOCATION: (2)..(2)
<223> OTHER INFORMATION: homoCys
<220> FEATURE:
<221> NAME/KEY: MOD_RES
<222> LOCATION: (3)..(4)
<223> OTHER INFORMATION: D-amino acid
<220> FEATURE:
<221> NAME/KEY: source
<223> OTHER INFORMATION: /note="C-term NH2"
```

```
<400> SEQUENCE: 21

Arg Cys Ala Phe Arg Trp Cys
1               5

<210> SEQ ID NO 22
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: misc_feature
<222> LOCATION: (2)..(7)
<223> OTHER INFORMATION: /note="Cyclic peptide"
<220> FEATURE:
<221> NAME/KEY: MOD_RES
<222> LOCATION: (2)..(2)
<223> OTHER INFORMATION: homoCys
<220> FEATURE:
<221> NAME/KEY: MOD_RES
<222> LOCATION: (3)..(4)
<223> OTHER INFORMATION: D-amino acid
<220> FEATURE:
<221> NAME/KEY: MOD_RES
<222> LOCATION: (7)..(7)
<223> OTHER INFORMATION: Penicillamine
<220> FEATURE:
<221> NAME/KEY: source
<223> OTHER INFORMATION: /note="C-term NH2"

<400> SEQUENCE: 22

Arg Cys Ala Phe Arg Trp Xaa
1               5

<210> SEQ ID NO 23
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: misc_feature
<222> LOCATION: (2)..(7)
<223> OTHER INFORMATION: /note="Cyclic peptide"
<220> FEATURE:
<221> NAME/KEY: MOD_RES
<222> LOCATION: (3)..(4)
<223> OTHER INFORMATION: D-amino acid
<220> FEATURE:
<221> NAME/KEY: MOD_RES
<222> LOCATION: (7)..(7)
<223> OTHER INFORMATION: 2,3-diaminopropionic acid
<220> FEATURE:
<221> NAME/KEY: source
<223> OTHER INFORMATION: /note="C-term NH2"

<400> SEQUENCE: 23

Arg Glu Ala Phe Arg Trp Xaa
1               5

<210> SEQ ID NO 24
<211> LENGTH: 7
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: misc_feature
<222> LOCATION: (2)..(7)
<223> OTHER INFORMATION: /note="Cyclic peptide"
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (7)..(7)
<223> OTHER INFORMATION: 2,3-diaminopropionic acid
<220> FEATURE:
<221> NAME/KEY: source
<223> OTHER INFORMATION: /note="C-term NH2"

<400> SEQUENCE: 24

Arg Glu Ala Phe Arg Trp Xaa
1               5

<210> SEQ ID NO 25
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: MOD_RES
<222> LOCATION: (2)..(2)
<223> OTHER INFORMATION: homoCys
<220> FEATURE:
<221> NAME/KEY: misc_feature
<222> LOCATION: (2)..(7)
<223> OTHER INFORMATION: /note="Cyclic peptide"
<220> FEATURE:
<221> NAME/KEY: MOD_RES
<222> LOCATION: (3)..(3)
<223> OTHER INFORMATION: Alpha-aminoisobutyric acid
<220> FEATURE:
<221> NAME/KEY: MOD_RES
<222> LOCATION: (4)..(4)
<223> OTHER INFORMATION: D-amino acid
<220> FEATURE:
<221> NAME/KEY: source
<223> OTHER INFORMATION: /note="C-term NH2"

<400> SEQUENCE: 25

Arg Cys Xaa Phe Arg Trp Cys
1               5

<210> SEQ ID NO 26
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
```

```
<221> NAME/KEY: MOD_RES
<222> LOCATION: (2)..(2)
<223> OTHER INFORMATION: homoCys
<220> FEATURE:
<221> NAME/KEY: misc_feature
<222> LOCATION: (2)..(7)
<223> OTHER INFORMATION: /note="Cyclic peptide"
<220> FEATURE:
<221> NAME/KEY: MOD_RES
<222> LOCATION: (3)..(3)
<223> OTHER INFORMATION: Sarcosine (N-methyl-Gly)
<220> FEATURE:
<221> NAME/KEY: MOD_RES
<222> LOCATION: (4)..(4)
<223> OTHER INFORMATION: D-amino acid
<220> FEATURE:
<221> NAME/KEY: source
<223> OTHER INFORMATION: /note="C-term NH2"

<400> SEQUENCE: 26

Arg Cys Xaa Phe Arg Trp Cys
1               5

<210> SEQ ID NO 27
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: MOD_RES
<222> LOCATION: (2)..(2)
<223> OTHER INFORMATION: homoCys
<220> FEATURE:
<221> NAME/KEY: misc_feature
<222> LOCATION: (2)..(7)
<223> OTHER INFORMATION: /note="Cyclic peptide"
<220> FEATURE:
<221> NAME/KEY: MOD_RES
<222> LOCATION: (4)..(4)
<223> OTHER INFORMATION: D-amino acid
<220> FEATURE:
<221> NAME/KEY: source
<223> OTHER INFORMATION: /note="C-term NH2"

<400> SEQUENCE: 27

Arg Cys Val Phe Arg Trp Cys
1               5

<210> SEQ ID NO 28
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: MOD_RES
<222> LOCATION: (2)..(2)
<223> OTHER INFORMATION: homoCys
<220> FEATURE:
<221> NAME/KEY: misc_feature
<222> LOCATION: (2)..(7)
<223> OTHER INFORMATION: /note="Cyclic peptide"
<220> FEATURE:
<221> NAME/KEY: MOD_RES
```

```
<222> LOCATION: (3)..(4)
<223> OTHER INFORMATION: D-amino acid
<220> FEATURE:
<221> NAME/KEY: source
<223> OTHER INFORMATION: /note="C-term NH2"

<400> SEQUENCE: 28

Arg Cys Val Phe Arg Trp Cys
1               5

<210> SEQ ID NO 29
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: MOD_RES
<222> LOCATION: (2)..(2)
<223> OTHER INFORMATION: homoCys
<220> FEATURE:
<221> NAME/KEY: misc_feature
<222> LOCATION: (2)..(7)
<223> OTHER INFORMATION: /note="Cyclic peptide"
<220> FEATURE:
<221> NAME/KEY: MOD_RES
<222> LOCATION: (4)..(4)
<223> OTHER INFORMATION: D-amino acid
<220> FEATURE:
<221> NAME/KEY: source
<223> OTHER INFORMATION: /note="C-term NH2"

<400> SEQUENCE: 29

Arg Cys Gln Phe Arg Trp Cys
1               5

<210> SEQ ID NO 30
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: MOD_RES
<222> LOCATION: (2)..(2)
<223> OTHER INFORMATION: homoCys
<220> FEATURE:
<221> NAME/KEY: misc_feature
<222> LOCATION: (2)..(7)
<223> OTHER INFORMATION: /note="Cyclic peptide"
<220> FEATURE:
<221> NAME/KEY: MOD_RES
<222> LOCATION: (3)..(4)
<223> OTHER INFORMATION: D-amino acid
<220> FEATURE:
<221> NAME/KEY: source
<223> OTHER INFORMATION: /note="C-term NH2"

<400> SEQUENCE: 30

Arg Cys Gln Phe Arg Trp Cys
1               5

<210> SEQ ID NO 31
```

```
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: MOD_RES
<222> LOCATION: (2)..(2)
<223> OTHER INFORMATION: homoCys
<220> FEATURE:
<221> NAME/KEY: misc_feature
<222> LOCATION: (2)..(7)
<223> OTHER INFORMATION: /note="Cyclic peptide"
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (7)..(7)
<223> OTHER INFORMATION: Penicillamine
<220> FEATURE:
<221> NAME/KEY: source
<223> OTHER INFORMATION: /note="C-term NH2"

<400> SEQUENCE: 31

Arg Cys Ala Phe Arg Trp Xaa
1               5

<210> SEQ ID NO 32
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: MOD_RES
<222> LOCATION: (2)..(2)
<223> OTHER INFORMATION: D-Penicillamine
<220> FEATURE:
<221> NAME/KEY: misc_feature
<222> LOCATION: (2)..(7)
<223> OTHER INFORMATION: /note="Cyclic peptide"
<220> FEATURE:
<221> NAME/KEY: MOD_RES
<222> LOCATION: (3)..(4)
<223> OTHER INFORMATION: D-amino acid
<220> FEATURE:
<221> NAME/KEY: MOD_RES
<222> LOCATION: (7)..(7)
<223> OTHER INFORMATION: homoCys
<220> FEATURE:
<221> NAME/KEY: source
<223> OTHER INFORMATION: /note="C-term NH2"

<400> SEQUENCE: 32

Arg Xaa Ala Phe Arg Trp Cys
1               5

<210> SEQ ID NO 33
<211> LENGTH: 7
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: misc_feature
<222> LOCATION: (2)..(7)
<223> OTHER INFORMATION: /note="Cyclic peptide"
<220> FEATURE:
<221> NAME/KEY: MOD_RES
<222> LOCATION: (3)..(4)
<223> OTHER INFORMATION: D-amino acid
<220> FEATURE:
<221> NAME/KEY: MOD_RES
<222> LOCATION: (7)..(7)
<223> OTHER INFORMATION: homoCys
<220> FEATURE:
<221> NAME/KEY: source
<223> OTHER INFORMATION: /note="C-term NH2"

<400> SEQUENCE: 33

Arg Cys Ala Phe Arg Trp Cys
1               5

<210> SEQ ID NO 34
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: MOD_RES
<222> LOCATION: (2)..(2)
<223> OTHER INFORMATION: Penicillamine
<220> FEATURE:
<221> NAME/KEY: misc_feature
<222> LOCATION: (2)..(7)
<223> OTHER INFORMATION: /note="Cyclic peptide"
<220> FEATURE:
<221> NAME/KEY: MOD_RES
<222> LOCATION: (3)..(4)
<223> OTHER INFORMATION: D-amino acid
<220> FEATURE:
<221> NAME/KEY: MOD_RES
<222> LOCATION: (7)..(7)
<223> OTHER INFORMATION: homoCys
<220> FEATURE:
<221> NAME/KEY: source
<223> OTHER INFORMATION: /note="C-term NH2"

<400> SEQUENCE: 34

Arg Xaa Ala Phe Arg Trp Cys
1               5

<210> SEQ ID NO 35
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: MOD_RES
<222> LOCATION: (2)..(2)
<223> OTHER INFORMATION: D-homoCys
```

```
<220> FEATURE:
<221> NAME/KEY: misc_feature
<222> LOCATION: (2)..(7)
<223> OTHER INFORMATION: /note="Cyclic peptide"
<220> FEATURE:
<221> NAME/KEY: MOD_RES
<222> LOCATION: (3)..(4)
<223> OTHER INFORMATION: D-amino acid
<220> FEATURE:
<221> NAME/KEY: source
<223> OTHER INFORMATION: /note="C-term NH2"

<400> SEQUENCE: 35

Arg Cys Ala Phe Arg Trp Cys
1               5

<210> SEQ ID NO 36
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: MOD_RES
<222> LOCATION: (2)..(2)
<223> OTHER INFORMATION: homoCys
<220> FEATURE:
<221> NAME/KEY: misc_feature
<222> LOCATION: (2)..(7)
<223> OTHER INFORMATION: /note="Cyclic peptide"
<220> FEATURE:
<221> NAME/KEY: MOD_RES
<222> LOCATION: (4)..(4)
<223> OTHER INFORMATION: D-amino acid
<220> FEATURE:
<221> NAME/KEY: source
<223> OTHER INFORMATION: /note="C-term NH2"

<400> SEQUENCE: 36

Arg Cys Pro Phe Arg Trp Cys
1               5

<210> SEQ ID NO 37
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: MOD_RES
<222> LOCATION: (2)..(2)
<223> OTHER INFORMATION: homoCys
<220> FEATURE:
<221> NAME/KEY: misc_feature
<222> LOCATION: (2)..(7)
<223> OTHER INFORMATION: /note="Cyclic peptide"
<220> FEATURE:
<221> NAME/KEY: MOD_RES
<222> LOCATION: (3)..(4)
<223> OTHER INFORMATION: D-amino acid
<220> FEATURE:
<221> NAME/KEY: source
<223> OTHER INFORMATION: /note="C-term NH2"

<400> SEQUENCE: 37
```

Arg Cys Pro Phe Arg Trp Cys
1               5

<210> SEQ ID NO 38
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: misc_feature
<222> LOCATION: (2)..(8)
<223> OTHER INFORMATION: /note="Cyclic peptide"
<220> FEATURE:
<221> NAME/KEY: MOD_RES
<222> LOCATION: (5)..(5)
<223> OTHER INFORMATION: D-amino acid
<220> FEATURE:
<221> NAME/KEY: source
<223> OTHER INFORMATION: /note="C-term NH2"

<400> SEQUENCE: 38

Arg Cys Val Gln Phe Arg Trp Cys
1               5

<210> SEQ ID NO 39
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: misc_feature
<222> LOCATION: (2)..(8)
<223> OTHER INFORMATION: /note="Cyclic peptide"
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (5)..(5)
<223> OTHER INFORMATION: D-amino acid
<220> FEATURE:
<221> NAME/KEY: source
<223> OTHER INFORMATION: /note="C-term NH2"

<400> SEQUENCE: 39

Arg Cys Val Gln Phe Arg Trp Cys
1               5

<210> SEQ ID NO 40
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:

```
<221> NAME/KEY: misc_feature
<222> LOCATION: (2)..(8)
<223> OTHER INFORMATION: /note="Cyclic peptide"
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (4)..(4)
<223> OTHER INFORMATION: 1-Methyl-His
<220> FEATURE:
<221> NAME/KEY: MOD_RES
<222> LOCATION: (5)..(5)
<223> OTHER INFORMATION: D-amino acid
<220> FEATURE:
<221> NAME/KEY: source
<223> OTHER INFORMATION: /note="C-term NH2"

<400> SEQUENCE: 40

Arg Cys Val His Phe Arg Trp Cys
1               5

<210> SEQ ID NO 41
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: MOD_RES
<222> LOCATION: (1)..(1)
<223> OTHER INFORMATION: 3-(1,2,4,-triazol-1-yl)-L-Ala
<220> FEATURE:
<221> NAME/KEY: misc_feature
<222> LOCATION: (2)..(8)
<223> OTHER INFORMATION: /note="Cyclic peptide"
<220> FEATURE:
<221> NAME/KEY: MOD_RES
<222> LOCATION: (5)..(5)
<223> OTHER INFORMATION: D-amino acid
<220> FEATURE:
<221> NAME/KEY: source
<223> OTHER INFORMATION: /note="C-term NH2"

<400> SEQUENCE: 41

Ala Cys Ala Gln Phe Arg Trp Cys
1               5

<210> SEQ ID NO 42
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: misc_feature
<222> LOCATION: (2)..(8)
<223> OTHER INFORMATION: /note="Cyclic peptide"
<220> FEATURE:
<221> NAME/KEY: MOD_RES
<222> LOCATION: (5)..(5)
<223> OTHER INFORMATION: D-amino acid
<220> FEATURE:
<221> NAME/KEY: source
```

```
<223> OTHER INFORMATION: /note="C-term NH2"

<400> SEQUENCE: 42

Glu Cys Ala His Phe Arg Trp Cys
1               5

<210> SEQ ID NO 43
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: misc_feature
<222> LOCATION: (2)..(8)
<223> OTHER INFORMATION: /note="Cyclic peptide"
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (5)..(5)
<223> OTHER INFORMATION: D-amino acid
<220> FEATURE:
<221> NAME/KEY: source
<223> OTHER INFORMATION: /note="C-term OH"

<400> SEQUENCE: 43

Arg Cys Ala His Phe Arg Trp Cys
1               5

<210> SEQ ID NO 44
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term H"
<220> FEATURE:
<221> NAME/KEY: misc_feature
<222> LOCATION: (2)..(8)
<223> OTHER INFORMATION: /note="Cyclic peptide"
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (5)..(5)
<223> OTHER INFORMATION: D-amino acid
<220> FEATURE:
<221> NAME/KEY: source
<223> OTHER INFORMATION: /note="C-term OH"

<400> SEQUENCE: 44

Arg Cys Ala His Phe Arg Trp Cys
1               5

<210> SEQ ID NO 45
<211> LENGTH: 8
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term H"
<220> FEATURE:
<221> NAME/KEY: misc_feature
<222> LOCATION: (2)..(8)
<223> OTHER INFORMATION: /note="Cyclic peptide"
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (5)..(5)
<223> OTHER INFORMATION: D-amino acid
<220> FEATURE:
<221> NAME/KEY: source
<223> OTHER INFORMATION: /note="C-term NH2"

<400> SEQUENCE: 45

Arg Cys Ala His Phe Arg Trp Cys
1               5

<210> SEQ ID NO 46
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: 5-oxopyrrolidine-3-carboxylic acid
<220> FEATURE:
<221> NAME/KEY: MOD_RES
<222> LOCATION: (6)..(6)
<223> OTHER INFORMATION: D-amino acid
<220> FEATURE:
<221> NAME/KEY: source
<223> OTHER INFORMATION: /note="C-term NHEt"

<400> SEQUENCE: 46

Xaa His Trp Ser Tyr Leu Leu Arg Pro
1               5

<210> SEQ ID NO 47
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: 5-oxopyrrolidine-3-carboxylic acid
<220> FEATURE:
<221> NAME/KEY: MOD_RES
<222> LOCATION: (6)..(6)
<223> OTHER INFORMATION: D-tert-butyl-Ser
<220> FEATURE:
<221> NAME/KEY: source
<223> OTHER INFORMATION: /note="C-term NHEt"

<400> SEQUENCE: 47

Xaa His Trp Ser Tyr Ser Leu Arg Pro
1               5
```

```
<210> SEQ ID NO 48
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: 5-oxopyrrolidine-3-carboxylic acid
<220> FEATURE:
<221> NAME/KEY: MOD_RES
<222> LOCATION: (6)..(6)
<223> OTHER INFORMATION: D-Benzyl-His
<220> FEATURE:
<221> NAME/KEY: source
<223> OTHER INFORMATION: /note="C-term NHEt"

<400> SEQUENCE: 48

Xaa His Trp Ser Tyr His Leu Arg Pro
1               5

<210> SEQ ID NO 49
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: 5-oxopyrrolidine-3-carboxylic acid
<220> FEATURE:
<221> NAME/KEY: MOD_RES
<222> LOCATION: (5)..(5)
<223> OTHER INFORMATION: D-tert-butyl-Ser
<220> FEATURE:
<221> NAME/KEY: MOD_RES
<222> LOCATION: (10)..(10)
<223> OTHER INFORMATION: Hydrazinecarboxylic acid
<220> FEATURE:
<221> NAME/KEY: source
<223> OTHER INFORMATION: /note="C-term NH2"

<400> SEQUENCE: 49

Xaa His Trp Ser Tyr Ser Leu Arg Pro Gly
1               5                   10

<210> SEQ ID NO 50
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: 5-oxopyrrolidine-3-carboxylic acid
<220> FEATURE:
<221> NAME/KEY: MOD_RES
<222> LOCATION: (6)..(6)
<223> OTHER INFORMATION: D-amino acid
<220> FEATURE:
<221> NAME/KEY: source
<223> OTHER INFORMATION: /note="C-term NHEt"

<400> SEQUENCE: 50
```

Xaa His Trp Ser Tyr Trp Leu Arg Pro
1               5

<210> SEQ ID NO 51
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: 5-oxopyrrolidine-3-carboxylic acid
<220> FEATURE:
<221> NAME/KEY: MOD_RES
<222> LOCATION: (6)..(6)
<223> OTHER INFORMATION: D-(2-Naphthyl)-Ala
<220> FEATURE:
<221> NAME/KEY: source
<223> OTHER INFORMATION: /note="C-term NH2"

<400> SEQUENCE: 51

Xaa His Trp Ser Tyr Ala Leu Arg Pro Gly
1               5                   10

<210> SEQ ID NO 52
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: 5-oxopyrrolidine-3-carboxylic acid
<220> FEATURE:
<221> NAME/KEY: MOD_RES
<222> LOCATION: (6)..(6)
<223> OTHER INFORMATION: D-amino acid
<220> FEATURE:
<221> NAME/KEY: source
<223> OTHER INFORMATION: /note="C-term NH2"

<400> SEQUENCE: 52

Xaa His Trp Ser Tyr Trp Leu Arg Pro Gly
1               5                   10

<210> SEQ ID NO 53
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: 5-oxopyrrolidine-3-carboxylic acid
<220> FEATURE:
<221> NAME/KEY: MOD_RES
<222> LOCATION: (6)..(6)
<223> OTHER INFORMATION: D-2-Methyl-Trp
<220> FEATURE:
<221> NAME/KEY: source
<223> OTHER INFORMATION: /note="C-term NHEt"

<400> SEQUENCE: 53

Xaa His Trp Ser Tyr Trp Leu Arg Pro

```
<210> SEQ ID NO 54
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: MOD_RES
<222> LOCATION: (1)..(1)
<223> OTHER INFORMATION: D-(2-Naphthyl)-Ala
<220> FEATURE:
<221> NAME/KEY: MOD_RES
<222> LOCATION: (2)..(2)
<223> OTHER INFORMATION: 4-chloro-D-Phe
<220> FEATURE:
<221> NAME/KEY: MOD_RES
<222> LOCATION: (3)..(3)
<223> OTHER INFORMATION: D-Beta-(3-pyridiyl)-Ala
<220> FEATURE:
<221> NAME/KEY: MOD_RES
<222> LOCATION: (5)..(5)
<223> OTHER INFORMATION: Methyl-Tyr
<220> FEATURE:
<221> NAME/KEY: MOD_RES
<222> LOCATION: (6)..(6)
<223> OTHER INFORMATION: D-amino acid
<220> FEATURE:
<221> NAME/KEY: MOD_RES
<222> LOCATION: (8)..(8)
<223> OTHER INFORMATION: N6-isopropyl-L-Lys
<220> FEATURE:
<221> NAME/KEY: MOD_RES
<222> LOCATION: (10)..(10)
<223> OTHER INFORMATION: D-amino acid
<220> FEATURE:
<221> NAME/KEY: source
<223> OTHER INFORMATION: /note="C-term NH2"

<400> SEQUENCE: 54

Ala Phe Ala Ser Tyr Asn Leu Lys Pro Ala
1               5                   10

<210> SEQ ID NO 55
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: MOD_RES
<222> LOCATION: (1)..(1)
<223> OTHER INFORMATION: D-(2-Naphthyl)-Ala
<220> FEATURE:
<221> NAME/KEY: MOD_RES
<222> LOCATION: (2)..(2)
<223> OTHER INFORMATION: 4-chloro-D-Phe
<220> FEATURE:
<221> NAME/KEY: MOD_RES
<222> LOCATION: (3)..(3)
<223> OTHER INFORMATION: D-Beta-(3-pyridiyl)-Ala
<220> FEATURE:
<221> NAME/KEY: MOD_RES
<222> LOCATION: (6)..(6)
<223> OTHER INFORMATION: D-Cit
```

```
<220> FEATURE:
<221> NAME/KEY: MOD_RES
<222> LOCATION: (10)..(10)
<223> OTHER INFORMATION: D-amino acid
<220> FEATURE:
<221> NAME/KEY: source
<223> OTHER INFORMATION: /note="C-term NH2"

<400> SEQUENCE: 55

Ala Phe Ala Ser Tyr Xaa Leu Arg Pro Ala
1               5                   10

<210> SEQ ID NO 56
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: MOD_RES
<222> LOCATION: (1)..(1)
<223> OTHER INFORMATION: D-(2-Naphthyl)-Ala
<220> FEATURE:
<221> NAME/KEY: MOD_RES
<222> LOCATION: (2)..(2)
<223> OTHER INFORMATION: 4-chloro-D-Phe
<220> FEATURE:
<221> NAME/KEY: MOD_RES
<222> LOCATION: (3)..(3)
<223> OTHER INFORMATION: D-Beta-(3-pyridiyl)-Ala
<220> FEATURE:
<221> NAME/KEY: MOD_RES
<222> LOCATION: (5)..(5)
<223> OTHER INFORMATION: 4-(4S)-hexahydro-2,6-dioxo-
      4-pyrimidinyl(carbonyl)amino-Phe
<220> FEATURE:
<221> NAME/KEY: MOD_RES
<222> LOCATION: (6)..(6)
<223> OTHER INFORMATION: 4-Guanidino-D-Phe
<220> FEATURE:
<221> NAME/KEY: MOD_RES
<222> LOCATION: (8)..(8)
<223> OTHER INFORMATION: N6-isopropyl-L-Lys
<220> FEATURE:
<221> NAME/KEY: MOD_RES
<222> LOCATION: (10)..(10)
<223> OTHER INFORMATION: D-amino acid
<220> FEATURE:
<221> NAME/KEY: source
<223> OTHER INFORMATION: /note="C-term NH2"

<400> SEQUENCE: 56

Ala Phe Ala Ser Phe Phe Leu Lys Pro Ala
1               5                   10

<210> SEQ ID NO 57
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: MOD_RES
<222> LOCATION: (1)..(1)
<223> OTHER INFORMATION: D-(2-Naphthyl)-Ala
```

```
<220> FEATURE:
<221> NAME/KEY: MOD_RES
<222> LOCATION: (2)..(2)
<223> OTHER INFORMATION: D-2-amino-3-(4-chlorophenyl)propanoic acid
<220> FEATURE:
<221> NAME/KEY: MOD_RES
<222> LOCATION: (3)..(3)
<223> OTHER INFORMATION: D-Beta-(3-pyridiyl)-Ala
<220> FEATURE:
<221> NAME/KEY: MOD_RES
<222> LOCATION: (6)..(6)
<223> OTHER INFORMATION: D-(E)-N6-(N,N'-diethylcarbamimidoyl)-Lys
<220> FEATURE:
<221> NAME/KEY: MOD_RES
<222> LOCATION: (8)..(8)
<223> OTHER INFORMATION: (E)-N6-(N,N'-diethylcarbamimidoyl)-Lys
<220> FEATURE:
<221> NAME/KEY: MOD_RES
<222> LOCATION: (10)..(10)
<223> OTHER INFORMATION: D-amino acid
<220> FEATURE:
<221> NAME/KEY: source
<223> OTHER INFORMATION: /note="C-term NH2"

<400> SEQUENCE: 57

Ala Xaa Ala Ser Tyr Lys Leu Lys Pro Ala
1               5                   10

<210> SEQ ID NO 58
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-amino acid
<220> FEATURE:
<221> NAME/KEY: misc_feature
<222> LOCATION: (2)..(7)
<223> OTHER INFORMATION: /note="Cyclic peptide"
<220> FEATURE:
<221> NAME/KEY: MOD_RES
<222> LOCATION: (4)..(4)
<223> OTHER INFORMATION: D-amino acid
<220> FEATURE:
<221> NAME/KEY: source
<223> OTHER INFORMATION: /note="C-term OH"

<400> SEQUENCE: 58

Phe Cys Phe Trp Lys Thr Cys Thr
1               5

<210> SEQ ID NO 59
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-2-Naphthyl-Ala
<220> FEATURE:
<221> NAME/KEY: misc_feature
<222> LOCATION: (2)..(7)
<223> OTHER INFORMATION: /note="Cyclic peptide"
<220> FEATURE:
<221> NAME/KEY: MOD_RES
<222> LOCATION: (4)..(4)
```

```
<223> OTHER INFORMATION: D-amino acid
<220> FEATURE:
<221> NAME/KEY: source
<223> OTHER INFORMATION: /note="C-term NH2"

<400> SEQUENCE: 59

Ala Cys Tyr Trp Lys Val Cys Thr
1               5

<210> SEQ ID NO 60
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-amino acid
<220> FEATURE:
<221> NAME/KEY: misc_feature
<222> LOCATION: (2)..(7)
<223> OTHER INFORMATION: /note="Cyclic peptide"
<220> FEATURE:
<221> NAME/KEY: MOD_RES
<222> LOCATION: (4)..(4)
<223> OTHER INFORMATION: D-amino acid
<220> FEATURE:
<221> NAME/KEY: source
<223> OTHER INFORMATION: /note="C-term NH2"

<400> SEQUENCE: 60

Phe Cys Tyr Trp Lys Val Cys Trp
1               5

<210> SEQ ID NO 61
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: (4R)-4-(2-aminoethylcarbamoyloxy)-L-prolyl
<220> FEATURE:
<221> NAME/KEY: misc_feature
<222> LOCATION: (1)..(6)
<223> OTHER INFORMATION: /note="Cyclic peptide"
<220> FEATURE:
<221> NAME/KEY: MOD_RES
<222> LOCATION: (2)..(2)
<223> OTHER INFORMATION: L-phenylglycyl
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (5)..(5)
<223> OTHER INFORMATION: 4-O-benzyl-L-tyrosyl

<400> SEQUENCE: 61

Pro Xaa Trp Lys Tyr Phe
1               5

<210> SEQ ID NO 62
<211> LENGTH: 8
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: misc_feature
<222> LOCATION: (2)..(8)
<223> OTHER INFORMATION: /note="Cyclic peptide"
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (5)..(5)
<223> OTHER INFORMATION: 4-fluoro-D-Phe
<220> FEATURE:
<221> NAME/KEY: source
<223> OTHER INFORMATION: /note="C-term NH2"

<400> SEQUENCE: 62

Arg Cys Ala His Phe Arg Trp Cys
1               5

<210> SEQ ID NO 63
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: misc_feature
<222> LOCATION: (2)..(8)
<223> OTHER INFORMATION: /note="Cyclic peptide"
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (5)..(5)
<223> OTHER INFORMATION: 4-fluoro-D-Phe
<220> FEATURE:
<221> NAME/KEY: source
<223> OTHER INFORMATION: /note="C-term NH2"

<400> SEQUENCE: 63

Arg Cys Ala Ser Phe Arg Trp Cys
1               5

<210> SEQ ID NO 64
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: misc_feature
<222> LOCATION: (2)..(8)
<223> OTHER INFORMATION: /note="Cyclic peptide"
<220> FEATURE:
```

```
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (5)..(5)
<223> OTHER INFORMATION: 4-cyano-D-Phe
<220> FEATURE:
<221> NAME/KEY: source
<223> OTHER INFORMATION: /note="C-term NH2"

<400> SEQUENCE: 64

Arg Cys Ala Thr Phe Arg Trp Cys
1               5

<210> SEQ ID NO 65
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: misc_feature
<222> LOCATION: (2)..(8)
<223> OTHER INFORMATION: /note="Cyclic peptide"
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (5)..(5)
<223> OTHER INFORMATION: D-amino acid
<220> FEATURE:
<221> NAME/KEY: source
<223> OTHER INFORMATION: /note="C-term NH2"

<400> SEQUENCE: 65

Arg Cys Val Pro Phe Arg Trp Cys
1               5

<210> SEQ ID NO 66
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: misc_feature
<222> LOCATION: (2)..(8)
<223> OTHER INFORMATION: /note="Cyclic peptide"
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (5)..(5)
<223> OTHER INFORMATION: D-amino acid
<220> FEATURE:
<221> NAME/KEY: source
<223> OTHER INFORMATION: /note="C-term NH2"

<400> SEQUENCE: 66
```

Arg Cys Ser Pro Phe Arg Trp Cys
1               5

<210> SEQ ID NO 67
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: misc_feature
<222> LOCATION: (2)..(7)
<223> OTHER INFORMATION: /note="Cyclic peptide"
<220> FEATURE:
<221> NAME/KEY: MOD_RES
<222> LOCATION: (2)..(2)
<223> OTHER INFORMATION: homoCys
<220> FEATURE:
<221> NAME/KEY: MOD_RES
<222> LOCATION: (4)..(4)
<223> OTHER INFORMATION: D-amino acid
<220> FEATURE:
<221> NAME/KEY: source
<223> OTHER INFORMATION: /note="C-term OH"

<400> SEQUENCE: 67

Arg Cys Ala Phe Arg Trp Cys
1               5

<210> SEQ ID NO 68
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: MOD_RES
<222> LOCATION: (2)..(2)
<223> OTHER INFORMATION: homoCys
<220> FEATURE:
<221> NAME/KEY: misc_feature
<222> LOCATION: (2)..(7)
<223> OTHER INFORMATION: /note="Cyclic peptide"
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (4)..(4)
<223> OTHER INFORMATION: 4-fluoro-D-Phe
<220> FEATURE:
<221> NAME/KEY: source
<223> OTHER INFORMATION: /note="C-term NH2"

<400> SEQUENCE: 68

Arg Cys Ala Phe Arg Trp Cys
1               5

<210> SEQ ID NO 69
<211> LENGTH: 7
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: MOD_RES
<222> LOCATION: (1)..(1)
<223> OTHER INFORMATION: NorLeu
<220> FEATURE:
<221> NAME/KEY: MOD_RES
<222> LOCATION: (2)..(2)
<223> OTHER INFORMATION: homoCys
<220> FEATURE:
<221> NAME/KEY: misc_feature
<222> LOCATION: (2)..(7)
<223> OTHER INFORMATION: /note="Cyclic peptide"
<220> FEATURE:
<221> NAME/KEY: MOD_RES
<222> LOCATION: (4)..(4)
<223> OTHER INFORMATION: D-amino acid
<220> FEATURE:
<221> NAME/KEY: source
<223> OTHER INFORMATION: /note="C-term NH2"

<400> SEQUENCE: 69

Leu Cys Pro Phe Arg Trp Cys
1               5

<210> SEQ ID NO 70
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: homoCys
<220> FEATURE:
<221> NAME/KEY: misc_feature
<222> LOCATION: (2)..(7)
<223> OTHER INFORMATION: /note="Cyclic peptide"
<220> FEATURE:
<221> NAME/KEY: MOD_RES
<222> LOCATION: (4)..(4)
<223> OTHER INFORMATION: D-amino acid
<220> FEATURE:
<221> NAME/KEY: source
<223> OTHER INFORMATION: /note="C-term NH2"

<400> SEQUENCE: 70

Arg Cys Pro Phe Arg Trp Cys
1               5

<210> SEQ ID NO 71
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: CH3(CH2)4-CO-homoCys
<220> FEATURE:
<221> NAME/KEY: misc_feature
<222> LOCATION: (1)..(6)
<223> OTHER INFORMATION: /note="Cyclic peptide"
<220> FEATURE:
```

```
<221> NAME/KEY: MOD_RES
<222> LOCATION: (3)..(3)
<223> OTHER INFORMATION: D-amino acid
<220> FEATURE:
<221> NAME/KEY: source
<223> OTHER INFORMATION: /note="C-term NH2"

<400> SEQUENCE: 71

Cys Pro Phe Arg Trp Cys
1               5

<210> SEQ ID NO 72
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Benzyl-CO-homoCys
<220> FEATURE:
<221> NAME/KEY: misc_feature
<222> LOCATION: (1)..(6)
<223> OTHER INFORMATION: /note="Cyclic peptide"
<220> FEATURE:
<221> NAME/KEY: MOD_RES
<222> LOCATION: (3)..(3)
<223> OTHER INFORMATION: D-amino acid
<220> FEATURE:
<221> NAME/KEY: source
<223> OTHER INFORMATION: /note="C-term NH2"

<400> SEQUENCE: 72

Cys Pro Phe Arg Trp Cys
1               5

<210> SEQ ID NO 73
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: misc_feature
<222> LOCATION: (2)..(7)
<223> OTHER INFORMATION: /note="Cyclic peptide"
<220> FEATURE:
<221> NAME/KEY: MOD_RES
<222> LOCATION: (3)..(4)
<223> OTHER INFORMATION: D-amino acid
<220> FEATURE:
<221> NAME/KEY: MOD_RES
<222> LOCATION: (7)..(7)
<223> OTHER INFORMATION: 2,4-diaminobutyric acid
<220> FEATURE:
<221> NAME/KEY: source
<223> OTHER INFORMATION: /note="C-term NH2"

<400> SEQUENCE: 73

Arg Asp Ala Phe Arg Trp Xaa
1               5

<210> SEQ ID NO 74
<211> LENGTH: 7
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: misc_feature
<222> LOCATION: (2)..(7)
<223> OTHER INFORMATION: /note="Cyclic peptide"
<220> FEATURE:
<221> NAME/KEY: MOD_RES
<222> LOCATION: (3)..(4)
<223> OTHER INFORMATION: D-amino acid
<220> FEATURE:
<221> NAME/KEY: MOD_RES
<222> LOCATION: (7)..(7)
<223> OTHER INFORMATION: 2,3-diaminopropionic acid
<220> FEATURE:
<221> NAME/KEY: source
<223> OTHER INFORMATION: /note="C-term NH2"

<400> SEQUENCE: 74

Arg Glu Ala Phe Arg Trp Xaa
1               5

<210> SEQ ID NO 75
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: misc_feature
<222> LOCATION: (2)..(7)
<223> OTHER INFORMATION: /note="Cyclic peptide"
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (7)..(7)
<223> OTHER INFORMATION: 2,3-diaminopropionic acid
<220> FEATURE:
<221> NAME/KEY: source
<223> OTHER INFORMATION: /note="C-term NH2"

<400> SEQUENCE: 75

Arg Glu Ala Phe Arg Trp Xaa
1               5

<210> SEQ ID NO 76
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: misc_feature
<222> LOCATION: (2)..(7)
<223> OTHER INFORMATION: /note="Cyclic peptide"
<220> FEATURE:
```

```
<221> NAME/KEY: MOD_RES
<222> LOCATION: (2)..(2)
<223> OTHER INFORMATION: 2,3-diaminopropionic acid
<220> FEATURE:
<221> NAME/KEY: MOD_RES
<222> LOCATION: (3)..(4)
<223> OTHER INFORMATION: D-amino acid
<220> FEATURE:
<221> NAME/KEY: source
<223> OTHER INFORMATION: /note="C-term NH2"

<400> SEQUENCE: 76

Arg Xaa Ala Phe Arg Trp Glu
1               5

<210> SEQ ID NO 77
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: misc_feature
<222> LOCATION: (2)..(7)
<223> OTHER INFORMATION: /note="Cyclic peptide"
<220> FEATURE:
<221> NAME/KEY: MOD_RES
<222> LOCATION: (2)..(2)
<223> OTHER INFORMATION: 2,3-diaminopropionic acid
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (4)..(4)
<223> OTHER INFORMATION: 4-fluoro-D-Phe
<220> FEATURE:
<221> NAME/KEY: source
<223> OTHER INFORMATION: /note="C-term NH2"

<400> SEQUENCE: 77

Arg Xaa Ala Phe Arg Trp Glu
1               5

<210> SEQ ID NO 78
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: misc_feature
<222> LOCATION: (2)..(7)
<223> OTHER INFORMATION: /note="Cyclic peptide"
<220> FEATURE:
<221> NAME/KEY: MOD_RES
<222> LOCATION: (2)..(2)
<223> OTHER INFORMATION: 2,3-diaminopropionic acid
<220> FEATURE:
<221> NAME/KEY: MOD_RES
<222> LOCATION: (4)..(4)
<223> OTHER INFORMATION: D-amino acid
<220> FEATURE:
<221> NAME/KEY: source
```

<223> OTHER INFORMATION: /note="C-term NH2"

<400> SEQUENCE: 78

Arg Xaa Ala Phe Arg Trp Glu
1               5

<210> SEQ ID NO 79
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: misc_feature
<222> LOCATION: (2)..(7)
<223> OTHER INFORMATION: /note="Cyclic peptide"
<220> FEATURE:
<221> NAME/KEY: MOD_RES
<222> LOCATION: (2)..(2)
<223> OTHER INFORMATION: 2,3-diaminopropionic acid
<220> FEATURE:
<221> NAME/KEY: MOD_RES
<222> LOCATION: (4)..(4)
<223> OTHER INFORMATION: D-amino acid
<220> FEATURE:
<221> NAME/KEY: source
<223> OTHER INFORMATION: /note="C-term OH"

<400> SEQUENCE: 79

Arg Xaa Ala Phe Arg Trp Glu
1               5

<210> SEQ ID NO 80
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: MOD_RES
<222> LOCATION: (1)..(1)
<223> OTHER INFORMATION: NorLeu
<220> FEATURE:
<221> NAME/KEY: MOD_RES
<222> LOCATION: (2)..(2)
<223> OTHER INFORMATION: 2,3-diaminopropionic acid
<220> FEATURE:
<221> NAME/KEY: misc_feature
<222> LOCATION: (2)..(7)
<223> OTHER INFORMATION: /note="Cyclic peptide"
<220> FEATURE:
<221> NAME/KEY: MOD_RES
<222> LOCATION: (4)..(4)
<223> OTHER INFORMATION: D-amino acid
<220> FEATURE:
<221> NAME/KEY: source
<223> OTHER INFORMATION: /note="C-term NH2"

<400> SEQUENCE: 80

Leu Xaa Ala Phe Arg Trp Glu
1               5

<210> SEQ ID NO 81

```
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: 2,3-diaminopropionic acid
<220> FEATURE:
<221> NAME/KEY: misc_feature
<222> LOCATION: (2)..(7)
<223> OTHER INFORMATION: /note="Cyclic peptide"
<220> FEATURE:
<221> NAME/KEY: MOD_RES
<222> LOCATION: (4)..(4)
<223> OTHER INFORMATION: D-amino acid
<220> FEATURE:
<221> NAME/KEY: source
<223> OTHER INFORMATION: /note="C-term NH2"

<400> SEQUENCE: 81

Arg Xaa Ala Phe Arg Trp Glu
1               5

<210> SEQ ID NO 82
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: CH3-(CH2)4-CO-2,3-diaminopropionic acid
<220> FEATURE:
<221> NAME/KEY: misc_feature
<222> LOCATION: (1)..(6)
<223> OTHER INFORMATION: /note="Cyclic peptide"
<220> FEATURE:
<221> NAME/KEY: MOD_RES
<222> LOCATION: (3)..(3)
<223> OTHER INFORMATION: D-amino acid
<220> FEATURE:
<221> NAME/KEY: source
<223> OTHER INFORMATION: /note="C-term NH2"

<400> SEQUENCE: 82

Xaa Ala Phe Arg Trp Glu
1               5

<210> SEQ ID NO 83
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Benzyl-CO-2,3-diaminopropionic acid
<220> FEATURE:
<221> NAME/KEY: misc_feature
<222> LOCATION: (1)..(6)
<223> OTHER INFORMATION: /note="Cyclic peptide"
<220> FEATURE:
<221> NAME/KEY: MOD_RES
<222> LOCATION: (3)..(3)
<223> OTHER INFORMATION: D-amino acid
```

```
<220> FEATURE:
<221> NAME/KEY: source
<223> OTHER INFORMATION: /note="C-term NH2"

<400> SEQUENCE: 83

Xaa Ala Phe Arg Trp Glu
1               5

<210> SEQ ID NO 84
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: misc_feature
<222> LOCATION: (2)..(8)
<223> OTHER INFORMATION: /note="Cyclic peptide"
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (4)..(4)
<223> OTHER INFORMATION: 1-Methyl-His
<220> FEATURE:
<221> NAME/KEY: MOD_RES
<222> LOCATION: (5)..(5)
<223> OTHER INFORMATION: D-(2-Naphthyl)-Ala
<220> FEATURE:
<221> NAME/KEY: source
<223> OTHER INFORMATION: /note="C-term NH2"

<400> SEQUENCE: 84

Arg Cys Ala His Ala Arg Trp Cys
1               5

<210> SEQ ID NO 85
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: misc_feature
<222> LOCATION: (2)..(8)
<223> OTHER INFORMATION: /note="Cyclic peptide"
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (5)..(5)
<223> OTHER INFORMATION: D-(2-Naphthyl)-Ala
<220> FEATURE:
<221> NAME/KEY: source
<223> OTHER INFORMATION: /note="C-term NH2"

<400> SEQUENCE: 85

Arg Cys Ala Gln Ala Arg Trp Cys
1               5
```

```
<210> SEQ ID NO 86
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: misc_feature
<222> LOCATION: (2)..(8)
<223> OTHER INFORMATION: /note="Cyclic peptide"
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (5)..(5)
<223> OTHER INFORMATION: D-(2-Naphthyl)-Ala
<220> FEATURE:
<221> NAME/KEY: source
<223> OTHER INFORMATION: /note="C-term NH2"

<400> SEQUENCE: 86

Arg Cys Ala Asn Ala Arg Trp Cys
1               5

<210> SEQ ID NO 87
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: misc_feature
<222> LOCATION: (2)..(8)
<223> OTHER INFORMATION: /note="Cyclic peptide"
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (4)..(4)
<223> OTHER INFORMATION: 1-Methyl-His
<220> FEATURE:
<221> NAME/KEY: MOD_RES
<222> LOCATION: (5)..(5)
<223> OTHER INFORMATION: D-(2-Naphthyl)-Ala
<220> FEATURE:
<221> NAME/KEY: source
<223> OTHER INFORMATION: /note="C-term OH"

<400> SEQUENCE: 87

Arg Cys Ala His Phe Arg Trp Cys
1               5

<210> SEQ ID NO 88
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<220> FEATURE:
<221> NAME/KEY: source
<223> OTHER INFORMATION: /note="N-term Ac"
<220> FEATURE:
<221> NAME/KEY: misc_feature
<222> LOCATION: (2)..(8)
<223> OTHER INFORMATION: /note="Cyclic peptide"
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (5)..(5)
<223> OTHER INFORMATION: D-amino acid
<220> FEATURE:
<221> NAME/KEY: source
<223> OTHER INFORMATION: /note="C-term OH"

<400> SEQUENCE: 88

Arg Cys Ala Gln Phe Arg Trp Cys
1               5

<210> SEQ ID NO 89
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: misc_feature
<222> LOCATION: (2)..(8)
<223> OTHER INFORMATION: /note="Cyclic peptide"
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (5)..(5)
<223> OTHER INFORMATION: D-amino acid
<220> FEATURE:
<221> NAME/KEY: source
<223> OTHER INFORMATION: /note="C-term OH"

<400> SEQUENCE: 89

Arg Cys Ala Asn Phe Arg Trp Cys
1               5
```